US008007795B2

(12) United States Patent
Jiao et al.

(10) Patent No.: US 8,007,795 B2
(45) Date of Patent: Aug. 30, 2011

(54) ANTI-TISSUE FACTOR ANTIBODIES AND METHODS OF USE THEREOF

(75) Inventors: Jin-an Jiao, Fort Lauderdale, FL (US); Hing C. Wong, Fort Lauderdale, FL (US); Esperanza Liliana Nieves, Newark, DE (US); Luis A. Mosquera, Miami, FL (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 12/404,256

(22) Filed: Mar. 13, 2009

(65) Prior Publication Data

US 2009/0252726 A1 Oct. 8, 2009

Related U.S. Application Data

(63) Continuation of application No. 11/122,622, filed on May 5, 2005, now abandoned, which is a continuation of application No. 09/990,586, filed on Nov. 21, 2001, now abandoned.

(60) Provisional application No. 60/343,306, filed on Oct. 29, 2001.

(51) Int. Cl.
*A61K 39/395* (2006.01)

(52) U.S. Cl. ............... 424/133.1; 424/141.1; 424/144.1; 514/12.2; 514/14.3

(58) Field of Classification Search .................. None
See application file for complete search history.

(56) References Cited

U.S. PATENT DOCUMENTS

| 4,644,055 A | 2/1987 | Kettner et al. |
| 4,816,567 A | 3/1989 | Cabilly et al. |
| 5,122,458 A | 6/1992 | Post et al. |
| 5,168,062 A | 12/1992 | Stinski |
| 5,171,662 A | 12/1992 | Sharma |
| 5,216,132 A | 6/1993 | Basi |
| 5,223,427 A | 6/1993 | Edgington et al. |
| 5,225,539 A | 7/1993 | Winter |
| 5,385,839 A | 1/1995 | Stinski |
| 5,437,864 A | 8/1995 | Edgington et al. |
| 5,530,101 A | 6/1996 | Queen et al. |
| 5,534,254 A | 7/1996 | Huston et al. |
| 5,552,300 A | 9/1996 | Makrides et al. |
| 5,589,173 A | 12/1996 | O'Brien et al. |
| 5,639,641 A | 6/1997 | Pedersen et al. |
| 5,693,762 A | 12/1997 | Queen et al. |
| 5,766,886 A | 6/1998 | Studnicka et al. |
| 5,861,267 A | 1/1999 | Su |
| 5,869,046 A | 2/1999 | Presta et al. |
| 5,879,677 A | 3/1999 | del Zoppo |
| 5,889,157 A | 3/1999 | Pastan et al. |
| 5,958,713 A | 9/1999 | Thastrup et al. |
| 5,985,279 A | 11/1999 | Waldmann et al. |
| 5,986,065 A * | 11/1999 | Wong et al. .............. 530/388.22 |
| 5,997,867 A | 12/1999 | Waldmann et al. |
| 6,001,978 A | 12/1999 | Edgington et al. |
| 6,054,297 A | 4/2000 | Carter et al. |
| 6,117,639 A | 9/2000 | Germann et al. |
| 6,245,884 B1 | 6/2001 | Hook |
| 6,274,142 B1 | 8/2001 | O'Brien et al. |
| 6,287,366 B1 | 9/2001 | Derive et al. |
| 6,309,636 B1 | 10/2001 | do Couto et al. |
| 6,331,415 B1 | 12/2001 | Cabilly et al. |
| 6,333,167 B1 | 12/2001 | Quinet et al. |
| 6,555,319 B2 * | 4/2003 | Wong et al. .............. 435/7.1 |
| 6,593,291 B1 | 7/2003 | Green et al. |
| 6,610,293 B1 | 8/2003 | Fischer et al. |
| 6,677,436 B1 | 1/2004 | Sato et al. |
| 6,703,494 B2 | 3/2004 | Kirchhofer et al. |
| 6,986,894 B2 | 1/2006 | O'Brien et al. |
| 7,749,498 B2 | 7/2010 | Jiao et al. |
| 7,824,677 B2 | 11/2010 | Wong et al. |
| 2002/0025508 A1 | 2/2002 | Fechteler et al. |
| 2002/0065327 A1 | 5/2002 | Jiao et al. |
| 2003/0082636 A1 | 5/2003 | Wong et al. |
| 2003/0087372 A1 | 5/2003 | DelaCruz et al. |
| 2003/0109680 A1 | 6/2003 | Wong et al. |
| 2003/0119075 A1 | 6/2003 | Kirchhofer et al. |
| 2003/0124117 A1 | 7/2003 | Refino et al. |
| 2003/0176664 A1 | 9/2003 | Jiao et al. |
| 2004/0033200 A1 | 2/2004 | Ezban et al. |

(Continued)

FOREIGN PATENT DOCUMENTS

EP 0 239 400 A2 9/1987

(Continued)

OTHER PUBLICATIONS

Alberts et al. (2002). *The Cell*, Garland Science 4th edition, pp. 161, Fig. 3-42.

Albrecht et al. (1992). "An ELISA for Tissue Factor Using Monoclonal Antibodies," *Blood Coagulation and Fibrinolysis* 3:263-270.

Almus et al. (1990). "Properties of Factor VIIa/Tissue Factor Complexes in an Umbilical Vein Model," *Blood* 76(2):354-360.

Amirkhosravi et al. (2001). *Suppl. To J. of Thrombosis and Haemostasis* Abstract: OC1021.

Ardaillou et al. (1992). "Glomerular Tissue Factor Stimulates Thromboxane Synthesis in Human Platelets via Thrombin Generation," *Kidney International* 41:361-368.

(Continued)

*Primary Examiner* — Michael Szperka

(74) *Attorney, Agent, or Firm* — Morrison & Foerster LLP

(57) ABSTRACT

The invention includes antibodies that provide superior anticoagulant activity by binding native human TF with high affinity and specificity. Antibodies of the invention can effectively inhibit blood coagulation in vivo. Antibodies of the invention can bind native human TF, either alone or present in a TF:FVIIa complex, effectively preventing factor X or FIX binding to TF or that complex, and thereby reducing blood coagulation. Preferred antibodies of the invention specifically bind a conformational epitope predominant to native human TF, which epitope provides an unexpectedly strong antibody binding site. Also provided are humanized antibodies and fragments thereof that bind to the TF.

14 Claims, 17 Drawing Sheets

U.S. PATENT DOCUMENTS

| | | | |
|---|---|---|---|
| 2004/0126816 | A1 | 7/2004 | Kirchhofer et al. |
| 2004/0229282 | A1 | 11/2004 | Wong et al. |
| 2005/0089929 | A1 | 4/2005 | Jiao et al. |
| 2005/0271664 | A1 | 12/2005 | Wong et al. |
| 2006/0039901 | A1 | 2/2006 | Jiao et al. |
| 2006/0159675 | A1 | 7/2006 | Jiao et al. |
| 2006/0235209 | A9 | 10/2006 | Jiao et al. |
| 2009/0041766 | A1 | 2/2009 | Jiao et al. |
| 2009/0092602 | A1 | 4/2009 | Jiao et al. |
| 2009/0136501 | A1 | 5/2009 | Jiao et al. |

FOREIGN PATENT DOCUMENTS

| | | |
|---|---|---|
| EP | 0 239 400 A3 | 9/1987 |
| EP | 0 239 400 B1 | 9/1987 |
| EP | 0 420 937 B1 | 4/1991 |
| EP | 1 069 185 A1 | 1/2001 |
| JP | 4-502408 T | 5/1992 |
| JP | 1-503438 A | 11/1998 |
| JP | 2001-516214 T | 9/2001 |
| WO | WO-89/12463 A1 | 12/1989 |
| WO | WO-90/07861 A1 | 7/1990 |
| WO | WO-91/18019 A1 | 11/1991 |
| WO | WO-94/05328 A1 | 3/1994 |
| WO | WO-96/13593 A2 | 5/1996 |
| WO | WO-96/13593 A3 | 5/1996 |
| WO | WO-96/18105 A1 | 6/1996 |
| WO | WO-96/40921 A1 | 12/1996 |
| WO | WO-98/40408 A1 | 9/1998 |
| WO | WO-98/51321 A1 | 11/1998 |
| WO | WO-99/43713 A1 | 9/1999 |
| WO | WO-00/18398 A1 | 4/2000 |
| WO | WO-01/27079 A2 | 4/2001 |
| WO | WO-01/30333 A2 | 5/2001 |
| WO | WO-01/70984 A2 | 9/2001 |
| WO | WO-01/70984 A3 | 9/2001 |
| WO | WO-03/029295 A1 | 4/2003 |
| WO | WO-03/037911 A2 | 5/2003 |
| WO | WO-03/037911 A3 | 5/2003 |
| WO | WO-2005/004793 A2 | 1/2005 |
| WO | WO-2005/004793 A3 | 1/2005 |
| WO | WO-2005/004793 C2 | 1/2005 |
| WO | WO-2005/072126 A2 | 8/2005 |
| WO | WO-2005/072126 A3 | 8/2005 |

OTHER PUBLICATIONS

Asadullah, K. et al. (Dec. 1999). "The Pathophysiological Role of Cytokines in Psoriasis," *Drugs of Today* 35(12):913-924.

Barstad et al. (1995). "Procoagulant Human Monocytes Mediate Tissue Factor/Factor VIIa-Dependent Platelet-Thrombus Formation when Exposed to Flowing Nonanticoagulated Human Blood," *Arteriosclerosis, Thrombosis, and Vascular Biology* 15(1):11-16 (1995).

Beers et al. (1999). *The Merck Manual of Diagnosis and Therapy*, 17th edition, Merck Research Laboratories, pp. 1654-1681.

Benedict et al. (Feb. 1995). "Monoclonal Antibody to Tissue Factor Inhibits Intravascular Thrombosis without Impairing Extravascular Hemostasis," *JACC* Abstract 1012-1104, p. 366A.

Benhar et al. (1994). "Rapid Humanization of the Fv of Monoclonal Antibody B3 by Using Framework Exchange of the Recombinant Immunotoxin B3(Fv)-PE38," *Proc. Natl. Acad. Sci. USA* 91:12051-12055.

Bernhard, G.R. et al. (2001). "Efficacy and Safety of Recombinant Human Activated Protein C for Severe Sepsis," *The New England Journal of Medicine* 344:699-709.

Berzofsky, J.A. et al. (1993). "Immunogenicity and Antigen Structure," Chapter 8 in *Fundamental Immunology*, Paul, W.E. ed., Raven Press: New York, NY, p. 242.

Bird, R.E. et al. (Oct. 21, 1988). "Single-Chain Antigen-Binding Proteins," *Science* 242(4877):423-426.

Bjoern et al. (1991). "Human Plasma and Recombinant Factor VII," *The Journal of Biological Chemistry* 266(17):11051-10057.

Bokarewa et al. (Sep. 2002). "Intra-Articular Tissue Factor/Factor VII Complex Induces Chronic Arthritis," *Inflamm. Res.* 51(9):471-477.

Booy et al. (2006). "Monoclonal and Bispecific Antibodies as Novel Therapeutics," *Arch. Immunol. Ther. Exp.* 54:85-101.

Boulianne et al. (1984). "Production of Functional Chimeric Mouse/Human Antibody," *Nature* 312:643-646.

Broze, G.J., Jr. (1982). "Binding of Human Factor VII and VIIa to Monoytes," *J. Clin. Invest.* The American Society for Clinical Investigation, Inc. 70:526-535.

Bruggemann et al. (1989). "The Immunogenicity of Chimeric Antibodies," *J. Exp. Med.* 170:2153-2157.

Busso, N. et al. (Mar. 2003). "Role of the Tissue Factor Pathway in Synovial Inflammation," *Arthritis Rheum.* 48(3):651-659.

Cacia et al. (1996). "Isomerization of an Aspartic Acid Residue in the Complementarity-Determining Regions of a Recombinant Antibody to Human IgE: Identification and Effect on Binding Affinity," *Biochemistry* 35:1897-1903.

Camerer et al. (2000). "Tissue Factor—and Factor X-Dependent Activation of Protease-Activated Receptor 2 by Factor VIIa," *Proc. Natl. Acad. Sci. USA* 97(10):5255-5260.

Carraway, M.S. et al. (May 1, 2003). "Blockade of Tissue Factor," *American Journal of Respiratory and Critical Care Medicine* 167(9):1200-1209.

Carson et al. (1985). "Monoclonal Antibodies against Bovine Tissue Factor, which Block Interaction with Factor VII," *Blood* 66(1):152-156.

Carson et al. (1987). "An Inhibitory Monoclonal Antibody against Human Tissue Factor," *Blood* 70(2):490-493.

Carter et al. (1992). "Humanization of an Anti-p185HER2 Antibody for Human Cancer Therapy," *Proc. Natl. Acad. Sci. USA* 89:4285-4289.

Casipit et al. (1998). "Improving the Binding Affinity of an Antibody Using Molecular Modeling Site Directed Mutagenesis," *Protein Science* 7:1671-1680.

Cate et al. (1993). "The Activation of Factor X and Prothrombin by Recombinant Factor VIIa In Vivo is Mediated by Tissue Factor," *The Journal of Clinical Investigation* 92:1207-1212.

Caulfield, M.J. et al. (1992). "A Pathogenic Monoclonal Antibody, G8, is Characteristic of Antierythrocyte Autoantibodies from Coombs'-Positive NZB Mice," *The Journal of Immunology* 148(7):2069-2073.

Chapman et al. (1988). "Regulation of the Procoagulant Activity within the Bronchoalveolar Compartment of Normal Human Lung," *Am. Rev. Respir. Dis.* 137(6):1417-1425.

Chattopadhyay et al. (1992). "Molecular Recognition of Sites on Factor Xa which Participate in the Prothrombinase Complex," *The Journal of Biological Chemistry* 267(17):12323-12329.

Chothia, C. et al. (Dec. 1, 1988). "The Outline Structure of the T-Cell Alpha Beta Receptor," *The EMBO Journal* 7(12):3745-3755.

Clarke et al. (1992). "The First Epidermal Growth Factor Domain of Human Coagulation Factor VII is Essential for Binding with Tissue Factor," *Federation of European Biochemical Societies* 298(2,3):206-310.

Clarke, S. et al. (Oct. 1, 1990). "The BALB/c Secondary Response to the Sb Site of Influenza Virus Hemagglutinin. Nonrandom Silent Mutuation and Unequal Numbers of VH and Vk Mutations," *The Journal of Immunology* 145(7):2286-2296.

Co et al. (1991). "Humanized Antibodies for Antiviral Therapy," *Proc. Natl. Acad. Sci. USA* 88:2869-2873.

Collen et al. (1995). "New Thrombolytic Agents and Strategies," *Bailliere's Clinical Haematology* 8(2):425-435.

Colman, P.M. (1994). "Effects of Amino Acid Sequence Changes on Antibody-Antigen Interactions," *Research in Immunology* 145:33-36.

Contrino et al. (1994). "In Situ Characterization of Antigenic and Functional Tissue Factor Expression in Human Tumors Utilizing Monoclonal Antibodies and Recombinant Factor VIIa as Probes," *American Journal of Pathology* 145(6):1315-1322.

Couto et al. (1995). "Anti-BA46 Monoclonal Mc3: Humanization Using a Novel Positional Consensus and In Vivo and In Vitro Characterization," *Cancer Research* 55:1717-1722.

Couto et al. (1995). "Designing Human Consensus Antibodies with Minimal Positional Templates," *Cancer Research (Suppl.)* 55:5973s-5977s.

Cruse et al. (1995). *Illustrated Dictionary of Immunology*, CRC Press.

Database EMBL: MMG8LC, Accession #X60425, Oct. 21, 1991 Description "G8 (ANTI-MRBC) V(L), J(L)" XP-002305737.

Drake, F.A. et al. (1989). "Functional Tissue Factor is Entirely Cell Surface Expressed on Lipopolysaccharide-Stimulated Human Blood Monocytes and a Constitutively Tissue Factor-Producing Neoplastic Cell Line," *The Journal of Cell Biology* 109:389-395.

Drake et al. (1989). "Selective Cellular Expression of Tissue Factor in Human Tissues," *American Journal of Pathology* 134(5):1087-1097.

Erlich, J.H. et al. (Mar. 1997). "Tissue Factor Initiates Glomerular Fibrin Deposition and Promotes Major Histocompatibility Complex Class II Expression in Crescentic Glomerulonephritis," *American Journal of Pathology* 150(3)873-880.

Esmon, C.T. (2001). "Role of Coagulation Inhibitors in Inflammation," *Thrombosis and Haemostasis* 86(1)51-56.

Faber et al. (2001). "A Novel Method to Determine the Topology of Peroxisomal Membrane Proteins In Vivo Using the Tobacco Etch Virus Protease," *The Journal of Biological Chemistry* 276(39):36501-36507.

Faelber, K. et al. (Oct. 12, 2001). "The 1.85 Å Resolution Crystal Structures of Tissue Factor in Complex with Humanized Fab D3h44 and of Free Humanized Fab D3h44: Revisiting the Solvation of Antigen Combining Sites," *J. Mol. Biol.* 313(1):83-97. (Client).

Fair et al. (Aug. 25, 1987). "Cooperative Interaction between Factor VII and Cell Surface-Expressed Tissue Factor," *The Journal of Biological Chemistry* 262:11692-11698.

Faulk et al. (1990). "Tissue Factor: Identification and Characterization of Cell Types in Human Placentae," *Blood* 76(1):86-96.

Fay et al. (2005). "Mutating Factor VIII: Lessons from Structure to Function," *Blood Reviews* 19:15-17.

Final Office Action mailed Sep. 9, 2004, for U.S. Appl. No. 09/990,586, filed Nov. 21, 2001, 12 pages.

Final Office Action mailed Sep. 6, 2006, for U.S. Appl. No. 10/310,113, filed Dec. 4, 2002, 18 pages.

Final Office Action mailed Sep. 6, 2006, for U.S. Appl. No. 11/087,528, filed Mar. 22, 2005, 19 pages.

Final Office Action mailed Jan. 16, 2007, for U.S. Appl. No. 10/618,338, filed Jul. 11, 2003, 11 pages.

Final Office Action mailed Dec. 10, 2007, for U.S. Appl. No. 11/087,528, filed Mar. 22, 2005, by Wong et al., 12 pages.

Final Office Action mailed Feb. 1, 2008, for U.S. Appl. No. 10/310,113, filed Dec. 4, 2002, 14 pages.

Final Office Action mailed Jun. 19, 2008, for U.S. Appl. No. 10/618,338, filed Jul. 11, 2003, 12 pages.

Fiore, M.M. et al. (Dec. 15, 1992). "An Unusual Antibody that Blocks Tissue Factor/Factor VIIa Function by Inhibiting Cleavage Only of Macromolecular Substrates," *Blood* 80(12):3127-3134.

Flössel et al. (1994). "Immunohistochemical Detection of Tissue Factor (TF) on Paraffin Sections of Routinely Fixed Human Tissue," *Histochemistry* 01:449-453.

Foote et al. (1992). "Antibody Framework Residues Affecting the Conformation of the Hypervariable Loops," *J. Mol. Biol.* 224:487-499.

Francis et al. (2002). "Effect of Antihemostasis Agents on Experimental Tumor Dissemination," *Sem. in Thrombosis and Haemostasis* 28(1):29-38.

Furmaniak-Kazmierczak, E. et al. (Aug. 1994). "Studies of Thrombin-Induced Proteoglycan Release in the Degradation of Human and Bovine Cartilage," *J. Clin. Invest.* 92(2):472-480.

Gascoigne, N.R. et al. (May 1987). "Secretion of a Chimeric T-Cell Receptor-Immunoglobulin Protein," *Proc. Natl. Acad. Sci. USA* 84(9):2936-2940.

George et al. (1988). Chapter 12 in *Macromolecular Sequencing & Synthesis*, pp. 127-149.

Gorman et al. (1991). "Reshaping a Therapeutic CD4 Antibody," *Proc. Natl. Acad. Sci. USA* 88:4181-4185.

Gouault-Heilmann et al. (1975). "The Procoagulant Factor of Leukaemic Promyelocytes: Demonstration of Immunologic Cross Reactivity with Human Brain Tissue Factor," *British Journal of Haematology* 30:151-158.

Grabowski et al. (1993). "The Functional Expression of Tissue Factor by Fibroblasts and Endothelial Cells under Flow Conditions," *Blood* 81(2):3265-3270.

Grégoire, C. et al. (Sep. 15, 1991). "Engineered Secreted T-Cell Receptor Alpha Beta Heterodimers," *Proc. Natl. Acad. Sci. USA* 88(18):8077-81.

Griffiths et al. (1993). "Human Anti-Self Antibodies with High Specificity from Phage Display Libraries," *The EMBO Journal* 12(2):725-734.

Groves, D.J. et al. (Feb. 1987). "Production of an Ovine Monoclonal Antibody to Testosterone by an Interspecies Fusion," *Hybridoma* 6(1):71-76.

Hamaguchi et al. (1991). "FDP D-Dimer Induces the Secretion of Interleukin-1, Urokinase-Type Plasminogen Activator, and Plasminogen Activator Inhibitor-2 in a Human Promonocytic Leukemia Cell Line," *Blood* 77(1):94-100.

Hanes et al. (2000). "Picomolar Affinity Antibodies from a Fully Synthetic Naïve Library Selected and Evolved by Ribosome Display," *Nature Biotechnology* 18:1287-1292.

Hoffman et al. (1994). "Human Monocytes Support Factor X Activation by Factor VIIa, Independent of Tissue Factor: Implications for the Therapeutic Mechanism of High-Dose Factor VIIa in Hemophilia," *Blood* 83(1):38-42.

Houston, D.S. (2002). "Tissue Factor—A Therapeutic Target for Thrombotic Disorders," *Expert Opinion on Therapeutic Targets* 6(2):159-174.

Huang et al. (1998). "The Mechanism of an Inhibitory Antibody on TF-Initiated Blood Coagulation Revealed by the Crystal Structures of Human Tissue Factor, Fab 5G9 and TF5G9 Complex," *J. Mol. Biol.* 275:873-894.

Huston, J.S. et al. (Aug. 1988). "Protein Engineering of Antibody Binding Sites: Recovery of Specific Activity in an Anti-Digoxin Single-Chain Fv Analogue Produced in *Escherichia coli,*" *Proc. Natl. Acad. Sci. USA* 85(16):5879-5883.

Imamura et al. (1993). "Role of Macrophage Tissue Factor in the Development of the Delayed Hypersensitivity Reaction in Monkey Skin," *Cellular Immunology* 152:614-622.

International Search Report mailed on May 7, 1998, for PCT Application No. PCT/US98/04644, filed on Mar. 10, 1998, three pages. (25.40).

International Search Report mailed on Jun. 30, 2003, for PCT Application No. PCT/US02/034727, filed on Oct. 29, 2002, three pages. (26.40).

International Search Report mailed on May 18, 2005, for PCT Application No. PCT/US04/17900, filed on Jun. 4, 2004, two pages. (27. 40).

Ishihara, K. et al. (Aug. 2002-Oct. 2002). "IL-6 in Autoimmune Disease and Chronic Inflammatory Proliferative Disease," *Cytokine * Growth Factor Reviews* 13(4-5):357-368.

Ito et al. (1993). "Characterization of Functionally Important Regions of Tissue Factor by Using Monoclonal Antibodies," *J. Biochem.* 114(5):691-696.

Jager et al. (1993). "Current Status of Cancer Immunodetection with Radiolabeled Human Monoclonal Antibodies," *Seminars in Nuclear Medicine XXIII*(2):165-179.

James et al. (2002). "Inhibition of Tissue Factor Activity Reduces the Density of Cellular Network Formation in an In Vitro Model of Angiogenesis," *Biochemical Society Transactions* 30(2):217-221.

Janeway, C.A. Jr. et al. (1997). "Structure of the Antibody Molecule and Immunoglobulin Genes," Chapter 3 in "Part II, The Recognition of Antigen," in *Immunobiology*, 3rd edition, Garland Press, 3:1-1:11.

Janeway et al. (1997). *Immunobiology*, 3rd edition, Garland Press, 3:7-3:11.

Jang (1992). "Antithrombotic Effect of a Monoclonal Antibody against Tissue Factor in a Rabbit Model of Platelet-Mediated Arterial Thrombosis," *Arteriosclerosis and Thrombosis* 12(8):948-954.

Jones, P.T. et al. (May 29, 1986-Jun. 4, 1986). "Replacing the Complementarity-Determining Regions in a Human Antibody with Those from a Mouse," *Nature* 321(6069):522-525.

Junghans, R.P. et al. (Dec. 1, 1993). "Pharmacokinetics and Bioactivity of 1,4,7,10-tetra-azacyclododecane off,N",N""-tetraacetic acid (DOTA)-bismuth-conjugated anti-Tac Antibody for Alpha-Emitter (212Bi) Therapy, *Cancer Res.* 52(23):5683-5689.

Kao et al. (1993). "Chimeric Antibodies with Anti-Dextran-Derived Complementarity-Determining Regions and Anti-p-Azophenylarsonate-Derived Framework Regions," *The Journal of Immunology* 151:1968-1979.

Kappler, J. et al. (Aug. 30, 1994). "Binding of a Soluble Alpha Beta T-Cell Receptor to Superantigen/Major Histocompatibility Complex Ligands," *Proc. Natl. Acad. Sci. USA* 91(18):8462-8466.

Kincaid-Smith, P. (1975). "Participation of Intravascular Coagulation in the Pathogenesis of Glomerular and Vascular Lesions," *Kidney International* 7:242-253.

Kirchhofer, D. et al. (Dec. 2000). "Epitope Location on Tissue Factor Determines the Anticoagulant Potency of Monoclonal Anti-Tissue Factor Antibodies," *Thrombosis and Haemostatis* 84(6):1072-1081.

Kirchhofer et al. (2001). "The Tissue Factor Region that Interacts with Factor Xa in the Activation of Factor VII," *Biochemistry* 40:675-682.

Knappik et al. (2000). "Fully Synthetic Human Combinatorial Antibody Libraries (HuCAL) Based on Modular Consensus Frameworks and CDRs Randomized with Trinucleotides," *J. Mol. Biol.* 296:57-86.

Konigsberg et al. (2001). "The TF:VIIa Complex: Clinical Significance, Structure-Function Relationships and its Role in Signaling and Metastasis," *Thrombosis Haemostasis* 86:757-771.

Kozbor, D. et al. (1983). "The Production of Monoclonal Antibodies from Human Lymphocytes," *Immunology Today* 4:72-79.

Kumar et al. (1991). "Identification of Molecular Sites on Factor VII which Mediate its Assembly and Function in the Extrinsic Pathway Activation Complex," *The Journal of Biological Chemistry* 266(2):915-921.

Kumar et al. (1993). "Specific Molecular Interaction Sites on Factor VII Involved in Factor X Activation," *Eur. J. Biochem.* 217:509-518.

Kurucz, I. et al. (May 1, 1993). "A Bacterially Expressed Single-Chain Fv Construct from the 2B4 T-Cell Receptor," *Proc. Natl. Acad. Sci. USA* 90(9):3830-3834.

Leong et al. (2001). "Adapting Pharmacokinetic Properties of a Humanized Anti-Interleukin-8 Antibody for Therapeutic Applications Using Site-Specific Pegylation," *Cytokine* 16(3):106-119.

Levi et al. (1994). "Inhibition of Endotoxin-Induced Activation of Coagulation and Fibrinolysis by Pentoxifylline or by a Monoclonal Anti-Tissue Factor Antibody in Chimpanzees," *The Journal of Clinical Investigation, Inc.* 93:114-120.

Lewis, A.P. et al. (1993). "Generation of Humanized Monoclonal Antibodies by 'Best Fit' Framework Selection and Recombinant Polymerase Chain Reaction," *Year Immunol.* 7:110-118.

Lin, A.Y. et al. (Aug. 10, 1990). "Expression of T Cell Antigen Receptor Heterodimers in a Lipid-Linked Form," *Science* 249(4969):677-679.

Lobuglio et al. (1989). "Mouse/Human Chimeric Monoclonal Antibody in Man: Kinetics and Immune Response," *Proc. Natl. Acad. Sci. USA* 86:4220-4224.

Maekawa et al. (1993). "Complement-Dependent Immunosuppressive Anti-Tissue Factor Monoclonal Antibody: The Establishment of Monoclonal Antibodies and their Effect on Mixed Lymphocyte Reaction," *Transplantation Proceedings* 25(4):2713-2715.

Maimone, D. et al. (Jan. 1993). "T Cell Lymphokine-Induced Secretion of Cytokines by Monocytes from Patients with Multiple Sclerosis," *Cellular Immunology* 146(1):96-106.

Mariuzza, R.A. et al. (May 5, 1989). "Secretion of a Homodimeric V Alpha C Kappa T-Cell Receptor-Immunoglobulin Chimeric Protein," *Journal of Biological Chemistry* 264(13):7310-7316.

Martin et al. (1995). "Tissue Factor: Molecular Recognition and Cofactor Function," *The FASEB Journal* 9:852-859.

Martin et al. (Jun. 15, 1994). "Activation of Factor X by Factor VIIa on Monocyte Cell Surfaces," *Blood* 83(12):3828-3829.

Marty, I. et al. (Mar. 2001). "Amelioration of Collagen-Induced Arthritis by Thrombin Inhibition," *Journal of Clin. Invest.* 107(5):531-640.

Masuda et al. (1996). "Association of Tissue Factor with a γ Chain Homodimer of the IgE Receptor Type I in Cultured Human Monocytes," *Eur. J. Immunol.* 26:2529-2532.

Mateo et al. (1997). "Humanization of a Mouse Monoclonal Antibody that Blocks the Epidermal Growth Factor Receptor: Recovery of Antagonistic Activity," *Immunotechnology* 3:71-81.

Matthay, M.A. (2001). "Severe Sepsis—A New Treatment with Both Anticoagulant and Antiinflammatory Properties," *The New England Journal of Medicine* 344:759-762.

McGee et al. (1991). "Functional Difference between Intrinsic and Extrinsic Coagulation Pathways," *The Journal of Biological Chemistry* 266(13):8079-8085.

Mechtcheriakova, D. et al. (Jan. 2001). "Specificity, Diversity, and Convergence in VEGF and TNF-α Signaling Events Leading to Tissue Factor Up-Regulation via EGR-1 in Endothelial Cells," *The FASEB Journal* 15:230-242.

Medline Encyclopedia definition of "sepsis" located at <http://www.nlm.nih.gov/medlineplus/print/ency/article/000666.htm...>, last visited on Jul. 20, 2007, 3 pages.

Merriam-Webster Online Dictionary, downloaded Oct. 11, 2005, World Wide Web at m-w.com, Definition of Thrombosis, 2 pages.

Miller, D.L. et al. (Jun. 2002). "Extrinsic Coagulation Blockade Attenuates Lung Injury and Proinflammatory Cytokine Release after Intratracheal Lipopolysaccharide," *American Journal of Respiratory Cell and Molecular Biology* 26(6):650-658.

Minnema, M.C. et al. (Feb. 15, 2000). "Recombinant Human Antithrombin III Improves Survival and Attenuates Inflammatory Responses in Baboons Lethally Challenged with *Escherichia coli,*" *Blood* 95(4):1117-1123.

More, L. et al. (Aug. 1993). "Immunohistochemical Study of Tissue Factor Expression in Normal Intestine and Idiopathic Inflammatory Bowel Disease," *J. Clin. Pathol.* 46:703-708.

Morris, R. et al. (Jan. 1994). "Thrombin in Inflammation and Healing: Relevance to Rheumatoid Arthritis," *Annals of the Rheumatic Diseases* 53:72-79.

Morrison et al. (1984). "Chimeric Human Antibody Molecules: Mouse Antigen-Binding Domains with Human Constant Region Domains," *Proc. Natl. Acad. Sci. USA* 81:6851-6855.

Morrison, S. (1985). "Transfectomas Provide Novel Chimeric Antibodies," *Science* 229:1202-1207.

Morrison, S.L. (1992). "In Vitro Antibodies: Strategies for Production and Application," *Ann. Rev. Immunol.* 10:239-265.

Morrison, S.L. et al. (1989). "Genetically Engineered Antibody Molecules," *Advances in Immunology* 44:65-93.

Morrissey et al. (1988). "Monoclonal Antibody Analysis of Purified and Cell-Associated Tissue Factor," *Thrombosis Research* 52:247-261.

Morrissey et al. (1988). "Resolution of Monomeric and Heterodimeric Forms of Tissue Factor, the High-Affinity Cellular Receptor for Factor VII," *Thrombosis Research* 50:481-493.

Morrow, D.A. et al. (Apr. 2005). "Potent Inhibition of Thrombin with a Monoclonal Antibody Against Tissue Factor (Sunol-cH36): Results of the PROXIMATE-TIMI 27 Trial," *European Heart Journal* 26(7):682-688.

Mueller et al. (1992). "Expression of Tissue Factor by Melanoma Cells Promote Efficient Hemaotgenous Metasasis," *Proc. Natl. Acad. Sci. USA* 89:11832-11836.

Muller et al. (1994). "Structure of the Extracellular Domain of Human Tissue Factor: Location of the Factor VIIa Binding Site," *Biochemistry* 33:10864-10870.

Nakano, S. et al. (Mar. 1999-Apr. 1999). "Characteristics of the Protease Activity in Synovial Fluid from Patients with Rheumatoid Arthritis and Osteoarthritis," *Clinical and Experimental Rheumatology* 17:161-170.

Nemerson et al. (1986). "An Ordered Addition, Essential Activation Model of the Tissue Factor Pathway of Coagulation: Evidence for a Conformational Cage," *Biochemistry* 25:4020-4033.

Ngo, C.V. (2007, e-pub. Dec. 27, 2006). "CNTO 859, A Humanized Anti-Tissue Factor Monoclonal Antibody, is a Potent Inhibitor of Breast Cancer Metastasis and Tumor Growth in Xenograft Models," *Int. J. Cancer* 120:1261-1267.

Noguchi et al. (1989). "Correlation between Antigenic and Functional Expression of Tissue Factor on Surface of Cultured Human Endothelial Cells Following Stimulation by Lipopolysaccharide Endotoxin," *Thrombosis Research* 55:87-97.

Non-Final Office Action mailed Mar. 11, 2004, for U.S. Appl. No. 09/990,586, filed Nov. 21, 2001, 12 pages.

Non-Final Office Action mailed Sep. 22, 2004, for U.S. Appl. No. 10/293,417, filed Nov. 12, 2002, six pages.

Non-Final Office Action mailed Oct. 21, 2005, for U.S. Appl. No. 10/310,113, filed Dec. 4, 2002, 27 pages.
Non-Final Office Action mailed Mar. 24, 2006, for U.S. Appl. No. 11/087,528, filed Mar. 22, 2005, 13 pages.
Non-Final Office Action mailed Jun. 14, 2006, for U.S. Appl. No. 10/618,338, filed Jul. 11, 2003, 12 pages.
Non-Final Office Action mailed Apr. 4, 2007, for U.S. Appl. No. 11/087,528, filed Mar. 22, 2005, 15 pages.
Non-Final Office Action mailed May 11, 2007, for U.S. Appl. No. 10/310,113, filed Dec. 4, 2002, 14 pages.
Non-Final Office Action mailed Sep. 6, 2007, for U.S. Appl. No. 10/618,338, filed Jul. 11, 2003, eight pages.
Non-Final Office Action mailed Feb. 4, 2008, for U.S. Appl. No. 10/764,140, filed Jan. 22, 2004, 12 pages.
Non-Final Office Action mailed Sep. 15, 2008, for U.S. Appl. No. 11/122,622, filed May 5, 2005, 13 pages.
Non-Final Office Action mailed Feb. 4, 2009, for U.S. Appl. No. 10/618,338, filed Jul. 11, 2003, eight pages.
Non-Final Office Action mailed Dec. 30, 2009, for U.S. Appl. No. 12/136,718, filed Jun. 10, 2008, 12 pages.
Non-Final Office Action mailed Jun. 4, 2010, for U.S. Appl. No. 12/184,205, filed Jul. 31, 2008, seven pages.
Non-Final Office Action mailed Jul. 26, 2010, for U.S. Appl. No. 12/036,188, filed Feb. 22, 2008, 12 pages.
Novotny, J. et al. (Oct. 1, 1991). "A Soluble, Single-Chain T-Cell Receptor Fragment Endowed with Antigen-Combining Properties," *Proc. Natl. Acad. Sci. USA* 88(19):8646-8650.
OI, V.T. et al. (1986). "Chimeric Antibodies," *BioTechniques* 4(3):214-221.
Ollivier et al. (1998). "Tissue Factor-Dependent Vascular Endothelial Growth Factor Production by Human Fibroblasts in Response to Activated Factor VII," *Blood* 91(8):2698-2703.
Olsson, L. et al. (1983). "Human-Human Monoclonal Antibody-Producing Hybridomas: Technical Aspects," *Methods in Enzymology* 92:3-16.
Onda, T. et al. (Dec. 1995). "A Phage Display System for Detection of T Cell Receptor-Antigen Interactions," *Molecular Immunology* 32(17-18):1387-1397.
Østerud et al. (1979). "The Interaction of Human Blood Coagulation Factor VII and Tissue Factor: The Effect of Anti Factor VII, Anti Tissue Factor and Diisopropylfluorophosphate," *Biochemical and Biophysical Research Communications* 88(1):59-67.
Osterud, B. et al. (Jun. 2000). "Induction of Tissue Factor Expression in Whole Blood: Lack of Evidence for the Presence of Tissue Factor Expression in Granulocytes," *Thrombosis Haemostasis* 83:861-867.
Owens et al. (1994). "The Genetic Engineering of Monoclonal Antibodies," *Journal of Immunological Methods* 168:149-165.
Padlan (1990). "On the Nature of Antibody Combining Sites: Unusual Structural Features that May Confer on these Sites an Enhanced Capacity for Binding Ligands," *Proteins* 7:112-124.
Padlan (1991). "A Possible Procedure for Reducing the Immunogenicity of Antibody Variable Domains while Preserving their Ligand-Binding Properties," *Molecular Immunology* 28(4/5):489-498.
Padlan (1994). "Anatomy of the Antibody Molecule," *Molecular Immunology* 31(3):169-217.
Palmerini, T. et al. (Oct. 19, 2004). "Monocyte-Derived Tissue Factor Contributes to Stent Thrombosis in an In Vitro System," *J. Am. Coll. Cardio.* 44(8):1570-1577.
Parmley, S.F. et al. (Dec. 20, 1988). "Antibody-Selectable Filamentous Fd Phage Vectors: Affinity Purification of Target Genes," *Gene* 73(2):305-318.
Pawashe et al. (Jan. 1994). "A Monoclonal antibody against Rabbit Tissue Factor Inhibits Thrombus Formation in Stenotic Injured Rabbit Carotid Arteries," *Tissue Factor and Intravascular Thrombosis* 74(1):56-63.
Ploplis et al. (Jul. 15, 1987). "Initiation of the Extrinsic Pathway of Coagulation—Association of Factor VIIa with a Cell Line Expressing Tissue Factor," *The Journal of Biological Chemistry* 262:9503-9508.
Portolano, S. et al. (Feb. 1, 1993). "Lack of Promiscuity in Autoantigen-Specific H and L Chain Combinations as Revealed by Human H and L Chain 'Roulette'," *J. Immunology* 150(3):880-887.

Poster Presentation: *Experimental Biology* 2001, Mar. 31-Apr. 4, 2001, Orlando, Florida, Anti-Tissue Factor Antibodies, Poster No. 946: "Immunotherapy of Cancer," 14 pages.
Presta et al. (2001). "Generation of a Humanized, High Affinity Anti-Tissue Factor Antibody for Use as a Novel Antithrombotic Therapeutic," *Thrombosis Haemostasis* 85:379-389.
Price et al. (2004). "Tissue Factor and Tissue Factor Pathway Inhibitor," *Anaesthesia* 59:483-492.
Queen et al. (1989). "A Humanized Antibody that Binds to the Interleukin 2 Receptor," *Proc. Natl. Acad. Sci. USA* 86:10029-10033.
Queen et al. (1989). "Cell-Type Specific Regulation of a k Immunoglobin Gene by Promoter and Enhancer Elements," *Immunological Reviews* 89:49-68.
Ragni, M. et al. (May 15, 1996). "Monoclonal Antibody against Tissue Factor Shortens Tissue Plasminogen Activator Lysis Time and Prevents Reocclusion in a Rabbit Model of Carotid Artery Thrombosis," *Circulation* 93(10):1913-1918.
Rangel-Frausto, M.S. (2005). Sepsis: Still Going Strong, *Archives of Medical Research* 36:672-681.
Rao, L.V. et al. (Oct. 1, 1989). "Purification and Characterization of Rabbit Tissue Factor," *Thrombosis Research* 56:109-118.
Rehemtulla et al. (Jun. 5, 1991). "The Integrity of the Cysteine 186-Cysteine 209 Bond of the Second Disulfide Loop of Tissue Factor is Required for Binding of Factor VII," *The Journal of Biological Chemistry* 266(16):10294-10299.
Reichart (2001). "Monocolonal Antibodies in the Clinic," *Nature Biotechnology* 19:819-822.
Reichmann et al. (1988). "Reshaping Human Antibodies for Therapy," *Nature* 332:323-327.
Riewald et al. (2001). "Mechanistic Coupling of Protease Signaling and Initiation of Coagulation by Tissue Factor," *Proc. Natl. Acad. Sci. USA* 98(14):7742-7747.
Roberston (2002). "Genentech Awarded Critical Antibody Patent," *Nature Biotechnology* 20:108.
Roguska et al. (1994). "Humanization of Murine Monoclonal Antibodies through Variable Domain Resurfacing," *Protein Engineering* 9(10):895-904.
Roguska et al. (1996). "A Comparison of Two Murine Monoclonal Antibodies Humanized by CDR-Grafting and Variable Domain Resurfacing," *Protein Engineering* 9(10):895-904.
Rudikoff et al. (1982). "Single Amino Acid Substitution Altering Antigen-Binding Specificity," *Proc. Natl. Acad. Sci. USA* 79:1979-1983.
Ruf et al. (1991). "An Anti-Tissue Factor Monoclonal Antibody which Inhibits TF-VIIa Complex is a Potent Anticoagulant in Plasma," *Thrombosis and Haemostasis*, F.K. Schattauer Verlagsgesellschaft mbH (Stuttgart) 66(5):529-533.
Ruf et al. (1991). "Antibody Mapping of Tissue Factor Implicates Two Different Exon-Encoded Regions in Function," *Biochem. J.* 278:729-733.
Ruf et al. (Feb. 5, 1991). "Phospholipid-Independent and -Dependent Interactions required for Tissue Factor Receptor and Cofactor Function," *The Journal of Biological Chemistry* 266:2158-2166.
Ruf et al. (Aug. 25, 1991). "Characterization of Factor VII Association with Tissue Factor in Solution—High and Low Affinity Calcium Binding Sites in Factor VII Contribute to Functionally Distinct Interactions," *The Journal of Biological Chemistry* 26:15719-15725.
Ruf et al. (Oct. 1991). "Two Sites in the Tissue Factor Extracellular Domain Mediate the Recognition of the Ligand Factor VIIa," *Proc. Natl. Acad. Sci. USA* 88:8430-8434.
Ruf et al. (Nov. 5, 1992). "Tissue Factor Residues 157-167 are Required for Efficient Proteolytic Activation of Factor X and Factor VII," *The Journal of Biological Chemistry* 267(31):22206-22210.
Ruf et al. (Apr. 1994). "Structural Biology of Tissue Factor, the Initiator of Thrombogenesis In Vivo," *The FASEB Journal* 8:385-390.
Ruf et al. (1999). "Tissue Factor Signaling," Thrombosis and Haemostasis 82(2):175-182.
Ryan et al. (Aug. 15, 1992). "Tumor Necrosis Factor-Induced Endothelial Tissue Factor is Associated with Subendothelial Matrix Vesicles but is not Expressed on the Apical Surface," *Blood* 80(4):966-974.
Sakai et al. (Jun. 15, 1989). "Binding of Human Factors VII and VIIa to a Human Bladder Carcinoma Cell Line (J82)—Implications for the Initiation of the Extrinsic Pathways of Blood Coagulation," *The Journal of Biological Chemistry* 264(17):9980-9988.

Salatti et al. (1993). "Modulation of Procoagulant Activity of Extracellular Endothelial Matrix by Anti-Tissue Factor Antibody and the Synthetic Peptide Arg-Gly-Asp-Val. Experiments with Flowing Non-Anticoagulated Human Blood," *Blood Coagulation and Fibrinolysis* 4:881-890.

Saldanha et al. (1999). "A Single Backmutation in the Human kIV Framework of a Previously Unsuccessfully Humanized Antibody Restores the Binding Activity and Increases the Secretion in cos Cells," *Molecular Immunology* 36:709-719.

Sandset et al. (Sep. 15, 1991). "Immunodepetion of Extrinsic Pathway Inhibitor Sensitizes Rabbits to Endotoxin-Induced Intravascular Coagulation and the Generalized Schwartzman Reaction," *Blood* 78(6):1496-1502.

Schlueter, C.J. et al. (Mar. 15, 1996). "Specificity and Binding Properties of a Single-Chain T Cell Receptor," *Journal of Molecular Biology* 256(5):859-869.

Schopf, R.E. et al. (1993). "Enhanced Procoagulant Activity of Mononuclear Leukocytes in Patients with Atopic Dermatitis and Psoriasis," *Arch. Dermatol. Res.* 285:305-309.

Segal, J. et al. (Dec. 2000). "Tissue Factor Activity in Patients with Systemic Lupus Erythematosus: Association with Disease Activity," *The Journal of Rheumatology* 27:2827-2832.

Shearman et al. (1991). "Construction, Expression and Characterization of Humanized Antibodies Directed against the Human α/β T Cell Receptor", *The Journal of Immunology* 147:4366-4373.

Shen, B.Q. et al. (Feb. 16, 2001). "Vascular Endothelial Growth Factor KDR Receptor Signaling Potentiates Tumor Necrosis Factor-Induced Tissue Factor Expression in Endothelial Cells," *The Journal of Biological Chemistry* 276(7):5281-5286.

Skopouli et al. (1995). "Cytokines in Sjogren's Syndrome," *Annales de Medecine Interne* 146(4):219-222.

Smith, G.P. et al. (1993). "Libraries of Peptides and Proteins Displayed on Filamentous Phage," *Methods in Enzymology*, 217:228-257.

Soo Hoo, W.F. et al. (May 15, 1992). "Characterization of a Single-Chain T-Cell Receptor Expressed in *Escherchia coli*," *Proc. Natl. Acad. Sci. USA* 89(10):4759-63.

Speidel et al. (Jan. 1996). "Procoagulant Activity on Injured Arteries and Associated Thrombi is Mediated Primarily by the Complex of Tissue Factor and Factor VIIa," *Pathophysiology and Natural History, Coronary Artery Disease* 7(1):58-62.

Stephens et al. (1994). "Production of Tissue Factor by Monocyte Progenitor Cells," *Thrombosis Research* 76(1):33-45.

Sturm et al. (1992). "Immunohistological Detection of Tissue Factor inNormal and Abnormal Human Mammary Glands Using Monoclonal Antibodies," *Virchows Archive A Pathological Anatomy and Histopathology* 421:79-86.

Tan et al. (2002). "Superhumanized Antibodies: Reduction of Immunogenic Potential by Complementarity-Determining Region Grafting with Human Germline Sequences: Application to an Anti-CD28," *The Journal of Immunology* 169:1119-1125.

Taylor et al. (1987). "Protein C Prevents the Coagulopathic and Lethal Effects of *Escherichia coli* Infusion in the Baboon," *J. Clin. Invest.* 79:918-925.

Taylor, F.B. Jr. (Mar. 1991). "Lethal *E. coli* Septic Shock is Prevented by Blocking Tissue Factor with Monoclonal Antibody," *Circ. Shock* 33(3):127-134.

Taylor, F.B. (2001). "Staging of the Pathophysiologic Responses of the Primate Microvasculature to *Escherichia coli* and Endotoxin: Examination of the Elements of the Compensated Response and their Links to the Corresponding Uncompensated Lethal Variants," *Crit. Care. Med.* 29(7):578-89.

Tempest et al. (1991). "Reshaping a Human Monoclonal Antibody to Inhibit Human Respiratory Syncytial Virus Infection In Vivo," *Bio/Technology* 9:266-271.

Teng et al. (1983). "Construction and Testing of Mouse-Human Hetermyelomas for Human Monoclonal Antibody Production," *Proc. Natl. Acad. Sci. USA* 80:7308-7312.

Tomizuka et al. (2000). Double Trans-Chromosomic Mice; Maintenance of Two Individual Human Chromosome Fragments Containing Ig heavy and k lock and Expression of Fully Human Antibodies, *Proc. Natl. Acad. Sci. USA* 97(2):722-727.

Toomey et al. (Oct. 15, 1991). "Localization of the Human Tissue Factor Recognition Determinant of Human Factor VIIa," *The Journal of Biological Chemistry* 266(20):19198-19202.

Tsao et al. (Apr. 1984). "Monocytes can be Induced by Lipopolysaccharide-Triggered T Lymphocytes to Express Functional Factor VII/VIIa Protease Activity," *J. Exp. Med.* 159:1042-1057.

Tsuda et al. (Jul. 1, 1993). "Development of Antitissue Factor Antibodies in Patients after Liver Surgery," *Blood* 82(1):96-102.

Varisco P.A. et al. (Oct. 2000). "Effect of Thrombin Inhibition on Synovial Inflammation in Antigen Induced Arthritis," *Annals of Rheumatic Diseases* 59(10):781-787.

Vaughan et al. (1996). "Human Antibodies with Sub-Nanomolar Affinities Isolated from a Large Non-Immunized Phage Display Library," *Nature Biotechnology* 14:309-314.

Verhoeyen et al. (1988). "Reshaping Human Antibodies: Grafting an Antilysozyme Activity," *Science* 239:1534-1536.

Wakefield, A.J. et al. (Feb. 1994). "Immunohistochemical Study of Vascular Injury in Acute Multiple Sclerosis," *Journal of Clinical Pathology* 47(2):129-133.

Walsh, J.D. et al. (1991). "Discordant Expression of Tissue Factor Antigen and Procoagulant Activity on Human Monocytes Activated with LPS and Low Dose Cycloheximide," *Thrombosis and Haemostasis*, F.K. Achattauer Verlagsgesellschaft mbH (Stuttgart) 66(5):552-558.

Ward, E.S. (Aug. 1991). "Expression and Secretion of T-Cell Receptor V Alpha and V Beta Domains Using *Escherichia coli* as a Host," *Scand. J. Immunol.* 34:215-220.

Ward, E.S. (Apr. 20, 1992). "Secretion of T Cell Receptor Fragments from Recombinant *Escherichia coli* Cells," *Journal of Molecular Biology* 224(4):885-890.

Warr et al. (Apr. 1, 1990). "Disseminated Intravascular Coagulation in Rabbits Induced by Administration of Endotoxin or Tissue Factor: Effect of Anti-Tissue Factor Antibodies and Measurement of Plasma Extrinsic Pathway Inhibitor Activity," *Blood* 75(7):1481-1489.

Watson et al. (1987). *Molecular Biology of the Gene*, $4^{th}$ edition, The Benjamin/Cummings Publishing Company, Inc., 840.

Webber, K.O. et al. (Mar. 1995). "Preparation and Characterization of a Disulfide-Stabilized Fv Fragment of the Anti-Tac Antibody: Comparison with its Single-Chain Analog," *Molecular Immunology* 32(4):249-258.

Weinberg, J.B. et al. (Aug. 1991). "Extravascular Fibrin Formation and Dissolution in Synovial Tissue of Patients with Osteoarthritis and Rheumatoid Arthritis," *Arthritis and Rheumatism* 34(8):996-1005.

Welty-Wolf, K.B. et al. (Nov. 15, 2001). "Coagulation Blockade Prevents Sepsis-Induced Respiratory and Renal Failure in Baboons," *American Journal of Respiratory and Critical Care Medicine* 164(10 Pt 1):1988-1996.

Welty-Wolf, K.E. et al. (Oct. 2001). "Tissue Factor in Experimental Acute Lung Injury," *Seminars in Hematology* 38(4):35-38.

Welty-Wolf, K.E. et al. (Jan. 2006, e-pub. Aug. 12, 2005). "Blockade of Tissue Factor-Factor X Binding Attenuates Sepsis-Induced Respiratory and Renal Failure," *Am. J. Physiol. Cell. Mol. Physiol.* 290(1, pt. 1):L21-L31.

Wen Jinghai et al. (2001). "Antibody-Dependent Cellular Cytotoxicity and Antibody Dependent Cellular Phagocytosis of Breast Cancer Cells Mediated by Anti-Tissue Factor Monoclonal Antibodies," *FASEB Journal* 15(5):A1198. Annual Meeting of the Federation of American Societies for Experimental Biology on Experimental Biol; Orlando, Florida, Mar. 31-Apr. 4, 2001 Abstract.

Wiiger et al. (2000). "Effects of Binding of Ligand (FVIIa) to Induced Factor in Human Endothelial Cells," *Thrombosis Research* 98:311-321.

Written Opinion mailed on Oct. 7, 2004, for PCT Application No. PCT/US02/34727, filed on Oct. 29, 2002, five pages.

Wulfing, C. et al. (Oct. 7, 1994). "Correctly Folded T-Cell Receptor Fragments in the Periplasm of *Escherichia coli*. Influence of Folding Catalysts," *Journal of Molecular Biology* 242(5):655-669.

Yamashita, H. et al. (e-pub. Oct. 25, 2006). "Tissue Factor Expression Is a Clinical Indicator of Lymphatic Metastasis and Poor Prognosis in Gastric Cancer with Intestinal Phenotype," *J. Surg. Oncol.* pp. 1-8.

Zeher, M. et al. (May 1994). "Fibrinolysis-Resistant Fibrin Deposits in Minor Labial Salivary Glands of Patients with Sjogren's Syndrome," *Clinical Immunology and Immunopathology* 71(2):149-155.

* cited by examiner

H36.D2.B7 ANTI-TISSUE FACTOR LIGHT CHAIN VARIABLE REGION

GACATTCAGATGACCCAGTCTCCAGTCTCCTGCCTCCGTCATCTCTGGGAGAAAGTGTCACCATCACATGC
 D   I   Q   M   T   Q   S   P   A   S   S   L   G   E   S   V   T   I   T   C

CTGGCAAGTCAGTCAGACCATTGATACATGGTTAGCATGGTATCAGCAGAAACCAGGGAAATCTCCTCAGCTC
 <u>L   A   S   Q   T   I   D</u>   T   W   L   A   W   Y   Q   Q   K   P   G   K   S   P   Q   L

CTGATTTATGCTGCCACCAACTTGGCAGATGGGGTCCCATCAAGGTTCAGTGGCAGTGGATCTGGCACA
 L   I   Y   <u>A   A   T   N   L   A   D</u>   G   V   P   S   R   F   S   G   S   G   S   G   T

AAATTTCTTTCAAGATCAGCAGCCTACAGGCTGAAGATTTTGTAAATTATTACTGTCAACAAGTTTAC
 K   F   S   F   K   I   S   S   L   Q   A   E   D   F   V   N   Y   Y   C   <u>Q   Q   V   Y</u>

AGTTCTCCATTCACGTTCGGTGCTGGGACCAAGCTGGAGCTGAAA
 <u>S   S   P   F   T</u>   F   G   A   G   T   K   L   E   L   K

FIG. 1A

H36.D2.B7 ANTI-TISSUE FACTOR HEAVY CHAIN VARIABLE REGION

GAGATCCAGCTGCAGCAGTCTGGACCTGAGCTGGTGAAGCCTGGGGCTTCAGTGCAGGTATCCTGCAAG
 E  I  Q  L  Q  Q  S  G  P  E  L  V  K  P  G  A  S  V  Q  V  S  C  K

ACTTCTGGTTACTCATTCACTGACTACAACGTGTACTGGGTGAGGCAGAGCCATGGAAAGAGCCTTGAG
 T  S  G  Y  S  F  T  D  Y  N  V  Y  W  V  R  Q  S  H  G  K  S  L  E

TGGATTGGATATATTGATCCTTACAATGGTATTATCTACGACCAGAACTTCAAGGGCAAGGCCACA
 W  I  G  Y  I  D  P  Y  N  G  I  T  I  Y  D  Q  N  F  K  G  K  A  T

TTGACTGTTGACAAGTCTTCCACCACAGCCTTCATGCATCTCAACAGCCTGACATCTGACGACTCTGCA
 L  T  V  D  K  S  S  T  T  A  F  M  H  L  N  S  L  T  S  D  D  S  A

GTTTATTTCTGTGCAAGAGATGTGACTACGGCCCTTGACTTCTGGGGCCAAGGCACCACTCTCACAGTC
 V  Y  F  C  A  R  D  V  T  T  A  L  D  F  W  G  Q  G  T  T  L  T  V

TCCTCA
 S  S

FIG. 1B

| ANTIBODY | APPARENT $K_1$, $M^{-1}$ | APPARENT $K_1$, M |
|---|---|---|
| BY ELISA | | |
| D2 | $5.2 \times 10^9$ | $1.9 \times 10^{-10}$ |
| I47 | $6.5 \times 10^9$ | $1.5 \times 10^{-10}$ |
| K73 | $9.8 \times 10^9$ | $1.0 \times 10^{-10}$ |
| K80 | $2.3 \times 10^9$ | $4.3 \times 10^{-10}$ |
| L102 | $2.5 \times 10^9$ | $4.0 \times 10^{-10}$ |
| L133 | $1.7 \times 10^9$ | $5.9 \times 10^{-10}$ |
| BY BIACore | | |
| H36 | $3.1 \times 10^{10}$ | $3.2 \times 10^{-11}$ |
| I43 | $2.3 \times 10^9$ | $4.3 \times 10^{-10}$ |
| I47 | $3.2 \times 10^9$ | $3.1 \times 10^{-10}$ |
| L133 | $4.6 \times 10^9$ | $2.2 \times 10^{-10}$ |
| M107 | $1.1 \times 10^9$ | $9.1 \times 10^{-10}$ |

FIG. 2

| ANTIBODY NAME | % INHIBITION ANTIBODY PREINCUBATED WITH TF/VIIa |
|---|---|
| D1 | 0 |
| D1B | 1 |
| H31 | 4 |
| H36 | 95 |
| I43 | 1 |
| J131 | 7 |
| K80 | 0 |
| K82 | 0 |
| K87 | 1 |
| L97B | 7 |
| L101 | 0 |
| L102 | 0 |
| L105 | 0 |
| L133 | 0 |
| M5 | 1 |
| M107 | 34 |

FIG. 3

| ANTIBODY NAME | % INHIBITION TF PREINCUBATED WITH ANTIBODY PRIOR TO ADDITION OF VIIa | % INHIBITION TF PREINCUBATED WITH VIIa PRIOR TO ADDITION OF ANTIBODY |
|---|---|---|
| D1 | 15 | nd |
| D1B | 48 | 12.7 |
| H31 | 64 | 21 |
| H36 | 0 | 0 |
| I43 | 68 | 55 |
| J131 | 38 | 11 |
| K80 | 12 | nd |
| K82 | 0 | nd |
| K87 | 0 | nd |
| L96 | 0 | nd |
| L101 | 38 | 11 |
| L102 | 14 | nd |
| L105 | 4 | nd |
| L133 | 13 | nd |
| M5 | 0 | nd |
| M107 | 0 | nd |

FIG. 4

| [rhTF], nM | [H36.D2], nM | H36.D2/rhTF MOLAR RATIO | CLOTTING TIME (SECONDS) | % INHIBITION OF rhTF FUNCTION |
|---|---|---|---|---|
| 0.0048 | 0<br>1.61<br>3.23 | 0<br>335.4<br>670.8 | 102.3<br>114.3<br>121.3 | 0<br>31.3<br>45.8 |
| 0.023 | 0<br>1.61<br>3.23<br>6.45 | 0<br>70.0<br>140.0<br>280.4 | 77.6<br>85.3<br>91.1<br>99.6 | 0<br>52.2<br>65.2<br>73.9 |
| 0.092 | 0<br>3.23<br>6.45<br>12.90 | 0<br>35.1<br>70.1<br>140.2 | 49.3<br>65.8<br>88.5<br>113.3 | 0<br>65.2<br>90.2<br>95.7 |
| 0.46 | 0<br>6.45<br>12.90<br>32.30 | 0<br>14.0<br>28.0<br>70.2 | 32.6<br>52.7<br>80.2<br>117.9 | 0<br>82.4<br>96.7<br>99.3 |
| 2.30 | 0<br>16.10<br>32.30<br>64.50 | 0<br>7.0<br>14.0<br>28.0 | 23.9<br>47.1<br>95.2<br>115.3 | 0<br>94.4<br>99.7<br>99.9 |
| 11.52 | 0<br>16.10<br>32.30<br>64.50<br>161.30 | 0<br>1.4<br>2.8<br>5.6<br>14.0 | 22.2<br>30.2<br>46.0<br>87.6<br>114.0 | 0<br>93.4<br>98.8<br>99.9<br>100.0 |

FIG. 5

| H36.D2 CONCENTRATION (ng) | % INHIBITION<br>CELLS (TF/FVII) AND H36.D2 PREINCUBATED PRIOR TO FX ADDITION | % INHIBITION<br>FX AND H36.D2 ARE ADDED SIMULTANEOUSLY TO CELLS (TF/FVII) |
|---|---|---|
| 0 | 0 | 0 |
| 50 | 88 | nd |
| 100 | 92 | nd |
| 200 | 97 | nd |
| 800 | nd | 76 |
| 1600 | nd | 78 |
| 3200 | nd | 92 |

FIG. 7

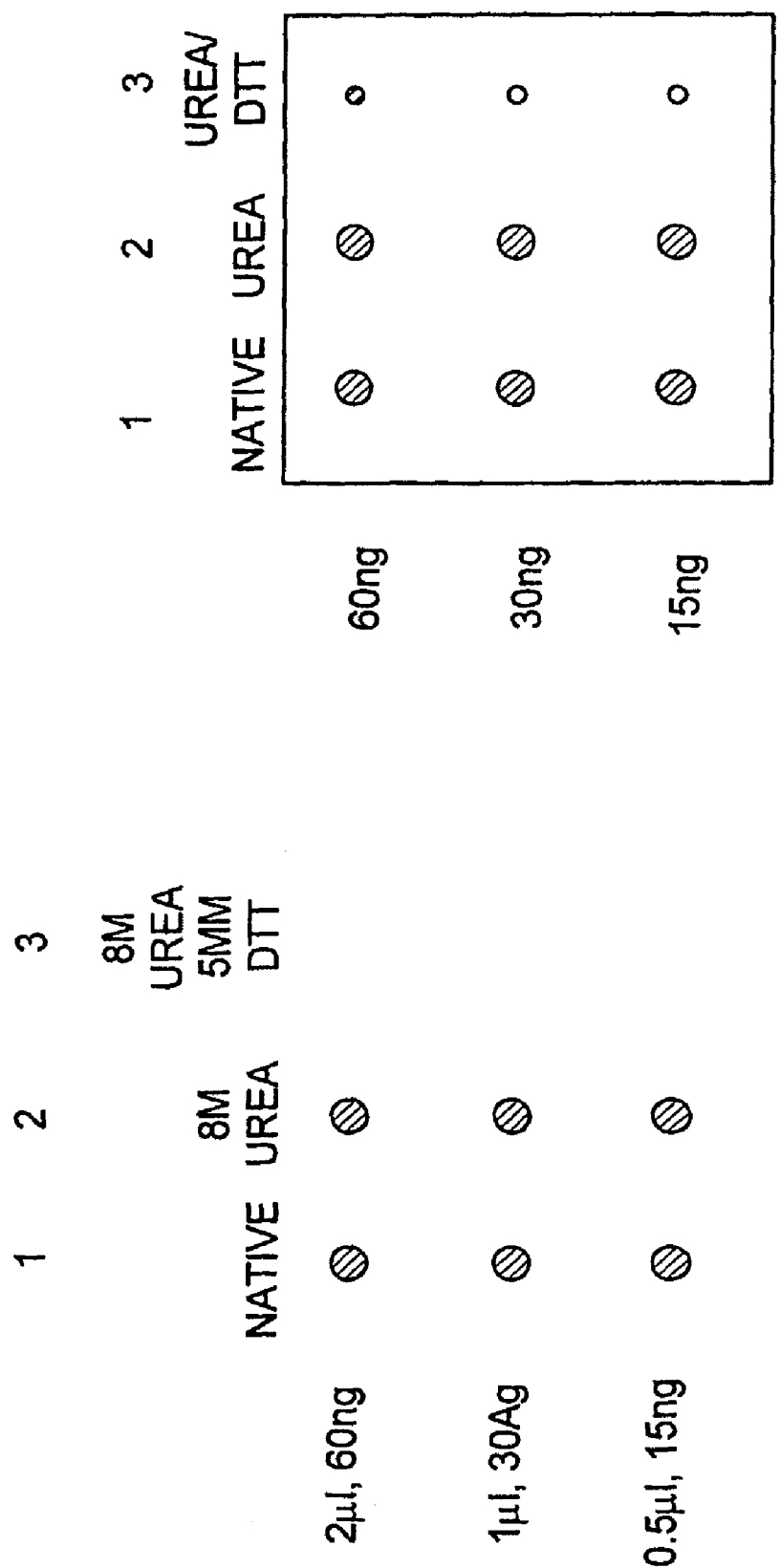

Humanization of anti-Tissue Factor Antibody cH36

Sequences of Partially and Fully Humanized Light Chain (LC) Variable Regions Light Chain (LC) FR Sequences

```
FR1 (23 AA)                 FR2 (14 AA)          FR3 (32 AA)                         FR4 (10 AA)    Names
1          10       20    35           47 57  60                70      80     86   98        107
DIQMTQSPASQSASLGESVTITC   WYQQKPGKSPQLIY   GVPSRFSGSGSGTKFSFKISSLQAEDFVNYYC   FGAGTKLELK   cH36-LC
DIQMTQSPASQSASLGESVTITC   WYQQKPGKSPQLIY   GVPSRFSGSGSGTKFSFKISSLQAEDFVNYYC   FGAGTKLEIK   LC-03
DIQMTQSPASQSASLGESVTITC   WYLQKPGKSPQLIY   GVPS FSGSGSGTKFSFKISSLQAEDFVNYYC   FGAGTKLEIK   LC-04
DIQMTQSPASLSASVGDRVTITC   WYLQKPGKSPQLIY   GVPSRFSGSGSGTKFSFKISSLQAEDFVNYYC   FGQGTKLEIK   LC-05
DIQMTQSPASQSASLGESVTITC   WYLQKPGKSPQLIY   GVPSRFSGSGSGTKFSFKISSLQAEDFVNYYC   FGQGTKLEIK   LC-06
DIQMTQSPASQSASLGESVTITC   WYLQKPGKSPQLIY   GVPSRFSGSGSGTDFSFTISSLQPEDFVNYYC   FGQGTKLEIK   LC-07
DIQMTQSPASQSASLGESVTITC   WYLQKPGKSPQLIY   GVPSRFSGSGSGTDFSFTISSLQPEDFATYYC   FGQGTKLEIK   LC-08
DIQMTQSPASLSASVGDRVTITC   WYLQKPGKSPQLIY   GVPSRFSGSGSGTDFSFTISSLQPEDFATYYC   FGQGTKLEIK   LC-09
DIQMTQSPASLSASVGDRVTITC   WYLQKPGKSPQLIY   GVPSRFSGSGSGTDFSFTISSLQPEDFANYYC   FGQGTKLEIK   LC-10
DIQMTQSPASLSASVGDRVTITC   WYLQKPGKSPQLIY   GVPSRFSGSGSGTKFSFTISSLQPEDFANYYC   FGQGTKLEIK   LC-11
DIQMTQSPASLSASVGDRVTITC   WYLQKPGKSPQLIY   GVPSRFSGSGSGTKFSFTISSLQPEDFANYYC   FGQGTKLEIK   LC-12
DIQMTQSPASLSASVGDRVTITC   WYLQKPGQSPQLIY   GVPSRFSGSGSGTKFSFTISSLQPEDFANYYC   FGQGTKLEIK
```

FIG. 12A

Light Chain CDR Sequnces of cH36

```
CDR1 (11 AA)              CDR2 (7 AA)         CDR3 (9 AA)
24           34           50         56       89           97
IASQTIDTWLA               AATNLAD             QQVYSSPFT
```

FIG. 12B                   FIG. 12C              FIG. 12D

Sequences of Partially and Fully Humanized Heavy Chain (HC) Variable Regions

Heavy Chain (HC) FR Sequences

```
FR1 (30 AA)                         FR2 (14 AA)         FR3 (32 AA)                              FR4 (11 AA)
1          10         20       29   36           44     67         75         85         95      107        117    Names
EIQLQQSGPELVKPGASVQVSCKTSGYSFT      WVRQSHGKSLEWIG      KATLTVDKSSTTAFMHLNSLTSDDSAVYFCAR         WGQGTTLTVSS    cH36-HC
QIQLQQSGPELVKPGASVQVSCKTSGYSFT      WVRQSHGKSLEWIG      KATLTVDKSSTTAFMHLNSLTSDDSAVYFCAR         WGQGTTVTVSS    HC-01
QIQLQQSGPELVKPGASVQVSCKTSGYSFT      WVRQSPGKGLEWIG      KATLTVDKSSTTAFMHLNSLTSDDSAVYFCAR         WGQGTTVTVSS    HC-02
QIQLQQSGPELVKPGASVQVSCKTSGYSFT      WVRQSPGKGLEWIG      KATLTVDKSSTTAFMHLNSLRSEDTAVYFCAR         WGQGTTVTVSS    HC-03
QIQLQQSGPELVKPGASVQVSCKTSGYSFT      WVRQSPGKGLEWIG      KATLTVDKSTSTAFMELSSLRSEDTAVYFCAR         WGQGTTVTVSS    HC-04
QIQLQQSGPELVKPGASVQVSCKTSGYSFT      WVRQSPGKGLEWIG      KATLTVDKSTSTAYMELSSLRSEDTAVYFCAR         WGQGTTVTVSS    HC-05
QMQLQQSGGGELVKPGASVRVSCKASGYSFT     WVRQSPGKGLEWIG      KATLTVDKSTSTAYMELSSLRSEDTAVYFCAR         WGQGTTVTVSS    HC-06
QIQIVQSGGGELVKPGASVRVSCKASGYSFT     WVRQSPGKGLEWIG      KATLTVDKSTSTAYMELSSLRSEDTAVYFCAR         WGQGTTVTVSS    HC-07
QIQIVQSGGEVKPGASVRVSCKASGYSFT       WVRQSPGKGLEWIG      KATLTVDKSTSTAYMELSSLRSEDTAVYFCAR         WGQGTTVTVSS    HC-08
QIQIVQSGGGEVKPGASVRVSCKASGYSFT      WVRQSPGKGLEWIG      KATLTVDKSTSTAYMELSSLRSEDTAVYFCAR         WGQGTTVTVSS    HC-08R1
QIQIVQSGPELVKPGASVRVSCKASGYSFT      WVRQSPGKGLEWIG      KATLTVDKSTSTAYMELSSLRSEDTAVYFCAR         WGQGTTVTVSS    HC-11
QIQIVQSGPELVKPGASVRVSCKASGYSFT      WVRQSPGKGLEWIG      KATLTVDKSTSTAYMELSSLRSEDTAVYFCAR         WGQGTTVTVSS    HC-12
QIQIVQSGPELKPGASVRVSCKASGYSFT       WVRQSPGKGLEWIG      KATLTVDKSTSTAYMELSSLRSEDTAVYFCAR         WGQGTTVTVSS    HC-09
QIQIVQSGPEVVKPGASVRVSCKASGYSFT      WVRQSPGKGLEWIG      KATLTVDKSTSTAYMELSSLRSEDTAVYFCAR         WGQGTTVTVSS    HC-10
```

FIG. 13A

Heavy Chain CDR Sequences

```
CDR1 (5 AA)     CDR2 (17 AA)
31    35        50                          66
D Y N V Y       Y I D P Y N G I T T Y D Q N F K G
D Y N V Y       Y I D P Y N G I T T Y D Q N L K G
```

FIG. 13B                FIG. 13C

```
CDR3 (8 AA)
99            106               Names
D V T T A L D F                 cH36
D V T T A L D F                 HC-08
```

FIG. 13D hOAT (IgG1) CONSTANT REGIONS SEQUENCES

SEQUENCES OF LC CONSTANT:

RTVAAPSVFIFPPSDEQLKSGTASVVCLLNNFYPREAKVQWKVDNALQSGNSQESVTEQDSKDSTYSLSSTLTLSKADYEKH
KVYACEVTHQGLSSPVTKSFNRGEC

FIG. 14A

SEQUENCES OF HC CONSTANT:

EFASTKGPSVFPLAPSSKSTSGGTAALGCLVKDYFPEPVTVSWNSGALTSGVHTFPAVLQSSGLYSLSSVVTVPSSSLGTQTYIC
NVNHKPSNTKVDKKVEPKSCDKTHTCPPCPAPELLGGPSVFLFPPKPKDTLMISRTPEVTCVVVDVSSHEDPEVKFNWYVDGVEV
HNAKTKPREEQYNSTYRVVSVLTVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHEALHNHYTQKSLSLSPGK

FIG. 14B hFAT (IgG1) CONSTANT REGION SEQUENCES

SEQUENCES OF LC CONSTANT:

RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

FIG. 15A

SEQUENCES OF HC CONSTANT:

EFASTKGPSVFPLAPCSRSTSESTAALGCLVKDYFPEPVTVSWNSGALTSGVHTFPAVLQSSGLYSLSSVVTVPSSSLGTKTY
TCNVDHKPSNTKVDKRVESKYGPPCPSCPAPEFLGGPSVFLFPPKPKDTLMISRTPEVTCVVVDVSQEDPEVQFNWYVDGV
EVHNAKTKPREEQFNSTYRVVSVLTVLHQDWLNGKEYKCKVSNKGLPSSIEKTISKAKGQPREPQVYTLPPSQEEMTKNQVSL
TCLVKGFYPSDDIAVEWESNGQPENNYKTTPPVLDSDGSFFLYSRLTVDKSRWQEGNVFSCSVMHEALHNHYTQKSLSLSLGK

FIG. 15B

ANTI-TISSUE FACTOR ANTIBODIES AND METHODS OF USE THEREOF

CROSS-REFERENCE TO RELATED APPLICATIONS

The present application is a continuation of U.S. patent application Ser. No. 11/122,622, filed on May 5, 2005, now abandoned which is a continuation of U.S. patent application Ser. No. 09/990,586, filed on Nov. 21, 2001, now abandoned which claims priority to U.S. Provisional Application No. 60/343,306, filed on Oct. 29, 2001. The disclosures of each are herein incorporated by reference in their entirety.

BACKGROUND OF THE INVENTION

1. Field of the Invention

The present invention relates to novel human tissue factor antibodies and methods of using the antibodies to inhibit tissue factor-related functions such as blood coagulation, angiogenesis, tumor metastasis, and inflammation. In particular, the invention relates to novel antibodies that can specifically bind native human tissue factor with high affinity and prevent factor X or factor IX binding and activation. The antibodies of the invention are useful for a variety of applications, particularly for reducing blood coagulation in vivo.

2. Background

Blood clotting assists homeostasis by minimizing blood loss. Generally, blood clotting requires vessel damage, platelet aggregation, activation of coagulation factors and inhibition of fibrinolysis. The coagulation factors act through a cascade that relates the vessel damage to formation of a blood clot (see generally L. Stryer, *Biochemistry*, 3rd Ed, W.H. Freeman Co., New York; and A. G. Gilman et al., *The Pharmacological Basis of Therapeutics*, 8th Edition, McGraw Hill Inc., New York, pp. 1311-1331).

There is general agreement that factor X (FX) activation to factor Xa (FXa) (or factor IX activation to factor IXa) is a critical step in the blood coagulation process. Generally, FX (or FIX) is converted to FXa (or FIXa) by binding a catalytically active complex that includes "tissue factor" (TF). TF is a controllably-expressed cell membrane protein that binds factor VII/VIIa to produce the catalytically active complex (TF:FVIIa). A blood clot follows FXa-mediated (or FIXa) activation of prothrombin. Blood clotting can be minimized by inactivation of TF to non-native forms which cannot optimally produce the TF:FVIIa complex. Excessive activation of the coagulation cascade through formation of FXa (or FIxa) is believed to contribute to various thromboses including restenosis.

Thrombosis may be associated with invasive medical procedures such as cardiac surgery (e.g. angioplasty), abdominothoracic surgery, arterial surgery, peripheral vascular bypass grafts, deployment of an implementation (e.g., a stent or catheter), or endarterectomy. Further, thrombosis may accompany various thromboembolic disorders and coagulopathies such as stroke, pulmonary embolism (e.g., atrial fibrillation with embolization), coronary artery disease or acute coronary syndromes (e.g., unstable angina or myocardial infarction), atherosclerosis or other thrombo-occlusive disorders, deep vein thrombosis and disseminated intravascular coagulation, respectively. Manipulation of body fluids can also result in an undesirable thrombus, particularly in blood transfusions or fluid sampling, as well as procedures involving extracorporeal circulation (e.g., cardiopulmonary bypass surgery) and renal dialysis.

Anti-coagulants are frequently used to alleviate or avoid blood clots associated with thrombosis. Blood clotting often can be minimized or eliminated by administering a suitable anti-coagulant or mixture thereof, including one or more of a coumarin derivative (e.g., warfarin, Coumadin or dicumarol) or a charged polymer (e.g., heparin, low molecular weight heparin, hirudin or hirulog) or anti-platelet agents (e.g., ReoPro, Integrilin, Aggrestat, Plavix, Ticlid or aspirin). See e.g., Gilman et al., supra, R. J. Beigering et al., *Ann. Hematol.*, 72:177 (1996); J. D. Willerson, *Circulation*, 94:866 (1996).

However, use of anti-coagulants is often associated with side effects such as hemorrhaging, re-occlusion, "white-clot" syndrome, irritation, birth defects, thrombocytopenia and hepatic dysfunction. Long-term administration of anti-coagulants can particularly increase risk of life-threatening illness (see e.g., Gilman et al., supra).

Certain antibodies with anti-platelet activity have also been used to alleviate various thromboses. For example, ReoPro®™ is a therapeutic antibody fragment that is routinely administered to alleviate various thromboembolic disorders such as those arising from angioplasty, myocardial infarction, unstable angina and coronary artery stenoses. Additionally, ReoPro® can be used as a prophylactic to reduce the risk of myocardial infarction and angina (J. T. Willerson, *Circulation*, 94:866 (1996); M. L. Simmons et al., *Circulation*, 89:596 (1994)).

Certain anti-coagulant antibodies are also known. Particularly, certain TF-binding antibodies have been reported to inhibit blood coagulation, presumably by interfering with assembly of a catalytically active TF:FVIIa complex (see e.g., Jeske et al., *SEM in THROM. and HEMO*, 22:213 (1996); Ragni et al., *Circulation*, 93:1913 (1996); European Patent No. 0 420 937 B1; W. Ruf et al., *Throm. Haemosp.*, 66:529 (1991); M. M. Fiorie et al., *Blood*, 8:3127 (1992)).

However, current TF-binding antibodies exhibit significant disadvantages which can minimize their suitably as anti-coagulants. For example, current TF-binding antibodies do not exhibit sufficient binding affinity for optimal anti-coagulant activity. Accordingly, for many thrombotic conditions, to compensate for such ineffective binding affinities, unacceptably high antibody levels must be administered to minimize blood coagulation.

It would thus be desirable to have an anti-coagulant antibody that binds native human TF with high affinity and selectivity to thereby inhibit undesired blood coagulation and the formation of blood clots. It would be further desirable to have such an anti-coagulant antibody that prevents the binding of factor X (or factor IX) to TF:FVIIa complex.

SUMMARY OF THE INVENTION

We have now discovered antibodies that provide superior anti-coagulant activity by binding native human TF with high affinity and specificity. Antibodies of the invention can effectively inhibit blood coagulation in vivo. Antibodies of the invention can bind native human TF, either alone or present in a TF:FVIIa complex, effectively preventing factor X (or factor IX) binding to TF or that complex, and thereby reducing blood coagulation.

Preferred antibodies of the invention are monoclonal and specifically bind a conformational epitope predominant to native human TF, which epitope provides a site for the unexpectedly strong antibody binding. Indeed, preferred antibodies of the invention bind to native human TF at least about 5 times greater, more typically at least about ten times greater than the binding affinity exhibited by prior anti-coagulant antibodies. Additionally, preferred antibodies of the invention are selective for native human TF, and do not substantially bind non-native or denatured TF. H36.D2.B7 (secreted by hybridoma ATCC HB-12255 and often referred to as H36) is an especially preferred antibody of the invention.

Preferred antibodies of the invention bind TF so that FX (or FIX) does not effectively bind to the TF:FVIIa complex whereby FX (or FIX) is not effectively converted to its activated form (FXa or FIXa). Preferred antibodies of the invention can inhibit TF function by effectively blocking FX (or FIX) binding or access to TF molecules. See, for instance, the results of Example 3 which follows.

Preferred antibodies of the invention also do not significantly inhibit the interaction or binding between TF and factor VIIa, or inhibit activity of a TF:FVIIa complex with respect to materials other than FX and Factor IX. See, for instance, the results of Example 4 which follows.

The invention also provides nucleic acids that encode antibodies of the invention. Nucleic acid and amino acid sequences (SEQ ID NOS: 1-4) of variable regions of H36.D2.B7 are set forth in FIGS. 1A and 1B of the drawings.

In preferred aspects, the invention provides methods for inhibiting blood coagulation and blood clot formation, and methods for reducing human TF levels.

In general, antibodies of the invention will be useful to modulate virtually any biological response mediated by FX (or FIX) binding to TF or the TF:FVIIa complex, including blood coagulation as discussed above, inflammation, tumor angiogenesis and metastasis, and other disorders.

Antibodies of the invention are particularly useful to alleviate various thromboses, particularly to prevent or inhibit restenosis, or other thromboses following an invasive medical procedure such as arterial or cardiac surgery (e.g., angioplasty). Antibodies of the invention also can be employed to reduce or even effectively eliminate thrombotic occlusion arising from activation of blood coagulation in such non-surgical cardiovascular conditions including but not limited to coronary artery disease, acute coronary syndromes (e.g., unstable angina and myocardial infarction) and atherosclerosis. Antibodies of the invention also can be employed to reduce or even effectively eliminate blood coagulation arising from use of medical implementation (e.g., a catheter, stent or other medical device). Preferred antibodies of the invention will be compatible with many anti-coagulant, anti-platelet and thrombolytic compositions, thereby allowing administration in a cocktail format to boost or prolong inhibition of blood coagulation.

Antibodies of the invention also can be employed as an anti-coagulant in extracorporeal circulation of a mammal, particularly a human subject. In such methods, one or more antibodies of the invention is administered to the mammal in an amount sufficient to inhibit blood coagulation prior to or during extracorporeal circulation such as may be occur with cardiopulmonary bypass surgery, organ transplant surgery or other prolonged surgeries.

Antibodies of the invention also can be used as a carrier for drugs, particularly pharmaceuticals targeted for interaction with a blood clot such as strepokinase, tissue plasminogen activator (t-PA) or urokinase. Similarly, antibodies of the invention can be used as a cytotoxic agent by conjugating a suitable toxin to the antibody. Conjugates of antibodies of the invention also can be used to reduce tissue factor levels in a mammal, particularly a human, by administering to the mammal an effective amount of an antibody of the invention which is covalently linked to a cytotoxic agent or an effector molecule to provide complement-fixing ability and antibody-dependent cell-mediated cytotoxicity, whereby the antibody conjugate contacts cells expressing tissue factor to thereby reduce tissue factor levels in the mammal.

Antibodies of the invention also can be employed in in vivo diagnostic methods including in vivo diagnostic imaging of native human TF.

Antibodies of the invention also can be used in in vitro assays to detect native TF in a biological sample including a body fluid (e.g., plasma or serum) or tissue (e.g., a biopsy sample). More particularly, various heterogeneous and homogeneous immunoassays can be employed in a competitive or non-competitive format to detect the presence and preferably an amount of native TF in the biological sample.

Such assays of the invention are highly useful to determine the presence or likelihood of a patient having a blood coagulation or a blood clot. That is, blood coagulation is usually accompanied by and the result of TF expression on cell surfaces such as monocytes, macrophages, and endothelial cells lining the vasculature. Thus, the detection of TF in a body fluid sample by an assay of the invention will be indicative of blood coagulation.

Antibodies of the invention also can be used to prepare substantially pure native TF, particularly native human TF, from a biological sample. Antibodies of the invention also can be used for detecting and purifying cells which express native TF.

Antibodies of the invention also can be employed as a component of a diagnostic kit, e.g. for detecting and preferably quantitating native TF in a biological sample.

The invention also provides humanized antibodies that bind specifically to human tissue factor (TF) to form a complex. In a preferred embodiment, blood factor X or factor IX binding to the complex is significantly inhibited. Preferably, the humanized antibody includes at least one murine complementarity determining region (CDR), preferably one, two, three or four of such murine CDRs. Further provided are TF binding fragments of such humanized antibodies.

In another aspect, the invention provides methods of inhibiting blood coagulation in a mammal that include administering to the mammal an effective amount of the humanized antibody or fragment thereof that binds specifically to human tissue factor (TF) to form a complex. A preferred antibody for use in the method significantly reduces factor X or factor IX binding to the complex. Preferred methods further include forming a specific complex between the antibody and the TF or TF:FVIIa complex to inhibit the blood coagulation.

The invention also provides methods of inhibiting blood coagulation in a mammal that include administering to the mammal, an effective amount of a humanized antibody or fragment thereof comprising at least one murine complementarity determining region (CDR). A preferred humanized antibody for use with the method binds specifically to human tissue factor (TF) to form a complex. Preferably, factor X or factor IX binding to the complex is significantly reduced. Preferred methods further include forming a specific complex between the antibody and the TF to inhibit the blood coagulation.

Other aspects of the invention are discussed infra.

BRIEF DESCRIPTION OF THE DRAWINGS

FIGS. 1A and 1B shows the nucleic acid (SEQ ID NOS: 1 and 3) and amino acid (SEQ ID NOS:2 and 4) sequences of light chain and heavy chain variable regions of H36.D2.B7 with hypervariable regions (CDRs or Complementarity Determining Regions) underlined (single underline for nucleic acid sequences and double underline for amino acid sequences) (SEQ ID NOS: 5-10, respectively, in order of appearance).

FIG. 2 shows association ($K_a$) and disassociation ($K_d$) constants of anti-tissue factor antibodies as determined by ELISA or BIACore analysis.

FIG. 3 shows inhibition of TF:FVIIa complex mediated FX activation by pre-incubation with anti-tissue factor antibodies.

FIG. 4 shows inhibition of TF:FVIIa activity toward the FVIIa-specific chromogenic substrate S-2288 by anti-tissue factor antibodies.

FIG. 5 shows the capacity of the H36 antibody to increase prothrombin time (PT) in a TF-initiated coagulation assay.

FIG. 6A: H36 was pre-incubated with the TF:FVIIa complex prior to adding FX. FIG. 6B: H36, TF:FVIIa and FX were added simultaneously.

FIG. 7 shows inhibition of TF:FVIIa activity by the H36 antibody in a J-82 cell activation assay.

FIGS. 8A and 8B are representations of dot blots showing that the H36 antibody binds a conformational epitope on rhTF. Lane 1—native rHTF, Lane 2—native rhTF treated with 8M urea, Lane 3—native rHTF treated with 8M urea and 5 mM DTT. In FIG. 8A, the blot was exposed for approximately 40 seconds, whereas in FIG. 8B, the blot was exposed for 120 seconds.

FIGS. 12A-D are drawings showing sequences of partially and fully humanized light chain (LC) variable regions. FIG. 12A sequences correspond to SEQ ID NOS: 72-82, and 103-115, respectively, in order of appearance. Light chain CDR sequences CDR sequences of cH36 are shown in FIGS. 12B-D (SEQ ID NO: 116, SEQ ID NO: 6 and SEQ ID NO: 7, respectively). Sequence named "LC-09" (SEQ ID NO: 79) is representative of a fully humanized LC framework region.

FIGS. 13A-D are sequences of partially and fully humanized heavy chain (LC) variable regions. FIG. 13A sequences correspond to SEQ ID NOS: 83-96, and 117-133, respectively, in order of appearance. Heavy chain CDR sequences for cH36 and HC-08 are shown in FIGS. 13B-D (SEQ ID NO: 134, SEQ ID NOS: 9 and 101, and SEQ ID NO: 10, respectively, in order of appearance). Sequence named "HC-08" (SEQ ID NO: 91) is fully humanized HC framework region.

FIGS. 14A-B (SEQ ID NOS: 97 and 98, respectively, in order of appearance) are drawings showing humanized IgG one anti-tissue factor antibody (hOAT (IgG1) constant regions.

FIGS. 15A-B (SEQ ID NOS: 99-100, respectively, in order of appearance) are drawings showing humanized IgG four anti-tissue factor antibody (hFAT) (IgG4) constant regions.

DETAILED DESCRIPTION OF THE INVENTION

Figure 6A:
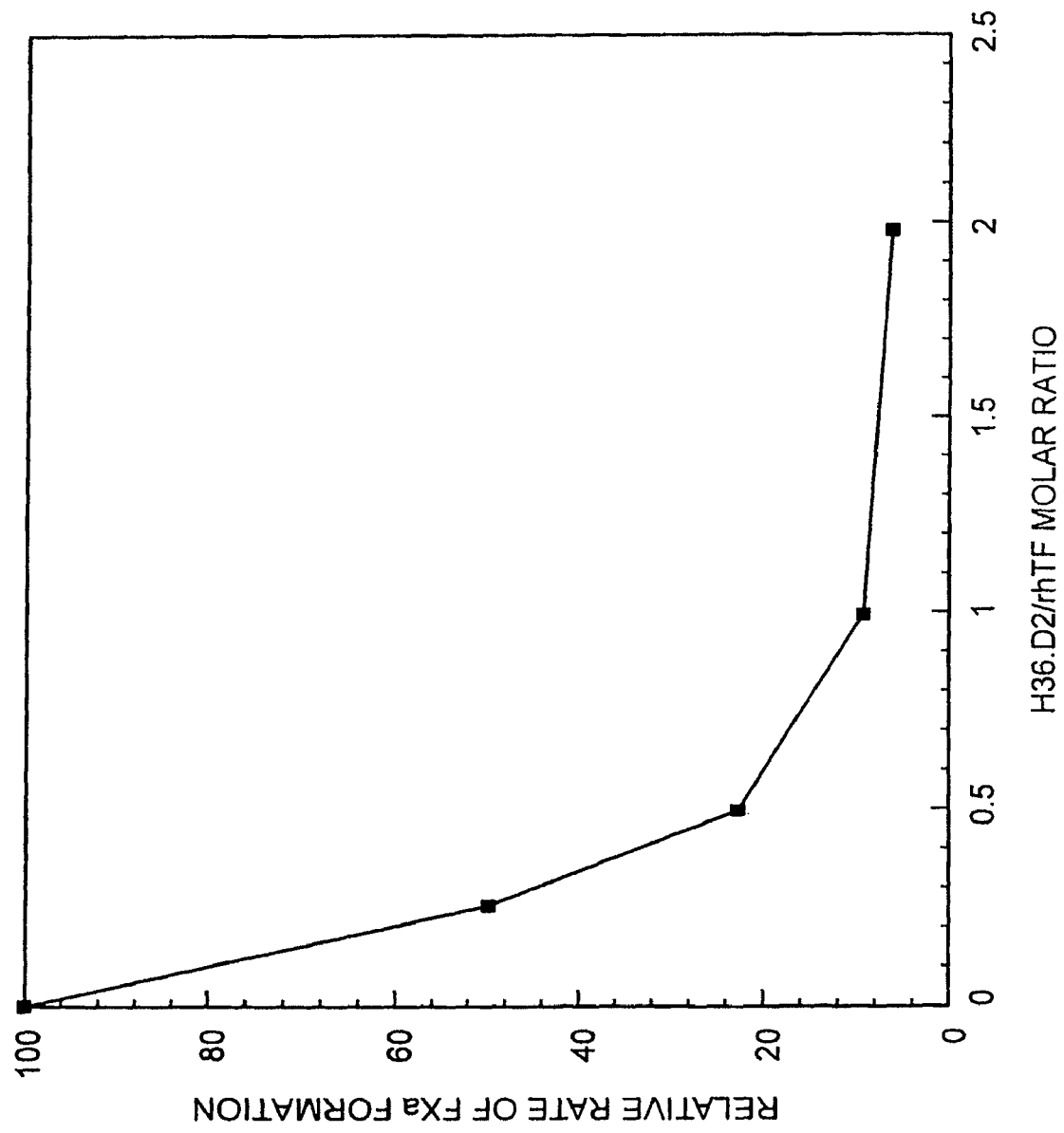
FIGS. 6A and 6B graphically show the relationship between FXa formation and molar ratio of the H36 antibody and rHTF.

As discussed above, preferred antibodies of the invention exhibit substantial affinity for native human TF. In particular, preferred antibodies of the invention exhibit an association constant ($K_a$, $M^{-1}$) for native human TF of at least about $1 \times 10^8$ as determined by surface plasmon analysis (particularly, BIACore analysis in accordance with the procedures of Example 1 which follows), more preferably at least about $5 \times 10^8$ as determined by surface plasmon analysis, still more preferably a $K_a$ ($K_a$, $M^{-1}$) for native human TF of at least about $1 \times 10^{10}$ as determined by surface plasmon resonance analysis. Such substantial binding affinity of antibodies of the invention contrast sharply from much lower binding affinities of previously reported antibodies.

In this regard, a quite low of effective concentration of an antibody of the invention can be employed, e.g. a relatively low concentration of antibody can be employed to inhibit TF function as desired (e.g. at least about 95, 98 or 99 percent inhibition) in an in vitro assay such as described in Example 3 which follows.

The preferred antibodies are also highly specific for native human TF, and preferably do not substantially bind with non-native TF. Preferred antibodies do not substantially bind non-native TF or other immunologically unrelated molecules as determined, e.g. by standard dot blot assay (e.g. no or essentially no binding to non-native TF visually detected by such dot blot assay). References herein to "non-native TF" mean a naturally-occurring or recombinant human TF that has been treated with a chaotropic agent so that the TF is denatured. Typical chaotropic agents include a detergent (e.g. SDS), urea combined with dithiothreotol or β-mercaptoethanol; guanidine hydrochloride and the like. The H36, H36.D2 or H36.D2.B7 antibody does not substantially bind to such non-native TF. See, for instance, the results of Example 8 which follows and is a dot blot assay.

As discussed above, preferred antibodies of the invention also bind with TF so that FX (or FIX) does not effectively bind to the TF:FVIIa complex whereby FX (or FIX) is not effectively converted to its activated form (FXa or FIXa). Particularly preferred antibodies of the invention will strongly inhibit FX activation by a TF:FVIIa complex, e.g. an inhibition of at least about 50%, more preferably at least about 80%, and even more preferably at least about 90% or 95%, even at low TF concentrations such as less than about 1.0 nM TF, or even less than about 0.20 nM or 0.10 nM TF, as determined by a standard in vitro binding assay such as that of Example 3 which follows and includes contacting FX (or FIX) with a TF: FVIIa complex both in the presence (i.e. experimental sample) and absence (i.e. control sample) of an antibody of the invention and determining the percent difference of conversion of FX to FXa (or FIX to FIXa) between the experimental and control samples.

Antibodies of the invention are preferably substantially pure when used in the disclosed methods and assays. References to an antibody being "substantially pure" mean an antibody or protein which has been separated from components which naturally accompany it. For example, by using standard immunoaffinity or protein A affinity purification techniques, an antibody of the invention can be purified from a hybridoma culture by using native TF as an antigen or protein A resin. Similarly, native TF can be obtained in substantially pure form by using an antibody of the invention with standard immunoaffinity purification techniques. Particularly, an antibody or protein is substantially pure when at least 50% of the total protein (weight % of total protein in a given sample) is an antibody or protein of the invention. Preferably the antibody or protein is at least 60 weight % of the total protein, more preferably at least 75 weight %, even more preferably at least 90 weight %, and most preferably at least 98 weight % of the total material. Purity can be readily assayed by known methods such as SDS (PAGE) gel electrophoresis, column chromatography (e.g., affinity chromatography) or HPLC analysis.

The nucleic acid (SEQ ID NOS: 1 and 3) and amino acid (SEQ ID NOS: 2 and 4) sequences of a preferred antibody of the invention (H36.D2.B7) are shown in FIGS. 1A and 1B of the drawings. SEQ ID NOS: 1 and 2 are the nucleic acid and amino acid respectively of the light chain variable region, and SEQ ID NOS: 3 and 4 are the nucleic acid and amino acid respectively of the heavy chain variable region, with hypervariable regions (CDRs or Complementarity Determining Regions) underlined in all of those sequences.

Additional preferred antibodies of the invention will have substantial amino acid sequence identity to either one or both of the light chain or heavy sequences shown in FIGS. 1A and 1B. More particularly, preferred antibodies include those that have at least about 70 percent homology (amino acid sequence identity) to SEQ ID NOS: 2 and/or 4, more preferably about 80 percent or more homology to SEQ ID NOS: 2 and/or 4, still more preferably about 85, 90 or 95 percent or more homology to SEQ ID NOS: 2 and/or 4.

Preferred antibodies of the invention will have high amino acid sequence identity to hypervariable regions (shown with double underlining in FIGS. 1A and 1B) of SEQ ID NOS: 2 and 4). Especially preferred antibodies of the invention will have one, two or three hypervariable regions of a light chain variable region that have high sequence identity (at least 90% or 95% amino acid sequence identity) to or be the same as one, two or three of the corresponding hypervariable regions of the light chain variable region of H36.D2.B7 (those hypervariable regions shown with underlining in FIG. 1A and are the following: 1) LASQTID (SEQ ID NO: 5); 2) AATNLAD (SEQ ID NO: 6); and 3) QQVYSSPFT (SEQ ID NO: 7)).

Especially preferred antibodies of the invention also will have one, two or three hypervariable regions of a heavy chain variable region that have high sequence identity (at least 90% or 95% amino acid sequence identity) to or be the same as one, two or three of the corresponding hypervariable regions of the heavy chain variable region of H36.D2.B7 (those hypervariable regions shown with underlining in FIG. 1B and are the following: 1) TDYNVY (SEQ ID NO: 8); 2) YIDPYNGITIYDQNFKG (SEQ ID NO: 9); and 3) DVTTALDF (SEQ ID NO: 10).

Nucleic acids of the invention preferably are of a length sufficient (preferably at least about 100, 200 or 250 base pairs) to bind to the sequence of SEQ ID NO: 1 and/or SEQ ID NO: 3 under the following moderately stringent conditions (referred to herein as "normal stringency" conditions): use of a hybridization buffer comprising 20% formamide in 0.8M saline/0.08M sodium citrate (SSC) buffer at a temperature of 37° C. and remaining bound when subject to washing once with that SSC buffer at 37° C.

More preferably, nucleic acids of the invention (preferably at least about 100, 200 or 250 base pairs) will bind to the sequence of SEQ ID NO: 1 and/or SEQ ID NO: 3 under the following highly stringent conditions (referred to herein as "high stringency" conditions): use of a hybridization buffer comprising 20% formamide in 0.9M saline/0.09M sodium citrate (SSC) buffer at a temperature of 42° C. and remaining bound when subject to washing twice with that SSC buffer at 42° C.

Nucleic acids of the invention preferably comprise at least 20 base pairs, more preferably at least about 50 base pairs, and still more preferably a nucleic acid of the invention comprises at least about 100, 200, 250 or 300 base pairs.

Generally preferred nucleic acids of the invention will express an antibody of the invention that exhibits the preferred binding affinities and other properties as disclosed herein.

Preferred nucleic acids of the invention also will have substantial sequence identity to either one or both of the light chain or heavy sequences shown in FIGS. 1A and 1B. More particularly, preferred nucleic acids will comprise a sequence that has at least about 70 percent homology (nucleotide sequence identity) to SEQ ID NOS: 1 and/or 3, more preferably about 80 percent or more homology to SEQ ID NOS: 1 and/or 3, still more preferably about 85, 90 or 95 percent or more homology to SEQ ID NOS: 1 and/or 3.

Particularly preferred nucleic acid sequences of the invention will have high sequence identity to hypervariable regions (shown with underlining in FIGS. 1A and 1B) of SEQ ID NOS: 1 and 3). Especially preferred nucleic acids include those that code for an antibody light chain variable region and have one, two or three sequences that code for hypervariable regions and have high sequence identity (at least 90% or 95% nucleotide sequence identity) to or be the same as one, two or three of the sequences coding for corresponding hypervariable regions of H36.D2.B7 (those hypervariable regions shown with underlining in FIG. 1A and are the following:

1) CTGGCAAGTCAGACCATTGAT; (SEQ ID NO: 11)

2) GCTGCCACAACTTGGCAGAT; (SEQ ID NO: 12)
and

3) CAACAAGTTTACAGTTCT CCATTCACGT). (SEQ ID NO: 13)

Especially preferred nucleic acids also code for an antibody heavy chain variable region and have one, two or three sequences that code for hypervariable regions and have high sequence identity (at least 90% or 95% sequence identity) to or be the same as one, two or three of the sequences coding for corresponding hypervariable regions of H36.D2.B7 (those hypervariable regions shown with underlining in FIG. 1B and are the following:

1) ACTGACTACAACGTGTAC; (SEQ ID NO: 14)

2) TATATTGATCCTTACAATGGTATTACTATCTACGACCAGAACTTCA AGGGC; (SEQ ID NO: 15)
and

3) GATGTGACTACGGCCCTTGACTTC). (SEQ ID NO: 16)

Nucleic acids of the invention are isolated, usually constitutes at least about 0.5%, preferably at least about 2%, and more preferably at least about 5% by weight of total nucleic acid present in a given fraction. A partially pure nucleic acid constitutes at least about 10%, preferably at least about 30%, and more preferably at least about 60% by weight of total nucleic acid present in a given fraction. A pure nucleic acid constitutes at least about 80%, preferably at least about 90%, and more preferably at least about 95% by weight of total nucleic acid present in a given fraction.

Antibodies of the invention can be prepared by techniques generally known in the art, and are typically generated to a purified sample of native TF, typically native human TF, preferably purified recombinant human tissue factor (rhTF). Truncated recombinant human tissue factor or "rhTF" (composed of 243 amino acids and lacking the cytoplasmic domain) is particularly preferred to generate antibodies of the invention. The antibodies also can be generated from an immunogenic peptide that comprises one or more epitopes of native TF that are not exhibited by non-native TF. References herein to "native TF" include such TF samples, including such rhTF. As discussed above, monoclonal antibodies are generally preferred, although polyclonal antibodies also can be employed.

More particularly, antibodies can be prepared by immunizing a mammal with a purified sample of native human TF, or an immunogenic peptide as discussed above, alone or complexed with a carrier. Suitable mammals include typical laboratory animals such as sheep, goats, rabbits, guinea pigs, rats and mice. Rats and mice, especially mice, are preferred for obtaining monoclonal antibodies. The antigen can be administered to the mammal by any of a number of suitable routes such as subcutaneous, intraperitoneal, intravenous, intramuscular or intracutaneous injection. The optimal immunizing interval, immunizing dose, etc. can vary within relatively wide ranges and can be determined empirically based on this disclosure. Typical procedures involve injection of the antigen several times over a number of months. Antibodies are collected from serum of the immunized animal by standard techniques and screened to find antibodies specific for native human TF. Monoclonal antibodies can be produced in cells which produce antibodies and those cells used to generate monoclonal antibodies by using standard fusion techniques for forming hybridoma cells. See G. Kohler, et al., *Nature*, 256:456 (1975). Typically this involves fusing an antibody-producing cell with an immortal cell line such as a myeloma cell to produce the hybrid cell. Alternatively, monoclonal antibodies can be produced from cells by the method of Huse, et al., *Science*, 256:1275 (1989).

One suitable protocol provides for intraperitoneal immunization of a mouse with a composition comprising purified rhTF complex conducted over a period of about two to seven months. Spleen cells then can be removed from the immunized mouse. Serum from the immunized mouse is assayed for titers of antibodies specific for rhTF prior to excision of spleen cells. The excised mouse spleen cells are then fused to an appropriate homogenic or heterogenic (preferably homogenic) lymphoid cell line having a marker such as hypoxanthine-guanine phosphoribosyltransferase deficiency (HGPRT$^-$) or thymidine kinase deficiency (TK$^-$). Preferably a myeloma cell is employed as the lymphoid cell line. Myeloma cells and spleen cells are mixed together, e.g. at a ratio of about 1 to 4 myeloma cells to spleen cells. The cells can be fused by the polyethylene glycol (PEG) method. See G. Kohler, et al., *Nature*, supra. The thus cloned hybridoma is grown in a culture medium, e.g. RPMI-1640. See G. E. More, et al., *Journal of American Medical Association*, 199:549 (1967). Hybridomas, grown after the fusion procedure, are screened such as by radioimmunoassay or enzyme immunoassay for secretion of antibodies that bind specifically to the purified rhTF, e.g. antibodies are selected that bind to the purified rhTF, but not to non-native TF. Preferably an ELISA is employed for the screen. Hybridomas that show positive results upon such screening can be expanded and cloned by limiting dilution method. Further screens are preferably performed to select antibodies that can bind to rhTF in solution as well as in a human fluid sample. The isolated antibodies can be further purified by any suitable immunological technique including affinity chromatography. A hybridoma culture producing the particular preferred H36.D2.B7 antibody has been deposited pursuant to the Budapest Treaty with the American Type Culture Collection (ATCC) at 12301 Parklawn Drive, Rockville, Md., 10852. The hybridoma culture was deposited with the ATCC on Jan. 8, 1997 and was assigned Accession Number ATCC HB-12255.

For human therapeutic applications, it may be desirable to produce chimeric antibody derivatives, e.g. antibody molecules that combine a non-human animal variable region and a human constant region, to thereby render the antibodies less immunogenic in a human subject than the corresponding non-chimeric antibody. A variety of types of such chimeric antibodies can be prepared, including e.g. by producing human variable region chimeras, in which parts of the variable regions, especially conserved regions of the antigen-binding domain, are of human origin and only the hypervariable regions are of non-human origin. See also discussions of humanized chimeric antibodies and methods of producing same in S. L. Morrison, *Science*, 229:1202-1207 (1985); Oi et al., *BioTechniques*, 4:214 (1986); Teng et al., *Proc. Natl. Acad. Sci. U.S.A.*, 80:7308-7312 (1983); Kozbor et al., *Immunology Today*, 4:7279 (9183); Olsson et al., *Meth. Enzymol.*, 9:3-16 (1982). Additionally, transgenic mice can be employed. For example, transgenic mice carrying human antibody repertoires have been created which can be immunized with native human TF. Splenocytes from such immunized transgenic mice can then be used to create hybridomas that secrete human monoclonal antibodies that specifically react with native human TF as described above. See N. Lonberg et al., Nature, 368:856-859 (1994); L. L. Green et al., Nature Genet., 7:13-21 (1994); S. L. Morrison, *Proc. Nat. Acad. Sci. U.S.A.*, 81:6851-6855 (1994).

Nucleic acids which code for the antibodies of the invention also can be prepared by polymerase chain reaction (see primers disclosed in Example 1 which follows). See generally, Sambrook et al., Molecular Cloning (2d ed. 1989). Such nucleic acids also can be synthesized by known methods, e.g. the phosphate triester method (see Oligonucleotide Synthesis, IRL Press (M. J. Gait, ed., 1984)), or by using a commercially available automated oligonucleotide synthesizer. Such a prepared nucleic acid of the invention can be employed to express an antibody of the invention by known techniques. For example, a nucleic acid coding for an antibody of the invention can be incorporated into a suitable vector by known methods such as by use of restriction enzymes to make cuts in the vector for insertion of the construct followed by ligation. The vector containing the inserted nucleic acid sequence, suitably operably linked to a promoter sequence, is then introduced into host cells for expression. See, generally, Sambrook et al., supra. Selection of suitable vectors can be made empirically based on factors relating to the cloning protocol. For example, the vector should be compatible with, and have the proper replicon for the host cell that is employed. Further, the vector must be able to accommodate the inserted nucleic acid sequence. Suitable host cells will include a wide variety of eukaryotic or prokaryotic cells such as *E. coli* and the like.

The molecular weight of the antibodies of the invention will vary depending on several factors such as the intended use and whether the antibody includes a conjugated or recombinantly fused toxin, pharmaceutical, or detectable label or the like. Also the molecular weight will vary depending on nature and extent of post-translational modifications if any (such as glycosylation) to the antibody. The modifications are a function of the host used for expression with *E. coli* producing non-glycosylated antibodies and mammalian cells producing glycosylated antibodies. In general, an antibody of the invention will have a molecular weight of between approximately 20 to 150 kDa. Such molecular weights can be readily are determined by molecular sizing methods such as SDS-PAGE gel electrophoresis followed by protein staining or Western blot analysis.

"Antibody of the invention" or other similar term refers to whole immunoglobulin as well as immunologically active fragments which bind native TF. The immunoglobulins and immunologically active fragments thereof include an antibody-binding site (i.e., epitope capable of being specifically bound by an antibody recognizing native human TF capable of specifically binding native human TF). Exemplary antibody fragments include, for example, Fab, F(v), Fab', F(ab')$_2$ fragments, "half molecules" derived by reducing the disulfide bonds of immunoglobulins, single chain immunoglobulins, or other suitable antigen binding fragments (see e.g., Bird et al., *Science, pp.* 242-424 (1988); Huston et al., *PNAS, (USA)*, 85:5879 (1988); Webber et al., *Mol. Immunol.*, 32:249 (1995)). The antibody or immunologically active fragment thereof may be of animal (e.g., a rodent such as a mouse or a rat), or chimeric form (see Morrison et al., *PNAS*, 81:6851 (1984); Jones et al., *Nature*, pp. 321, 522 (1986)). Single chain antibodies of the invention can be preferred.

Similarly, a "nucleic acid of the invention" refers to a nucleotide sequence which can be expressed to provide an antibody of the invention as such term is specified to mean immediately above.

As discussed above, antibodies of the invention can be administered to a mammal, preferably a primate such as a human, to prevent or reduce thrombotic occlusive disorders attributable to TF-mediated activation of coagulation, typically in a composition including one or more pharmaceutically acceptable non-toxic carriers such as sterile water or saline, glycols such as polyethylene glycol, oils of vegetable origin, and the like. In particular, biocompatible, biodegradable lactide polymer, lactide glycolide copolymer or polyoxyethylene, polyoxypropylene copolymers may be useful excipients to control the release of the antibody-containing compositions described herein. Other potentially useful administration systems include ethylene vinyl acetate copolymer particles, osmotic pumps, and implantable infusion systems and liposomes. Generally, an anti-coagulant composition of the invention will be in the form of a solution or suspension (or a lyophilized form that can be reconstituted to a solution or suspension), and will preferably include approximately 0.01% to 10% (w/w) of the antibody of the present invention, preferably approximately 0.01% to 5% (w/w) of the antibody. The antibody can be administered as a sole active ingredient in the composition, or as a cocktail including one or more other anti-coagulant (e.g., heparin, hirudin or hirulog, coumadin, warfarin), anti-platelet (e.g., aspirin, Plavix, Ticlid, ReoPro, Integrilin or Aggrestat), or thrombolytic agents (e.g., tissue plasminogen activator, strepokinase and urokinase). Additionally, antibodies of the invention can be administered prior to, or after administration of one or more suitable anti-coagulant, anti-platelet or thrombolytic agents to boost or prolong desired anti-coagulation activity.

As also discussed above, antibodies of the invention can be employed to reduce potential blood coagulation arising from use of medical implementation, e.g. an indwelling device such as a catheter, stent, etc. In one preferred method, the implementation can be treated with an antibody of the invention (e.g., as a 1 mg/ml saline solution) prior to contact with a body fluid. Alternatively, or in addition, an antibody of the invention can be combined with the body fluid in an amount sufficient to minimize blood clotting.

Therapeutic anti-coagulant compositions according to the invention are suitable for use in parenteral or intravenous administration, particularly in the form of liquid solutions. Such compositions may be conveniently administered in unit dose and may be prepared in accordance with methods known in the pharmaceutical art. See *Remington's Pharmaceutical Sciences*, (Mack Publishing Co., Easton Pa., (1980)). By the term "unit dose" is meant a therapeutic composition of the present invention employed in a physically discrete unit suitable as unitary dosages for a primate such as a human, each unit containing a pre-determined quantity of active material calculated to produce the desired therapeutic effect in association with the required diluent or carrier. The unit dose will depend on a variety of factors including the type and severity of thrombosis to be treated, capacity of the subject's blood coagulation system to utilize the antibody, and degree of inhibition or neutralization of FX (or FIX) activation desired. Precise amounts of the antibody to be administered typically will be guided by judgment of the practitioner, however, the unit dose will generally depend on the route of administration and be in the range of 10 ng/kg body weight to 50 mg/kg body weight per day, more typically in the range of 100 ng/kg body weight to about 10 mg/kg body weight per day. Suitable regimens for initial administration in booster shots are also variable but are typified by an initial administration followed by repeated doses at one or more hour intervals by a subsequent injection or other administration. Alternatively, continuous or intermittent intravenous infusions may be made sufficient to maintain concentrations of at least from about 10 nanomolar to 10 micromolar of the antibody in the blood.

In some instances, it may be desirable to modify the antibody of the present invention to impart a desirable biological, chemical or physical property thereto. More particularly, it may be useful to conjugate (i.e. covalently link) the antibody to a pharmaceutical agent, e.g. a fibrinolytic drug such as t-PA, streptokinase, or urokinase to provide fibrinolytic activity or to a targeting agent such as a fibrin-binding domain. Such linkage can be accomplished by several methods including use of a linking molecule such as a heterobifunctional protein cross-linking agent, e.g. SPDP, carbodimide, or the like, or by recombinant methods.

In addition to pharmaceuticals such as a fibrinolytic agent, an antibody of the invention can be conjugated to a toxin of e.g. plant or bacterial origin such as diphtheria toxin (i.e., DT), shiga toxin, abrin, cholera toxin, ricin, saporin, pseudomonas exotoxin (PE), pokeweed antiviral protein, or gelonin. Biologically active fragments of such toxins are well known in the art and include, e.g., DT A chain and ricin A chain. The toxin can also be an agent active at cell surfaces such as phospholipases (e.g., phospholipase C). As another example, the toxin can be a chemotherapeutic drug such as, e.g., vendesine, vincristine, vinblastin, methotrexate, adriamycin, doxirubicin, bleomycin, or cisplatin, or, the toxin can be a radionuclide such as, e.g., iodine-131, yttrium-90, rhenium-188 or bismuth-212 (see generally, Moskaug et al., *J. Biol. Chem.*, 264:15709 (1989); I. Pastan et al., *Cell*, 47:641 (1986); Pastan et al., *Recombinant Toxins as Novel Therapeutic Agents, Ann. Rev. Biochem.*, 61:331 (1992); *Chimeric Toxins* Olsnes and Phil, *Pharmac. Ther.*, 25:355 (1982); published PCT Application No. WO 94/29350; published PCT Application No. WO 94/04689; and U.S. Pat. No. 5,620,939). Also, as discussed above, in addition to a toxin, an antibody of the invention can be conjugated to an effector molecule (e.g. IgG1 or IgG3) to provide complement-fixing ability and antibody-dependent cell-mediated cytoxicity upon administration to a mammal.

Such an antibody-cytotoxin or effector molecule conjugate can be administered in a therapeutically effective amount to a mammal, preferably a primate such as a human, where the mammal is known to have or is suspected of having tumor cells, immune system cells, or endothelia capable of expressing TF. Exemplary of such tumor cells, immune system cells and endothelia include malignancies of the breast and lung, monocytes and vascular endothelia.

Antibodies of the invention also can be conjugated to a variety of other pharmaceutical agents in addition to those described above such as, e.g., drugs, enzymes, hormones, chelating agents capable of binding a radionuclide, as well as other proteins and polypeptides useful for diagnosis or treatment of disease. For diagnostic purposes, the antibody of the present invention can be used either detectably labeled or unlabeled. For example, a wide variety of labels may be suitably employed to detectably-label the antibody, such as radionuclides, flours, enzymes, enzyme substrates, enzyme cofactors, enzyme inhibitors, ligands such as, e.g., haptens, and the like.

Diagnostic methods are also provided including in vivo diagnostic imaging [see, e.g., A. K. Abbas, *Cellular and Molecular Immunology*, pg. 328 (W.B. Saunders Co. 1991)]. For most in vivo imaging applications, an antibody of the invention can be detectably-labeled with, e.g., $^{125}$I, $^{32}$P, $^{99}$Tc, or other detectable tag, and subsequently administered to a mammal, particularly a human, for a pre-determined amount of time sufficient to allow the antibody to contact a desired target. The subject is then scanned by known procedures such as scintigraphic camera analysis to detect binding of the antibody. The analysis could aid in the diagnosis and treatment of a number of thromboses such as those specifically disclosed herein. The method is particularly useful when employed in conjunction with cardiac surgery, particularly angioplasty, or other surgical procedure where undesired formation of a blood clot can occur, to visualize the development or movement of a blood clot.

Antibodies of the invention also can be used to prepare substantially pure (e.g., at least about 90% pure, preferably at least about 96 or 97% pure) native TF, particularly native human TF from a biological sample. For example, native TF can be obtained as previously described (see e.g., L. V. M. Rao et al., *Thrombosis Res.*, 56:109 (1989)) and purified by admixing the solution with a solid support comprising the antibody to form a coupling reaction admixture. Exemplary solid supports include a wall of a plate such as a microtiter plate, as well as supports including or consisting of polystyrene, polyvinylchloride, a cross-linked dextran such as Sephadex™ (Pharmacia Fine Chemicals), agarose, polystyrene beads (Abbott Laboratories), polyvinyl chloride, polystyrene, polyacrylmide in cross-linked form, nitrocellulose or nylon and the like. The TF can then be isolated from the solid support in substantially pure form in accordance with standard immunological techniques. See generally Harlow and Lane supra and Ausubel et al. supra).

As also discussed above, antibodies of the invention can be employed to detect native human TF in a biological sample, particularly native TF associated with a blood clot. Exemplary biological samples include blood plasma, serum, saliva, urine, stool, vaginal secretions, bile, lymph, ocular humors, cerebrospinal fluid, cell culture media, and tissue, particularly vascular tissues such as cardiac tissue. Samples may be suitably obtained from a mammal suffering from or suspected of suffering from a thrombosis, preferably restenosis, associated with, e.g., an invasive medical procedure such as percutanous transluminal coronary intervention, cardiopulmonary bypass surgery, endarterectomy, peripheral vascular bypass grafts, reconstructive or plastic surgery, joint replacement; a heart ailment such as myocardial infarction, cardiomyopathy, valvular heart disease, stable angina, unstable angina, or arterial fibrillation associated with embolization; a coagulopathy including disseminated intravascular coagulation, deep vein thrombosis, deployment of an implementation such as a stent or catheter; shock (e.g., septic shock syndrome), vascular trauma, liver disease, hemorrhagic stroke, heat stroke, malignancies (e.g., pancreatic, ovarian, or small lung cell carcinoma), lupus, eclampsia, perivascular occlusive disease, and renal disease.

For such assays, an antibody of the invention can be detectably-labeled with a suitable atom or molecule e.g., radioactive iodine, tritium, biotin, or reagent capable of generating a detectable product such as an anti-idiotypic antibody attached to an enzyme such as β-galactosidase or horseradish peroxidase, or a fluorescent tag (e.g., fluorescein or rhodamine) in accordance with known methods. After contacting the biological sample with the detectably-labeled antibody, any unreacted antibody can be separated from the biological sample, the label (or product) is detected by conventional immunological methods including antibody capture assay, antibody sandwich assay, RIA, ELISA, immunoprecipitation, immunoabsorption and the like (see Harlow and Lane, supra; Ausubel et al. supra). Any label (or product) in excess of that detected in a suitable control sample is indicative of the presence of native TF, more particularly a blood clot, in the biological sample. For example, antibodies of the invention can be detectably labeled to detect, and preferably quantitate, native TF in accordance with standard immunological techniques such as antibody capture assay, ELISA, antibody sandwich assay, RIA, immunoprecipitation, immunoabsorption and the like. In some cases, particularly when a tissue is used, the immunological technique may include tissue fixation with a reagent known to substantially maintain protein conformation (e.g., dilute formaldehyde). See generally, Ausubel et al., *Current Protocols in Molecular Biology*, John Wiley & Sons, New York, (1989); Harlow and Lane in *Antibodies: A Laboratory Manual*, CSH Publications, NY (1988).

Antibodies of the invention also can be used for detecting and purifying cells which express native TF, including fibroblasts, brain cells, immune cells, (e.g., monocytes), epithelia, as well as certain malignant cells. Preferred methods of detecting and purifying the cells include conventional immunological methods (e.g., flow cytometry methods such as FACS, and immunopanning). Substantially pure populations of cells expressing native TF are useful in clinical and research settings, e.g., to establish such cells as cultured cells for screening TF-binding antibodies.

The invention also provides test and diagnostic kits for detection of native TF, particularly native human TF, in a test sample, especially a body fluid such as blood, plasma, etc., or tissue as discussed above. A preferred kit includes a detectably labeled antibody of the invention. The diagnostic kit can be used in any acceptable immunological format such as an ELISA format to detect the presence or quantity of native TF in the biological sample.

As discussed, the invention also features humanized antibodies that specifically bind to human tissue factor to form a binding complex. The tissue factor may be naturally-occurring or recombinant (rHTF). Preferably, factor X or factor IX binding to the complex is inhibited. In a preferred invention embodiment, the humanized antibody has an affinity constant (Kd) for the hTF of less than about 1 nM, preferably less than about 0.5 nM, more preferably between from about 0.01 nM to about 0.4 nM. See Example 11, below for more information about determining affinity constants for the humanized antibodies. By the phrase "specific binding" is meant that the humanized antibodies form a detectable binding complex with the TF and no other antigen as determined by standard immunological techniques such as RIA, Western blot or ELISA.

Additional humanized antibodies of the invention are further characterized by capacity to increase blood clotting time by at least about 5 seconds as determined by a standard prothrombin (PT) clotting assay. In preferred embodiments, the amount of humanized antibody will be between from about 5 nM to about 75 nM, more preferably about 10 nM to about 50 nM, in the assay. See Example 11 below (describing how to perform the standard PT clotting assay with the humanized antibodies), for instance.

Additionally preferred humanized antibodies in accord with the invention have a binding specificity for tissue factor, preferably human TF, that is about equal or greater than the antibody obtained from H36.D2.B7 deposited under ATCC Accession No. HB-12255. Also preferred are humanized antibodies which have a binding affinity for the TF about equal to or greater than the antibody obtained from H36.D2.B7 deposited under ATCC Accession No. HB-12255. Methods for determining binding specificity and affinity are known in the field and include the specific assays described below.

Further humanized antibodies in accord with the invention include at least one murine complimentarity determining region (CDR). As will be appreciated, immunoglobin light and heavy chain share certain structural similarities eg., each includes a framework of four regions (FR1-4) whose sequences are relatively conserved. Each of FR1-4 (FR1, FR2, FR3, FR4) are covalently connected by three CDRs i.e., CDR1, CDR2, CDR3. There is general recognition that the four FRs largely adopt a beta-sheet configuration and the interconnected CDRs form loops connecting, and in some instances, forming part of the beta-sheet structure. Most CDRs are held close to adjoining FRs, and with a corresponding CDR from the opposite light or heavy chain, help form the antigen binding site. A wide range of CDRs and FRs have been disclosed. See eg., Kabat et al. in *Sequences of Proteins of Immunological Interest* US Dept. of Health and Human Services, US Government Printing Office (1987).

See also EP-A-0239400 and U.S. Pat. No. 5,985,279 (describing methods of making altered antibodies in which CDRs are derived from different species than the FR).

By the phrase "humanized" is meant an immunoglobin that includes a human framework region and one or more CDRs from a non-human source, usually rodent such as a rat or mouse immunoglobin. The non-human immunoglobin providing the CDRs is called a "donor" and the human immunoglobin called the "acceptor". Constant regions need not be present, as in, for example, certain TF binding fragments of such immunoglobins. Preferred constant regions, if present, are substantially identical to human immunoglobin constant regions i.e., at least about 90% identical with regard to the amino acid sequence, preferably at least about 95% identical or greater. Accordingly, nearly all parts of the humanized immunoglobin, with the possible exception of the CDRs are substantially identical to corresponding parts of naturally-occurring human immunoglobin sequences.

By the phrase "humanized antibody" is meant an antibody that includes a humanized light chain and a humanized heavy chain immunoglobin. Methods for making and using such antibodies have already been discussed above. See S. L. Morrison, supra; Oi et al., supra; Teng et al., supra; Kozbor et al., supra; Olsson et al., supra; and other references cited previously.

For example, an illustrative humanized antibody includes: 1) light and heavy chain frameworks (FRs) that are each at least about 90% identical in amino acid sequence, preferably at least 95% identical to corresponding human FRs, 2) at least one CDR from a mouse, preferably all the CDRs from the mouse, 3) and an immunoglobin constant region that is at least about 90% identical, preferably at least 95% identical to a corresponding human immunoglobin constant region. It will be appreciated that the donor antibody has been "humanized" by the process of "humanization" because the resultant humanized antibody is expected to bind to the same antigen as the donor antibody that provides the CDRs.

It will be further appreciated that the humanized antibodies provided herein may have one or more additional conservative amino acid substitutions which can be contiguous or non-contiguous as needed. For example, such substitutions will typically have substantially little or no effect on antigen binding or other immunoglobin functions. By the phrase "conservative substitution" including plural forms is meant combinations of: gly ↔ ala; val ↔ ile ↔ leu; asp ↔ glu; asn ↔ gln; ser ↔ thr, lys ↔ arg; and phe ↔ tyr.

Additional humanized antibodies feature a variable region that is at least 70% identical in amino acid sequence (eg., about 73% to 75% identical), to the corresponding variable region of one or more native human immunoglobin sequences. Further humanized antibodies in accord with the invention have at least 90% identity over the entire antibody to one or more human antibodies.

More specific humanized antibodies of the invention are those in each of frameworks (FRs) 1, 2, 3 and 4 has at least about 90% amino acid sequence identity, preferably at least about 95% or greater identity to the light chain FR sequences shown in FIG. 12A (SEQ ID NO. 72-82, respectively, in order of appearance). Preferably, the sequence is as shown as "LC-09" in FIG. 12A (SEQ ID NO: 79). Further preferred are those humanized antibodies that include a light chain constant region having at least about 90% amino acid sequence identity, and preferably, at least about 95% sequence identity or greater to the sequence shown in FIG. 14A or 15A (SEQ ID NOS: 97 and 99, respectively).

Further specific humanized antibodies are those in which each of frameworks (FRs) 1, 2, 3 and 4 has at least about 90% amino acid sequence identity, preferably about 95% identity or greater to the heavy chain sequences shown in FIG. 13A (SEQ ID NOS: 83-96, respectively, in order of appearance). Preferably, the sequence is as shown as "HC-08" (SEQ ID NO: 91) in FIG. 13A. Additional humanized antibodies have a heavy chain constant region with at least about 90% amino acid sequence identity, and preferably, at least about 95% identity or greater, to sequence shown in FIG. 14B or 15B (SEQ ID NOS: 98 and 100, respectively).

In certain embodiments, the humanized antibody will have an IgG1 (hOAT) or IgG4 (hFAT) isotype. See Example 9.

Also provided by the present invention are functional fragments of the humanized antibodies disclosed herein. Preferred fragments specifically bind TF with an affinity constant (Kd) of less than about 1 nM, preferably less than about 0.5 nM, more preferably between from about 0.01 nM to about 0.4 nM. Specifically preferred are antigen binding Fab, Fab', and F(ab)$_2$ fragments.

As discussed, the invention features humanized antibodies that include at least one murine complementarity determining region (CDR), eg., CDR1, CDR2, CDR3. In a preferred embodiment, the antibodies bind specifically to human tissue factor (TF) to form a complex. Typically, the factor X or factor IX binding to TF or TF:VIIa and activation by TF:FVIIa thereto is inhibited. As mentioned above, preferred CDRs (light and heavy chain) are from a rodent source, typically the mouse.

In one embodiment of the humanized antibodies of the invention, the antibodies further include at least one human framework (FR) region. Preferably, all the FR regions (light and heavy chain) are human.

In a more particular embodiment, the first CDR(CDR1) of the heavy chain hypervariable region is at least 90% identical to the CDR1 amino acid sequences shown in FIG. 13B (both SEQ ID NO: 8), preferably at least about 95% identical or greater to that sequence. Typically, the second CDR(CDR2) of the heavy chain hypervariable region is at least 90% identical to the CDR2 amino acid sequence shown in FIG. 13C (SEQ ID NOS: 9 and 101), preferably at least about 95% identical or greater. Preferably also, the third CDR(CDR3) of the heavy chain hypervariable region is at least 90% identical to the CDR3 sequence shown in FIG. 13D (both SEQ ID NO: 10), more preferably about 95% identical or greater to that sequence.

Identity between two nucleic acid sequences can be determined by inspection and/or use of conventional computer software such as BLAST and FASTA.

In another invention embodiment, the first CDR(CDR1) of the light chain hypervariable region is at least 90% identical to the CDR1 amino acid sequence shown in FIG. 12B (fragment of SEQ ID NO: 2), preferably at least about 95% identical or greater. Typically, the second CDR(CDR2) of the light chain hypervariable region is at least 90% identical to the CDR2 amino acid sequence shown in FIG. 12C (SEQ ID NO: 6), preferably about 95% identical or greater. Preferably, the third CDR(CDR3) of the light chain hypervariable region is at least 90% identical to the CDR3 amino acid sequence shown in FIG. 12D (SEQ ID NO: 7), more preferably about 95% identical or greater to that sequence.

Additional humanized antibodies of the invention include a first framework (FR1) of the heavy chain hypervariable region which FR1 is at least 90% identical to the FR1 amino acid sequence shown in FIG. 13A (fragment of SEQ ID NO: 91) as "FR1 HC-08", preferably about 95% identical or greater to that sequence. In one embodiment, the FR1 comprises at least one of the following amino acid changes: E1 to Q; Q5 to V; P9 to G; L11 to V; V12 to K; Q19 to R; and T24 to A. Preferably, the FR1 includes two, three, four, five, or six of those changes with all of those amino acid changes being preferred for many applications.

Further humanized antibodies of the invention include a second framework (FR2) of the heavy chain hypervariable region which FR2 is at least 90% identical to the FR2 sequence shown in FIG. 13A (fragment of SEQ ID NO: 91) as "FR2 HC-08", preferably about 95% identical or greater to that sequence. In one embodiment, the FR2 at least one of the following amino acid changes: 41H to P; and 44S to G. A preferred FR2 includes both of those amino acid changes.

The invention also features humanized antibodies in which a third framework (FR3) of the heavy chain hypervariable region is at least 90% identical to the FR3 sequence shown in FIG. 13A (fragment of SEQ ID NO: 91) as "FR3 HC-08", preferably about 95% identical or greater to that sequence. In one embodiment, the FR3 includes at least one of the following amino acid changes: 76S to T; 77T to S; 80F to Y; 82H to E; 84N to S; 87T to R; 89D to E; and 91S to T. A preferred FR3 includes two, three, four, five or six of those amino acid changes with all seven of those amino acid changes being generally preferred.

Also featured are humanized antibodies in which the fourth framework (FR4) of the heavy chain hypervariable region is at least 90% identical to the FR4 amino acid sequence shown in FIG. 13A (fragment of SEQ ID NO: 91) as "FR4 HC-08", preferably at least about 95% identical or greater to that sequence. Preferably, the FR4 includes the following amino acid change: 113L to V.

Additional humanized antibodies in accord with the invention feature a first framework (FR1) of the light chain hypervariable region which is at least about 90% identical to the FR1 amino acid sequence shown in FIG. 12A (fragment of SEQ ID NO: 79) as "FR1 LC-09", preferably at least about 95% identical or greater to that sequence. In one embodiment, the FR1 comprises at least one of the following amino acid changes: 11Q to L; 15L to V; 17E to D; and 18 to R. A preferred FR1 includes two or three of such amino acid changes with all four amino acid changes being generally preferred.

The present invention also features humanized antibodies in which a second framework (FR2) of the light chain hypervariable region is at least about 90% identical to the FR2 amino acid sequence shown in FIG. 12A (fragment SEQ ID NO: 79) as "FR2 LC-09", preferably at least about 95% identical or greater to that sequence. A preferred FR2 has the following amino acid change: 37Q to L.

Also encompassed by the invention are humanized antibodies in which a third framework (FR3) of the light chain hypervariable region is at least about 90% identical to the FR3 amino acid sequence shown in FIG. 12A (fragment of SEQ ID NO: 79) as "FR3 LC-09", preferably at least about 95% identical or greater to that sequence. In one embodiment, the FR3 has at least one of the following amino acid changes: 70K to D, 74K to T, 80A to P, 84A to V, and 85N to T. Preferably, the FR3 has two, three, or four of such amino acid changes with all five of the changes being generally preferred.

Additional humanized antibodies of the invention include a fourth framework (FR4) of the light chain hypervariable region which FR4 is at least about 90% identical to the sequence shown in FIG. 12A (fragment of SEQ ID NO: 79) as "FR4 LC-09", preferably at least about 95% identical or greater to that sequence. In one embodiment, the FR4 includes at least one and preferably all of the following amino acid changes: 100A to Q; and 106L to I.

The invention also features a human TF binding fragment of the foregoing humanized antibodies. Examples of such fragments include Fab, Fab', and F(ab)$_2$.

In a particular embodiment, the invention features a humanized antibody that includes at least one rodent complementarity determining region (CDR), usually mouse. Preferably, that antibody binds specifically to human tissue factor (TF) to form a complex in which factor X or factor IX binding to TF or TF/VIIa and activation by TF/VIIa thereto is inhibited. Also preferably, the humanized antibody includes, on the heavy chain, at least one of and more preferably all of the following components:

a) a first CDR(CDR1) which is at least 95% identical to CDR1 amino acid sequences shown in FIG. 13B (SEQ ID NO: 8), b) a second CDR(CDR2) which is at least 95% identical to the CDR2 amino acid sequence shown in FIG. 13C (SEQ ID NO: 9 or 101), c) a third CDR(CDR3) which is at least 95% identical to the CDR3 amino acid sequence shown in FIG. 13D (SEQ ID NO: 10), d) a first framework (FR1) which is at least 95% identical to the FR1 amino acid sequence shown in FIG. 13A (fragment of SEQ ID NO: 91) as "FR1 HC-08", e) a second framework (FR2) which is at least 95% identical to the FR2 amino acid sequence shown in FIG. 13A (fragment of SEQ ID NO: 91) as "FR2 HC-08", f) a third framework (FR3) which is at least 95% identical to the FR3 amino acid sequence shown in FIG. 13A (fragment of SEQ ID NO: 91) as "FR3 HC-08", and g) a fourth framework (FR4) which is at least 95% identical to the FR4 amino acid sequence shown in FIG. 13A (fragment of SEQ ID NO: 91) as "FR4 HC-08".

In a particular embodiment, the humanized antibody also includes, on the light chain, at least one of and preferably all of the following components:

h) a first CDR(CDR1) which is at least 95% identical to CDR1 amino acid sequence shown in FIG. 12B (fragment of SEQ ID NO: 2), i) a second CDR(CDR2) which is at least 95% identical to the CDR2 amino acid sequence shown in FIG. 12C (SEQ ID NO: 6), j) a third CDR(CDR3) which is at least 95% identical to the CDR3 amino acid sequence shown in FIG. 12C (SEQ ID NO: 6), k) a first framework (FR1) which is at least 95% identical to the FR1 amino acid sequence shown in FIG. 12A (fragment of SEQ ID NO: 79) as "FR1 LC-09", l) a second framework (FR2) which is at least 95% identical to the FR2 amino acid sequence shown in FIG. 12A (fragment of SEQ ID NO: 79) as "FR2 LC-09", m) a third framework (FR3) which is at least 95% identical to the FR3 amino acid sequence shown in FIG. 12A (fragment of SEQ ID NO: 79) as "FR3 LC-09", and n) a fourth framework (FR4) which is at least 95% identical to the FR4 amino acid sequence shown in FIG. 12A (fragment of SEQ ID NO: 79) as "FR4 LC-09". Preferably, the humanized antibody further includes the light chain constant sequence of FIG. 14A (SEQ ID NO: 97) or FIG. 15A (SEQ ID NO: 99). Also preferably, the antibody includes the heavy chain constant region of FIG. 14B (SEQ ID NO: 98) or FIG. 15B (SEQ ID NO: 100).

The invention also features a humanized antibody that includes, on the heavy chain, at least one of and preferably all of the following components:

a) a first CDR(CDR1) identical to the CDR1 amino acid sequence shown in FIG. 13B (SEQ ID NO: 8), b) a second CDR(CDR2) identical to the CDR2 amino acid sequence shown in FIG. 13C (SEQ ID NOS: 9 or 101), c) a third CDR(CDR3) identical to the CDR3 amino acid sequence shown in FIG. 13D (SEQ ID NO: 10), d) a first framework (FR1) identical to the FR1 amino acid sequence shown in FIG. 13A (fragment of SEQ ID NO: 91) as "FR1 HC-08", e) a second framework (FR2) identical to the FR2 amino acid sequence shown in FIG. 13A (fragment of SEQ ID NO: 91) as "FR2 HC-08", f) a third framework (FR3) identical to the FR3 amino acid sequence shown in FIG. 13A (fragment of SEQ ID NO: 91) as "FR3 HC-08"; and g) a fourth framework (FR4) identical to the FR4 amino acid sequence shown in FIG. 13A (fragment of SEQ ID NO: 91) as "FR4 HC-08".

In one embodiment, the humanized antibody further includes, on the light chain, at least one of and preferably all of the following components:

h) a first CDR(CDR1) identical to CDR1 amino acid sequence shown in FIG. 12B (fragment SEQ ID NO: 2), i) a second CDR(CDR2) identical to the CDR2 amino acid sequence shown in FIG. 12C (SEQ ID NO: 6), j) a third CDR(CDR3) identical to the CDR3 amino acid sequence shown in FIG. 12D (SEQ ID NO: 7), k) a first framework (FR1) identical to the FR1 amino acid sequence shown in FIG. 12A (fragment of SEQ ID NO: 79) as "FR1 LC-09", l) a second framework (FR2) identical to the FR2 amino acid sequence shown in FIG. 12A (fragment of SEQ ID NO: 79) as "FR2 LC-09", m) a third framework (FR3) identical to the FR3 amino acid sequence shown in FIG. 12A (fragment of SEQ ID NO: 79) as "FR3 LC-09", and n) a fourth framework (FR4) identical to the FR4 amino acid sequence shown in FIG. 12A (fragment of SEQ ID NO: 79) as "FR4 LC-09". Preferably, the humanized antibody further includes the light chain constant sequence of FIG. 14A (SEQ ID NO: 97) or FIG. 15A (SEQ ID NO: 99). Also preferably, the antibody includes the heavy chain constant region of FIG. 14B (SEQ ID NO: 98) or FIG. 15B (SEQ ID NO: 100).

The humanized antibodies of the present invention may exist in a variety of suitable forms in addition to whole antibodies; including, for example, Fv, Fab, and F(ab')$_2$ as well as bifunctional hybrid antibodies (e.g., Lanzavecchia et al., *Eur. J. Immunol.* 17, 105 (1987)) and in single chains (e.g., Huston et al., *Proc. Natl. Acad. Sci. U.S.A.*, 85, 5879-5883 (1988) and Bird et al., *Science* 242, 423-426 (1988), which are incorporated herein by reference). (See, Hood et al., Immunology, Benjamin, N.Y., 2.sup.nd ed. (1984), Harlow and Lane, *Antibodies. A Laboratory Manual*, Cold Spring Harbor Laboratory (1988) and Hunkapiller and Hood, *Nature,* 323, 15-16 (1986), which are incorporated herein by reference.).

By the phrase "chimeric antibody" or related phrase including plural forms is meant antibodies whose light and heavy chain genes have been constructed, typically by genetic engineering, from immunoglobulin gene segments belonging to different species. For example, the variable (V) segments of the genes from a mouse monoclonal antibody may be joined to human constant (C) segments, such as $\gamma_1$ $\gamma_3$. A typical therapeutic chimeric antibody is thus a hybrid protein consisting of the V or antigen-binding domain from a mouse antibody and the C or effector domain from a human antibody, although other mammalian species may be used. A specifically preferred chimeric antibody is the cH36 mouse-human chimera disclosed herein.

The humanized antibodies of the present invention can be polyclonal or monoclonal, as needed, and may have an IgG1 or IgG4 isotype.

The humanized antibodies disclosed herein can be produced by one or a combination of strategies including those already referenced above. See eg., S. L. Morrison, supra; Oi et al., supra; Teng et al., supra; Kozbor et al., supra; Olsson et al., supra; and other references cited previously.

In one approach, four general steps were employed to humanize the antibodies. First, the amino acid sequences of the mouse antibody light and heavy chains were obtained from the cH36 mouse-human chimeric antibody. Second, the cH36 antibody was humanized by determining which human antibody framework region gave the "best fit" i.e., most closely resembled the corresponding mouse framework amino acid sequence. Third, relevant light and heavy chain FR sequences were humanized, and fourth, transfection and expression of isolated nucleic acid(s) that encode the humanized light or heavy chain (or humanized light and heavy chain e.g., see the mega vectors described below).

In some instances, a limited number of framework amino acids of a humanized immunoglobin were chosen to be the same as the amino acids at those positions in the donor rather than in the acceptor. One advantage of this technique is to enhance affinity of the antibody that includes the humanized immunoglobin chain. See also U.S. Pat. Nos. 5,985,279; 5,693,762; and EP-A0239400 (disclosing general methods for making humanized antibodies).

More particularly, the "best fit" approach was applied to humanizing the chimeric anti-tissue factor antibody cH36 is specifically preferred. In this approach, the murine light and heavy chain variable sequences shown in FIGS. 1A and 1B (SEQ ID NOS: 2 and 4) were used to search ("compare") all available protein databases for those human antibody variable domain sequences that are most homologous to the murine variable domain. See e.g., Kabat et al., supra. A number of readily available computer programs can be used to perform this step such as BLAST, FASTA and related programs. Frameworks 1, 2, 3, and 4 of the light and heavy chain were of special interest since these sites are almost universally understood to hold the CDRs in proper orientation for antigen binding. Output stemming from the search was typically a list of sequences most homologous to the query mouse sequences, the percent homology to each sequence, and an alignment of each human sequence to the corresponding murine sequence. The analysis was generally performed on the light and heavy chains independently.

According to the "best fit" approach, the number of mismatched amino acids was minimized between the query mouse framework sequence and the corresponding human framework sequence in the database. In most cases, suitable human framework regions were selected based on the following identity criteria. On the light chain, the amino acid sequence of the murine FR1 was at least about 80% identical to the corresponding human FR1; the murine FR2 was at least about 90% identical to the corresponding human FR2, the murine FR3 was at least about 90% identical to the human FR3; and the murine FR4 was at least about 75% identical to the corresponding human FR4. And on the heavy chain, the amino acid sequence of the murine FR1 was chosen to be at least about 80% identical to the corresponding human FR1; the murine FR2 was at least about 85% identical to the human FR2; the murine FR3 was chosen to be at least about 70% identical to the corresponding human FR3; and the murine FR4 was at least about 90% identical to the corresponding human FR4. Typically, conservative amino acid substitutions were favored when evaluating similar candidate human framework sequences. It was found that when such factors were considered the resulting human frameworks served as a good reference point for humanization of the chimeric cH36 antibody.

Also preferably, according to the "best fit" approach all of the human frameworks on the light and heavy chain were derived from the same human antibody clone where possible.

Once a decision on a desired human framework was made, recombinant polymerase chain reaction (PCR) techniques were used to make desired amino acid substitutions in both the light and heavy chains. Typically, oligonucleotides were made and used to mutagenize mouse variable domain frameworks to contain desired residues. Oligonucleotides having a variety of lengths were employed. See WO 92/07075 for general disclosure relating to recombinant PCR and related methods.

In general, regular PCR was used for cloning, to introduce cloning or diagnostic endonuclease sites, and to change amino acid residues located at the ends of the variable regions. PCR-based mutagenesis was used to change multiple amino acid residues at a time, especially when these residues were in the middle of the variable regions. Site directed mutagenesis was used to introduce one or two amino acid substitutions at a time. After each step, the partially humanized clones were sequenced and some of these variable regions were later cloned into expression vectors. More specific methods for performing these manipulations are described in the Examples section.

After performing the foregoing "best fit" approach to humanizing the chimeric cH36 antibody, mutagenized nucleic acids encoding framework and/or CDR were linked to an appropriate DNA encoding a light or heavy chain constant region. Such constructs were then cloned into an expression vector, and transfected into host cells, preferably mammalian cells. These steps were achieved by using recombinant and cell culture techniques known in the field. Accordingly, a humanized antibody of the invention can be prepared by the following general method:

(a) preparing a first expression vector including a replicon appropriate for the expression host and a suitable promoter operably linked to a DNA sequence which encodes at least a variable domain of an Ig heavy or light chain, the variable domain comprising humanized framework regions 1-4 made according to the "best fit" approach and murine CDRs 1-3 from the cH36 antibody, (b) preparing a second replicable expression vector including a suitable promoter operably linked to a DNA sequence which encodes at least the variable domain of a complementary Ig light or heavy chain respectively, that variable domain comprising complementary humanized framework regions 1-4 made according to the foregoing "best fit" approach and murine CDRs 1-3 from the cH36 antibody;

(c) transfecting a cell line with the first or both prepared vectors; and (d) culturing said transfected cell line to produce said altered antibody.

Preferably the DNA sequence in steps (a) and (b) encode suitable constant domains from the human antibody chain. Suitable isotypes include IgG1 and IgG4, for example.

Alternatively, a suitable humanized antibody of the invention can be prepared by making a single replicable "mega" vector that includes an appropriate promoter operably linked to a DNA sequence which encodes at least a variable domain of an Ig heavy or light chain, the variable domain comprising humanized framework regions 1-4 made according to the "best fit" approach and murine CDRs 1-3 from the cH36 antibody. Preferably, the mega vector will further include a suitable promoter operably linked to a DNA sequence which encodes at least the variable domain of a complementary Ig light or heavy chain respectively, that variable domain comprising complementary humanized framework regions 1-4 made according to the foregoing "best fit" approach and murine CDRs 1-3 from the cH36 antibody. Use of the mega vector will often be appropriate in invention embodiments in which humanized antibody expression from a single vector is needed.

Other methods are well-suited for making the humanized antibodies and fragments of this invention. In one embodiment, the method includes at least one and preferably all of the following steps:

a) comparing the amino acid sequence of a light chain framework from a rodent antibody against a collection of corresponding human antibody framework sequences, preferably a mouse antibody, b) selecting a human framework sequence from the collection having the greatest amino acid sequence identity (i.e., at least about 70% sequence identity) to the corresponding rodent light chain framework, c) mutagenizing a DNA segment encoding the rodent light chain framework to encode a humanized light chain framework having an amino acid sequence that is substantially identical (i.e., at least about 95% identical) to the human framework sequence selected in step b), d) repeating steps a) thru c) for each individual framework of the rodent light chain to produce a plurality of DNA sequences in which each sequence encodes a humanized light chain framework in which each of the corresponding human framework sequences selected in step b) is preferably from the same or different human antibody, e) assembling into a first vector encoding at least the light chain variable region of the rodent antibody, the DNA sequences encoding the humanized framework sequences produced in step d); and f) introducing the assembled vector into a suitable host under conditions sufficient to produce the humanized antibody. Preferred light chain framework sequences for use with the method include those specific mouse and humanized light chain frameworks disclosed herein.

In one embodiment, the foregoing method for making the humanized antibody further includes at least one and preferably all of the following steps:

g) comparing the amino acid sequence of a heavy chain framework from the rodent antibody against a collection of corresponding human antibody framework sequences, h) selecting a human framework sequence from the collection having the greatest amino acid sequence identity (i.e., at least about 70% sequence identity) to the corresponding rodent heavy chain framework, i) mutagenizing a DNA segment encoding the rodent heavy chain framework to encode a humanized heavy chain framework having an amino acid sequence that is substantially identical (i.e., at least about 95% identical) to the human framework sequence selected in step h); and j) repeating steps g) thru i) for each individual framework of the rodent heavy chain to produce a plurality of DNA sequences in which each sequence encodes a humanized heavy chain framework. Preferably, each of the corresponding human framework sequences selected in step h) are from the same or different human antibody. Preferred heavy chain framework sequences for use with the method include those specific mouse and humanized heavy chain frameworks disclosed herein.

More particular methods for making the humanized antibody include assembling into a second vector encoding at least the heavy chain variable region of the rodent antibody, the DNA sequences encoding the humanized framework sequences produced in step j); and introducing the assembled first and second vectors into the host under conditions sufficient to produce the humanized antibody.

As discussed, it will often be preferable to express the humanized antibodies of this invention from a single vector which can sometimes be a "mega" vector. In one embodiment, the method includes assembling into the first vector encoding at least the heavy chain variable region and the light chain variable region of the rodent antibody, the DNA sequences encoding the humanized framework sequences produced in step j); and introducing the further assembled first vector into the host under conditions sufficient to produce the humanized antibody.

By the words "assembling" or "assembled" is meant use of standard recombinant techniques to introduce subject DNA sequences encoding the humanized frameworks into the vectors. Such assembly can be performed by one or combination of approaches including, but not limited to, introducing iterative changes to a single framework sequence, cutting and pasting fragments together (via use of restriction endonucleases and ligase), or by synthetic DNA synthesis techniques. See generally Harlow and Lane supra and Ausubel et al. supra.

The foregoing methods for making humanized antibodies can be practiced with nearly any acceptable mutagenesis technique. In particular, one or both of steps c) and i), above, can employ site directed mutagenesis or standard PCR methods to replace desired rodent amino acids in the framework with appropriate human amino acids. Typically, the sequence of the modified (humanized) framework corresponds to the selected human framework sequence from the database.

The humanized antibody can be prepared using any suitable recombinant expression system such as those disclosed in S. L. Morrison, supra; Oi et al., supra; Teng et al., supra; Kozbor et al., supra; Olsson et al., supra; and other references cited previously.

For example, suitable nucleic acids of the invention encode at least one of the heavy or light chain of the humanized antibodies or fragments thereof disclosed herein. Typically, the nucleic acid is a recombinant DNA vector that includes the isolated nucleic acid. The DNA vector will typically further include an expression control polynucleotide sequence operably linked to the humanized immunoglobulin coding sequences, including naturally-associated or heterologous promoter regions. Preferably, the expression control sequences will be eukaryotic promoter systems in vectors capable of transforming or transfecting eukaryotic host cells, but control sequences for prokaryotic hosts may also be used. Once the vector has been incorporated into the appropriate host, the host is maintained under conditions suitable for high level expression of the nucleotide sequences, and, as desired, the collection and purification of the light chains, heavy chains, light/heavy chain dimers or intact antibodies, binding fragments or other immunoglobulin forms may follow.

The nucleic acid sequences of the present invention capable of ultimately expressing the desired humanized antibodies can be formed from a variety of different polynucleotides (genomic or cDNA, RNA, synthetic oligonucleotides, etc.) and components (e.g., V, J, D, and C regions), as well as by a variety of different techniques. Joining appropriate genomic and synthetic sequences is presently the most common method of production, but cDNA sequences may also be utilized. See eg., S. L. Morrison, supra; Oi et al., supra; Teng et al., supra; Kozbor et al., supra; Olsson et al., supra; European Patent Publication No. 0239400 and Riechmann, L. et al., Nature, 332, 323-327 (1988); and references cited therein.

In one embodiment, suitable DNA expression vectors include one or more selection markers, e.g., tetracycline, ampicillin, or neomycin, to permit detection of those cells transformed with the desired DNA sequences (see, e.g., U.S. Pat. No. 4,704,362, which is incorporated herein by reference). *E. coli* is one prokaryotic host useful particularly for cloning the polynucleotides of the present invention. Other microbial hosts suitable for use include but are not limited to bacilli, such as *Bacillus subtilus*, and other enterobacteriacea, such as *Salmonella, Serratia*, various *Pseudomonas* species and other microbes such as actinomycetes (e.g., *Streptomyces* species), yeast (e.g., *Saccharomyces* species) or fungi (e.g., *Aspergillus* species). In these prokaryotic hosts, one can also make expression vectors, which will typically contain expression control sequences compatible with the host cell (e.g., promoters and an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation. Other microbes, such as yeast, may also be used for expression. *Saccharomyces* is a preferred host, with suitable vectors having expression control sequences, such as promoters, including 3-phosphoglycerate kinase or other glycolytic enzymes, and an origin of replication, termination sequences and the like as desired. Plants (e.g., *Arabidopsis, Nicotinia*, etc.) and plant cell culture may also be used to express and produce the antibodies of the present invention In addition to forgoing microorganism-based systems, mammalian tissue cell culture may also be used to express and produce the polypeptides of the present invention (see, Winnacker, From Genes to Clones, VCH Publishers, N.Y., N.Y. (1987), which is incorporated herein by reference).

In many instances, eukaryotic cells will be generally preferred, typically CHO cell lines, various COS cell lines, NSO cells, BK cells, HeLa cells, preferably myeloma cell lines, etc., or transformed B-cells of hybridomas. Expression vectors for these cells can include expression control sequences, such as an origin of replication, a promoter, and enhancer (Queen et al., *Immunol. Rev.* 89, 46-68 (1986)), and necessary processing information sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, cytomegalovirus and the like.

Preferred DNA vectors for practicing the invention include the following operatively linked sequences: an antibiotic resistance marker e.g., ampicillin resistance, F1 origin, and heavy chain (HC) or light chain (LC) variable region. That variable region can be inserted into an appropriate HC expression that includes operatively linked in sequence: the HC variable region, human IgG1 or IgG4 constant region, first poly A site, SV40 promoter, antibiotic resistance marker such as neomycin resistance, second poly A site, cytomegalovirus (CMV) promoter/enhancer, and suitable leader sequence.

Additionally preferred DNA vectors include the LC variable region operatively linked to a rodent kappa intron (e.g., mouse) which intron is operatively linked to a suitable human kappa constant region; and antibiotic resistance marker such a neomycin resistance.

Figure 11:
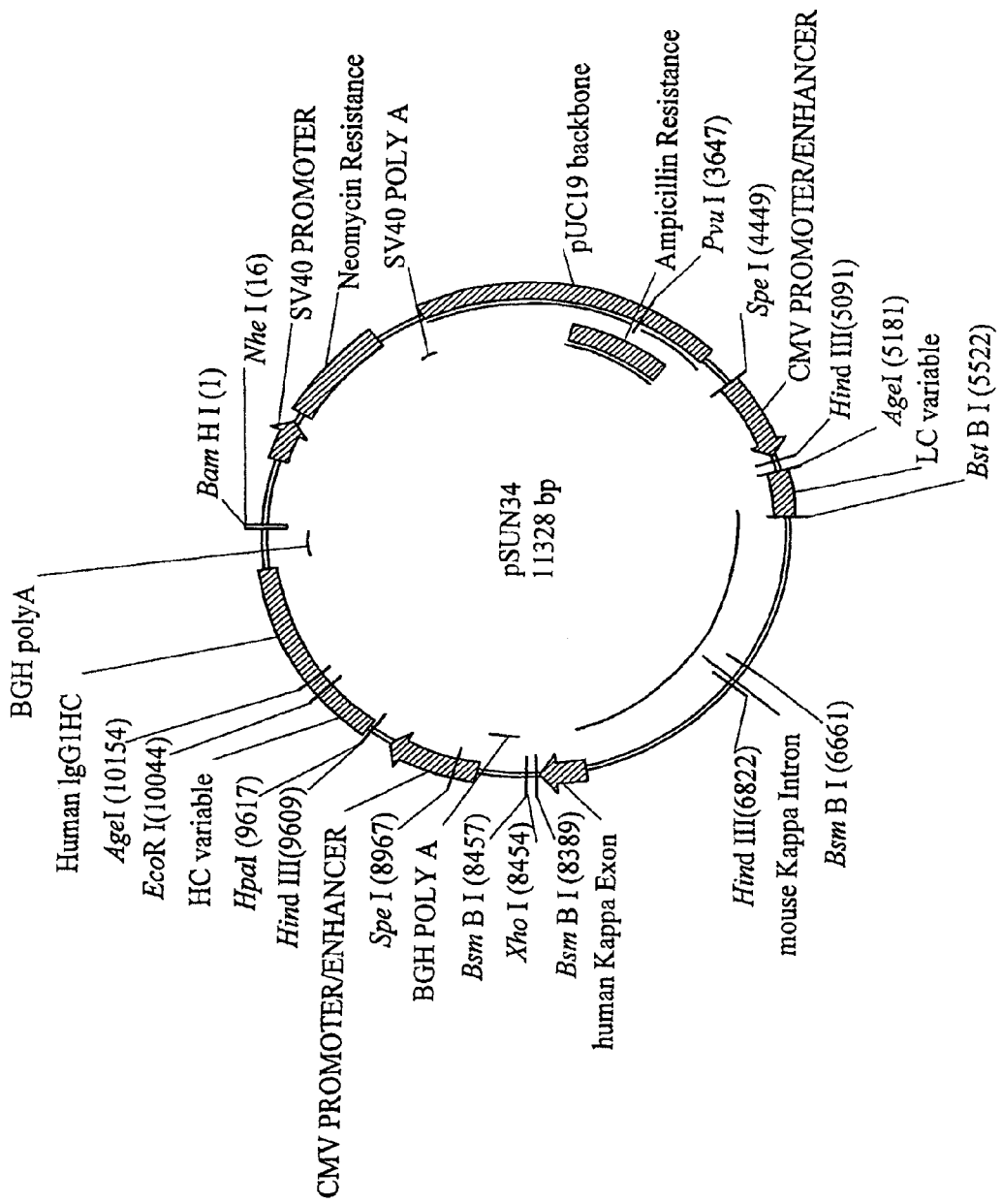
FIG. 11 is a drawing showing a plasmid map of humanized anti-TF IgG1 antibody expression vector (pSUN 34).

As discussed, it will often be highly useful to express humanized antibodies of the present invention from a single nucleic acid. A preferred DNA vector is sometime referred to herein as a "mega" vector and includes operatively linked in sequence the following components: SV40 promoter, antibiotic resistance marker such as neomycin, first poly A site, first CMV promoter/enhancer, LC variable region, rodent kappa intron (e.g., mouse), human kappa exon, second poly A site, second CMV promoter/enhancer, HC variable sequence, and human IgG1 or IgG4 heavy chain constant region. A specific example of such a mega vector is the humanized anti-TF IgG1 antibody expression vector described below in Example 10. See also FIG. 11.

The following three nucleic acid vectors pSUN36 (humanized anti-TF antibody Ig G1-HC expression vector), pSUN37 (humanized anti-TF antibody Ig G4-HC expression vector), and pSUN38 (humanized anti-TF antibody LC expression vector) have been deposited pursuant to the Budapest Treaty with the American Type Culture Collection (ATCC) at 10801 University Boulevard, Manassas Va. 20110-2209. The vectors were assigned the following Accession Numbers: PTA-3727 (pSUN36); PTA-3728 (pSUN37); and PTA-3729 (pSUN38).

A variety of suitable host cells can be used to produce the humanized antibodies or fragments disclosed herein. In one embodiment the method includes providing a host cell transfected with either 1) a first expression vector encoding the light chain of the humanized antibody or fragment thereof and a second expression vector encoding the heavy chain of the humanized antibody or fragment thereof, or 2) a single expression vector encoding both the light chain and the heavy chain of the humanized antibody or fragment thereof, maintaining the host cell under growth conditions in which each chain is expressed; and isolating the humanized antibody or fragment thereof.

For example, the cell line that is transfected to produce the humanized antibody can be Chinese Hamster Ovary (CHO) cell line, BK cell line or NSO cell line. Further acceptable cell lines include recognized immortalized mammalian cell lines, preferably of lymphoid origin, such as a myeloma, hybridoma, trioma or quadroma cell lines. The cell line may also comprise a normal lymphoid cell, such as a B-cell, which has been immortalized by transformation with a virus, such as the Epstein-Barr virus. Methods for using CHO cells for expression of a variety of proteins have been reported. See e.g., Urlaub et al., Proc. Natl. Acad. Sci. U.S.A., 77 4216-4220 (1980)) and WO 87/04462. NSO cells, as described below in the Examples section, are also preferred.

Although the cell line used to produce the humanized antibody is preferably a mammalian cell line, any other suitable cell, such as a bacterial cells, plant cells, insect cells or yeast cells, may alternatively be used. In particular, it is envisaged that *E. coli*-derived bacterial strains could be used.

Once expressed from an appropriate cell source, the whole antibodies, their dimers, individual light and heavy chains, or other immunoglobulin forms of the present invention such as functional humanized antibody fragments can be recovered and purified according to standard procedures. Such procedures include, but are not limited to, ammonium sulfate precipitation, affinity columns, column chromatography, gel electrophoresis and the like (See, generally, Scopes, R., *Protein Purification*, Springer-Verlag, N.Y. (1982)). Substantially pure humanized antibodies of the invention and fragments thereof feature at least about 90 to 95% homogeneity with about 98 to 99% or more homogeneity being generally preferred for most pharmaceutical uses. Once purified, partially or to homogeneity as desired, a humanized antibody may then be used therapeutically or in developing and performing assay procedures, immunofluorescent stainings, and the like (See, generally, *Immunological Methods*, Vols. I and II, Lefkovits and Pernis, eds., Academic Press, New York, N.Y. (1979 and 1981)).

A preferred method of purifying the present humanized antibodies involves conventional affinity and ion exchange chromatography, preferably using recombinant Protein A Sepharose (to which human Ig G Fc has recognized high affinity). Antibody containing fractions are collected and subjected to further ion exchange chromatography, preferably using Q Sepharose. Antibody containing protein peaks are pooled and dialyzed against an appropriate solution or buffer, for instance, PBS.

Humanized antibodies and fragments thereof according to the invention can be tested for function by one or a combination of standard methods. Preferred tests assay for inhibition of TF function. A preferred method is what is sometimes referred to herein as a "standard prothrombin time" assay or related phrase. The standard prothrombin time (PT) assay typically involves at least one and preferably all of the following steps:

a) combining TF and factor VIIa to form a binding complex, b) contacting the binding complex with factor X (or factor IX) under conditions conducive to forming factor Xa (or factor IXa), c) contacting the factor Xa with prothrombin to produce thrombin, preferably in the presence of factor Va and lipids.

A preferred source of the TF for conducting the standard PT assay is commercially available as Innovin. A preferred source for the blood factors is a human plasma preparation called Ci-Trol Coagulation Control.

The humanized antibodies and fragments thereof provided herein can be readily tested in the assay. An aliquot of the purified antibody or fragment, preferably about 200 nM to about 2000 nM, is added to the method, preferably before step a) although addition at other points in the assay may be preferred for some applications. Typically, the humanized antibody or fragment is added to the Ci-Trol Coagulation Control followed by addition of the TF.

Highly preferred humanized antibodies and fragments thereof including whole IgG, Fab, Fab', F(ab)$_2$, and single chain antibodies (comprising the antigen binding variable regions of the humanized antibodies) will increase blood clotting time by at least about 5 seconds when present in the standard assay at a concentration of at least about 1 nM to about 20 nM, preferably about 5 nM to about 15 nM, more preferably about 10 nm in the assay. A typical control is a standard PT assay performed without adding any antibody of fragment. Additionally preferred antibodies and fragments of the invention achieve at least about 90% inhibition of TF-dependent coagulation, preferably at least about 95% inhibition or greater when compared to the control. A specific example of the standard PT assay is described in Examples 5 and 11.

Although a range of therapeutic anti-coagulant compositions of the invention have been described above, other compositions that include the humanized antibodies and fragments thereof are contemplated. For example, such antibodies and fragments may be used as the sole therapeutic agent or in combination with one or more other humanized antibodies or fragments to achieve a desired outcome. Such antibodies and fragments may also be used in combination with other antibodies, particularly human monoclonal antibodies reactive with other markers on cells responsible for the disease.

A wide spectrum of important uses for the present antibodies and fragments have been described above e.g., use to detect native TF in a biological sample, use to detect and purify cells expressing TF, and use to prevent or treat medical conditions such as undesired blood coagulation in a human patient. In practice, the humanized antibodies can be used as separately administered compositions given in conjunction with other anti-clotting agents including aspirin, coumadin, heparin, hirudin, or hirulog. Also envisioned is co-administration with anti-platelet (e.g., ReoPro, Integrilin, Aggrestat, Plavix, and/or Ticlid) and/or thrombolytic agents (e.g., tissue plasminogen activator, strepokinase and urokinase).

In embodiments in which the therapeutic anti-coagulant compositions described herein include one or more humanized antibodies or fragments, that composition may include a solution of the antibody or a cocktail thereof dissolved in an acceptable carrier, preferably an aqueous carrier. A variety of aqueous carriers have already been referenced such as water, buffered water, 0.4% saline, 0.3% glycine and the like. These solutions are preferably sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjustment agents and the like, for example sodium acetate, sodium chloride, potassium chloride, calcium chloride, sodium lactate, etc. The concentration of antibody in these formulations can vary widely, for example from less than about 0.5%, usually at or at least about 1% to as much as 15 or 20% by weight and will be selected primarily based on fluid volumes, viscosities, etc., in accordance with the particular mode of administration selected. See generally, Remington's Pharmaceutical Sciences, supra.

If desired, the therapeutic anti-coagulant compositions described herein can be lyophilized for storage and reconstituted in a suitable carrier prior to use. This technique has been shown to be effective with conventional immune globulins. Any suitable lyophilization and reconstitution techniques can be employed. It will be appreciated by those skilled in the art that lyophilization and reconstitution can lead to varying degrees of antibody activity loss (e.g., with conventional immune globulins, IgM antibodies tend to have greater activity loss than IgG antibodies) and that use levels may have to be adjusted to compensate.

For some prophylactic applications, it will be helpful to administer the therapeutic anti-coagulant compositions to a patient not already in a detectable disease state to enhance the patient's resistance to the disease. Such an amount is defined to be a "prophylactically effective dose". In this use, the precise amounts again depend upon the patient's state of health and general level of immunity, but generally range from 0.1 to 25 mg per dose, especially 0.5 to 2.5 mg per patient. A preferred prophylactic use is for the prevention of undesired blood clotting following a planned invasive medical procedure.

As discussed, the invention also features kits that include subject antibodies or fragments thereof. In one embodiment, the humanized antibodies or fragments thereof can be supplied for use against or in the detection of TF antigen. Thus, for instance, one or more humanized antibodies, fragments thereof, or single chain antibodies may be provided, usually in a lyophilized form in a container. Such antibodies, fragments, or single chain antibodies, which may be conjugated to a previously mentioned label or toxin, or unconjugated, are included in the kits with buffers, such as Tris, phosphate, carbonate, etc., stabilizers, biocides, inert proteins, e.g., serum albumin, or the like. Generally, these materials will be present in less than about 5% by weight based on the amount of active antibody, and usually present in total amount of at least about 0.001% wt. based again on the antibody concentration. Frequently, it will be desirable to include an inert extender or excipient to dilute the active ingredients, where the excipient may be present in from about 1 to 99% wt. of the total composition. Where a second antibody capable of binding to the chimeric antibody is employed in an assay, this will usually be present in a separate vial. The second antibody is typically conjugated to a label and formulated in an analogous manner with the antibody formulations described above. The kit will generally also include a set of instructions for use.

As discussed, the invention also provides a variety of methods of inhibiting blood coagulation in a mammal, preferably a primate such as a human patient.

For example, in one embodiment, the methods include administering to the mammal a therapeutically effective amount of at least one of, preferably one, two or three of the humanized antibodies provided herein or a fragment thereof that binds specifically to human tissue factor (TF) to form a complex. Typically, factor X or factor IX binding to TF or TF:FVIIa and activation by TF:FVIIa thereto is inhibited. In most embodiments, the methods further include forming a specific complex between the antibody and the TF to inhibit the blood coagulation.

Also provided are methods of inhibiting blood coagulation in a mammal that include administering to the mammal, a therapeutically effective amount of the humanized antibodies disclosed herein or a fragment thereof. Typical antibodies and fragments bind specifically to human tissue factor (TF) to form a complex, and further wherein factor X or factor IX binding to TF or TF:FVIIa and activation by TF:FVIIa thereto is inhibited. In most embodiments, the methods further include forming a specific complex between the antibody and the TF to inhibit the blood coagulation.

In a more specific example, the invention provides methods of inhibiting blood coagulation in a mammal that include administering to the mammal, a therapeutically effective amount of a humanized antibody or fragment thereof disclosed herein. Typically, the antibody binds specifically to human tissue factor (TF) to form a complex, and further wherein factor X or factor IX binding to TF or TF:FVIIa and activation by TF:FVIIa thereto is inhibited. Preferably, the humanized antibody or fragment includes, on the heavy chain, at least one of and preferably all of the following components:

a) a first CDR(CDR1) which is at least 95% identical to CDR1 amino acid sequence shown in FIG. 13B (SEQ ID NO: 8), b) a second CDR(CDR2) which is at least 95% identical to the CDR2 amino acid sequence shown in FIG. 13C (SEQ ID NOS: 9 or 101), c) a third CDR(CDR3) which is at least 95% identical to the CDR3 amino acid sequence shown in FIG. 13D (SEQ ID NO: 10), d) a first framework (FR1) which is at least 95% identical to the FR1 amino acid sequence shown in FIG. 13A (fragment of SEQ ID NO: 91) as "FR1 HC-08", e) a second framework (FR2) which is at least 95% identical to the FR2 amino acid sequence shown in FIG. 13A (fragment of SEQ ID NO: 91) as "FR2 HC-08", f) a third framework (FR3) which is at least 95% identical to the FR3 amino acid sequence shown in FIG. 13A (fragment of SEQ ID NO: 91) as "FR3 HC-08", g) a fourth framework (FR4) which is at least 95% identical to the FR4 amino acid sequence shown in FIG. 13A (fragment of SEQ ID NO: 91) as "FR4 HC-08".

In a more specific invention embodiment, the humanized antibody includes, on the light chain, at least one of, and preferably all of the following components:

h) a first CDR(CDR1) which is at least 95% identical to CDR1 amino acid sequence shown in FIG. 12B (fragment of SEQ ID NO: 2), i) a second CDR(CDR2) which is at least 95% identical to the CDR2 amino acid sequence shown in FIG. 12C (SEQ ID NO: 6), j) a third CDR(CDR3) which is at least 95% identical to the CDR3 amino acid sequence shown in FIG. 12D (SEQ ID NO: 7), k) a first framework (FR1) which is at least 95% identical to the FR1 amino acid sequence shown in FIG. 12A (fragment of SEQ ID NO: 79) as "FR1 LC-09", l) a second framework (FR2) which is at least 95% identical to the FR2 amino acid sequence shown in FIG. 12A (fragment of SEQ ID NO: 79) as "FR2 LC-09", m) a third framework (FR3) which is at least 95% identical to the FR3 amino acid sequence shown in FIG. 12A (fragment of SEQ ID NO: 79) as "FR3 LC-09", n) a fourth framework (FR4) which is at least 95% identical to the FR4 amino acid sequence shown in FIG. 12A (fragment of SEQ ID NO: 79) as "FR4 LC-09", o) a light chain constant region which is at least 95% identical to the amino acid sequence shown in FIG. 14A (SEQ ID NO: 97) or FIG. 15A (SEQ ID NO: 99); and p) a heavy chain constant region which is at least 95% identical to the amino acid sequence shown in FIG. 14B (SEQ ID NO: 98) or FIG. 15B (SEQ ID NO: 100).

In a more specific embodiment of the foregoing method, the humanized antibody or fragment thereof includes, on the heavy chain, at least one of and preferably all of the following components:

a) a first CDR(CDR1) identical to CDR1 amino acid sequence shown in FIG. 13B (SEQ ID NO: 8), b) a second CDR(CDR2) identical to the CDR2 amino acid sequence shown in FIG. 13C (SEQ ID NOS: 9 or 101), c) a third CDR(CDR3) identical to the CDR3 amino acid sequence shown in FIG. 13D (SEQ ID NO: 10), d) a first framework (FR1) identical to the FR1 amino acid sequence shown in FIG. 13A (fragment of SEQ ID NO: 91) as "FR1 HC-08", e) a second framework (FR2) identical to the FR2 amino acid sequence shown in FIG. 13A (fragment of SEQ ID NO: 91) as "FR2 HC-08", f) a third framework (FR3) identical to the FR3 amino acid sequence shown in FIG. 13A (fragment of SEQ ID NO: 91) as "FR3 HC-08", g) a fourth framework (FR4) identical to the FR4 amino acid sequence shown in FIG. 13A (fragment of SEQ ID NO: 91) as "FR HC-08";

and on the light chain:

h) a first CDR(CDR1) identical to CDR1 amino acid sequence shown in FIG. 12B (fragment of SEQ ID NO: 2), i) a second CDR(CDR2) identical to the CDR2 amino acid sequence shown in FIG. 12C (SEQ ID NO: 6), j) a third CDR(CDR3) identical to the CDR3 amino acid sequence shown in FIG. 12D (SEQ ID NO: 7), k) a first framework (FR1) identical to the FR1 amino acid sequence shown in FIG. 12A (fragment SEQ ID NO: 79) as "FR1 LC-09", l) a second framework (FR2) identical to the FR2 amino acid sequence shown in FIG. 12A (fragment SEQ ID NO: 79) as "FR2 LC-09", m) a third framework (FR3) identical to the FR3 amino acid sequence shown in FIG. 12A (fragment SEQ ID NO: 79) as "FR3 LC-09", n) a fourth framework (FR4) identical to the FR4 amino acid sequence shown in FIG. 12A (fragment SEQ ID NO: 79) as "FR4 LC-09", o) a light chain constant region which is identical to the amino acid sequence shown in FIG. 14A (SEQ ID NO: 79) or FIG. 15A (SEQ ID NO: 99), and p) a heavy chain constant region which is identical to the amino acid sequence shown in FIG. 14B (SEQ ID NO: 98) or FIG. 15B (SEQ ID NO: 100).

The invention also provides for a variety of methods of detecting tissue factor (TF) in a biological sample. In one embodiment, the method includes contacting a biological sample with the humanized antibodies or fragments thereof disclosed herein under conditions conducive to forming a complex and detecting the complex as being indicative of the TF in the biological sample.

All documents mentioned herein are fully incorporated by reference in their entirety.

EXEMPLIFICATION

The following non-limiting examples are illustrative of the invention. In the following examples and elsewhere the antibodies H36 and H36.D2 are referred to. Those antibodies are the same antibody as H36.D2.B7, but H36 is derived from the mother clone, and H36.D2 is obtained from the primary clone, whereas H36.D2.B7 is obtained from the secondary clone. No differences have been observed between those three clones with respect to ability to inhibit TF or other physical properties. In general usage, H36 is often used to indicate anti-TF antibody produced by any of these clones or related cell lines producing the antibody.

Example 1

Preparation and Cloning of Anti-rHTF Monoclonal Antibodies

Monoclonal antibodies against rhTF were prepared as follows.

A. Immunization and Boosts

Five female BALB/c mice were immunized with 10 μg each of lipidated, purified rhTF. The mice were initially sensitized intraperitoneally using Hunter's Titermax adjuvant. Three final boosts were administered in 0.85% NaCl. Boosts were 2, 5.5, and 6.5 months post initial sensitization. All boosts were given intraperitoneally, except the first which was subcutaneous. The final boost was given 3 days prefusion and 20 μg was administered.

B. Fusion of Mouse Spleen Lymphocytes with Mouse Myeloma Cells

Lymphocytes from the spleen of one rhTF immunized BALB/c mouse was fused to X63-Ag8.653 mouse myeloma cells using PEG 1500. Following exposure to the PEG, the cells were incubated for one hour in heat inactivated fetal bovine serum at 37° C. The fused cells were then resuspended in RPMI 1640 and incubated overnight at 37° C. with 10% $CO_2$. The cells were plated the next day using RPMI 1640 and supplemented with macrophage culture supernatant.

C. ELISA Development

Plates for the ELISA assay were coated with 100 microliters of recombinant tissue factor (0.25 μg/ml) in a carbonate-based buffer. All steps were performed at room temperature. Plates were blocked with BSA, washed, and then the test samples and controls were added. Antigen/antibody binding was detected by incubating the plate with goat anti-mouse HRP conjugate (Jackson ImmunoResearch Laboratories) and then using an ABTS peroxidase substrate system (Kirkegaard and Perry Laboratories). Absorbance was read on an automatic plate reader at a wavelength of 405 nm.

D. Stabilization of rhTF Hybridoma Cell Lines

Two weeks after fusion, screening of hybridoma colonies by specific rhTF ELISA was started. Screening for new colonies continued for three weeks. The positive clones were tested every one to two weeks for continued antibody production until fifteen stable clones were frozen down.

E. Primary and Secondary Cloning

Limiting dilution cloning was performed on each of the positive stable hybridomas to obtain primary clones. The cells were thawed, grown in culture for a short period of time, and then diluted from 10 cells/well to 0.1 cells/well. Primary clones were tested by anti-rhTF ELISA and five to six positive clones were expanded and frozen.

Secondary clone of anti-rhTF antibody, H36.D2.B7, was obtained from primary clone, H36.D2, prepared and stored in liquid nitrogen as described above. Four different dilutions, 5 cells/well, 2 cells/well, 1 cell/well, 0.5 cells/well of the primary clone were prepared in 96-wells microtiter plates to start the secondary cloning. Cells were diluted in IMDM tissue culture media containing the following additives: 20% fetal bovine serum (FBS), 2 mM L-glutamine, 100 units/ml of penicillin, 100 μg/ml of streptomycin, 1% GMS-S, 0.075% $NaHCO_3$. To determine clones that secrete anti-rhTF antibody, supernatants from five individual wells of the 0.2 cells/well microtiter plate were withdrawn after two weeks of growth and tested for the presence of anti-rhTF antibody by ELISA assays as described above. All five clones showed positive results in the ELISA assay, with H36.D2.B7 being the best antibody producer. All five clones were adapted and expanded in RPMI media containing the following additive: 10% FBS, 2 mM L-glutamine, 100 units/ml of penicillin, 100 μg/ml of streptomycin, 1% GMS-S, 0.075% $NaHCO_3$, and 0.013 mg/ml of oxalaacetic acid. H36.D2.B7 was purified by Protein A affinity chromatography from the supernatant of cell culture and was tested for its ability to inhibit TF:VIIa in a FX activation assay. The results indicated that H36.D2.B7 had the same inhibition as H36.D2 antibody. All cells were stored in liquid nitrogen.

F. Isolation of Total RNA from H36.D2.B7

269 μg of total RNA was isolated from $2.7 \times 10^5$ H36.D2.B7 hybridoma cells. The isolation of total RNA was performed as described in the RNeasy Midi Kits protocol from Qiagen. The RNA sample was stored in water at −20° C. until needed.

G. cDNA Synthesis and Cloning of Variable Regions of H36.D2.B7 Gene

To obtain the first strand of cDNA, a reaction mixture containing 5 μg of total RNA isolated as above, back primers JS300 (all primers are identified below) for the heavy chain (HC) and OKA 57 for the light chain (LC), RNase inhibitor, dNTP's, DTT, and superscript II reverse transcriptase, was prepared and incubated at 42° C. for 1 hour. The reaction tube is then incubated at 65° C. for 15 minutes to stop the transcription. After cooling down, five units of RNase H were then added and the reaction was allowed to incubate at 37° C. for 20 minutes. The cDNA sample was stored at −70° C. until needed.

PCR (polymerase chain reaction) was conducted separately to clone the variable regions of both HC and LC of anti-rhTF, H36.D2.B7 from the cDNA made as above (nucleic acid and amino acid sequences of those HC and LC variable regions set forth in FIGS. 1A and 1B). Three rounds of PCR were conducted. Round 1: PCR was run for 35 cycles at 96° C., 53° C. and 72° C. using front primer JS002 and back primer JS300 for HC. For LC front primer JS009 and back primer OKA 57 were used and PCR was rune for 35 cycles at 96° C., 63° C. and 72° C. Round 2: PCR of both HC and LC was rune the same as in Round 1 with the exception that pMC-18 was used for HC front primer and pMC-15 for LC front primer. Round 3: PCR was run for 30 cycles at 96° C., 60-65° C. and 72° C. using H36HCF and H36HCR primers for HC. For LC, PCR was run for 30 cycles at 96° C., 58° C. and 72° C. using H36LCF and H36LCR primers.

The following primers were used for cloning H36.D2.B7 variable regions of HC and LC.

OKA 57:

(SEQ ID NO: 17)

5'-GCACCTCCAGATGTTAACTGCTC-3'

JS300:

(SEQ ID NO: 18)

5'-GAARTAVCCCTTGACCAGGC-3'

JS009:

(SEQ ID NO: 19)

5'-GGAGGCGGCGGTTCTGACATTGTGMTGWCMCARTC-3'

-continued

JS002:
(SEQ ID NO: 20)
5'-ATTTCAGGCCCAGCCGGCCATGGCCGARGTYCARCTKCARCARY
C-3' pMC-15:
(SEQ ID NO: 21)
5'-CCCGGGCCACCATGKCCCCWRCTCAGYTYCTKG-3' pMC-18:
(SEQ ID NO: 22)
5'-CCCGGGCCACCATGGRATGSAGCTGKGTMATSCTC-3'

H36HCF:
(SEQ ID NO: 23)
5'-ATATACTCGCGACAGCTACAGGTGTCCACTCCGAGATCCAGCTGCAG
CAGTC-3'

H36HCR:
(SEQ ID NO: 24)
5'-GACCTGAATTCTAAGGAGACTGTGAGAGTGG-3'

H36LCF:
(SEQ ID NO: 25)
5'-TTAATTGATATCCAGATGACCCAGTCTCC-3'

H36LCR:
(SEQ ID NO: 26)
TAATCGTTCGAAAAGTGTACTTACGTTTCAGCTCCAGCTTGGTCC wherein in the above SEQ ID NOS: 17 through 26: K is G or T; M is A or C; R is A or G; S is C or G; V is A, C or G; W is A or T; Y is C or T.

Example 2

Binding Activity of Antibodies of the Invention

Antibodies of the invention as prepared in Example 1 above were employed. The rhTF molecule was expressed in *E. coli* and purified by immunoaffinity chromatography in accordance with standard methods (see Harlow and Lane, supra, Ausubel et al. supra). Antibody association ($K_a$) and dissociation ($K_d$) constants were determined by ELISA and surface plasmon resonance (i.e., BIACore) assays (see e.g., Harlow and Lane, supra; Ausubel et al. supra; Altschuh et al., *Biochem.*, 31:6298 (1992); and the BIAcore method disclosed by Pharmacia Biosensor). For BIACore assays, rhTF was immobilized on a biosensor chip in accordance with the manufacturer's instructions. Constants for each antibody were determined at four antibody concentrations (0.125 nM, 0.25 nM, 0.5 nM, and 1 nM).

Protein concentrations were determined by standard assay (M. M. Bradford, *Anal Biochem.*, 72:248 (1976)) using Bovine Serum Albumin as a standard and a commercially available dye reagent (Bio-Rad).

FIG. 2 shows association and disassociation constants for each anti-TF antibody. Antibody H36 exhibited the highest association rate ($K_a=3.1\times10^{10}$ M$^{-1}$) and the lowest disassociation rate ($K_d=3.2\times10^{-11}$ M) of any of the anti-TF antibodies tested.

Example 3

FXa-Specific Substrate Assay

In general, the experiments described herein were conducted using rhTF lipidated with phosphatidycholine (0.07 mg/ml) and phosphatidylserine (0.03 mg/ml) at a 70/30 w/w ratio in 50 mM Tris-HCl, pH 7.5, 0.1% bovine serum albumin (BSA) for 30 minutes at 37° C. A stock solution of preformed TF:FVIIa complex was made by incubating 5 nM of the lipidated rhTF and 5 nM of FVIIa for 30 minutes at 37° C. The TF:FVIIa complex was aliquoted and stored at −70° C. until needed. Purified human factors VII, VIIa, and FX were obtained from Enyzme Research Laboratories, Inc. The following buffer was used for all FXa and FVIIa assays: 25 mM Hepes-NaOH, 5 mM CaCl$_2$, 150 mM NaCl, 0.1% BSA, pH 7.5.

Monoclonal antibodies were screened for capacity to block TF:VIIa-mediated activation of FX to FXa. The FX activation was determined in two discontinuous steps. In the first step (FX activation), FX conversion to FXa was assayed in the presence of Ca$^{+2}$. In the second step (FXa activity assay), FX activation was quenched by EDTA and the formation of FXa was determined using a FXa-specific chromogenic substrate (S-2222). The S-2222 and S-2288 (see below) chromogens were obtained from Chromogenix (distributed by Pharmacia Hepar Inc.). FX activation was conducted in 1.5 ml microfuge tubes by incubating the reaction with 0.08 nM TF:VIIa, either pre-incubated with an anti-rhTF antibody or a buffer control. The reaction was subsequently incubated for 30 minutes at 37° C., then 30 nM FX was added followed by an additional incubation for 10 minutes at 37° C. FXa activity was determined in 96-well microtiter plates. Twenty microliters of sample was withdrawn from step one and admixed with an equal volume of EDTA (500 mM) in each well, followed by addition of 0.144 ml of buffer and 0.016 ml of 5 mM S-2222 substrate. The reaction was allowed to incubate for an additional 15-30 minutes at 37° C. Reactions were then quenched with 0.05 ml of 50% acetic acid, after which, absorbance at 405 nm was recorded for each reaction. The inhibition of TF:FVIIa activity was calculated from OD$_{405nm}$ values in the experimental (plus antibody) and control (no antibody) samples. In some experiments, an anti-hTF antibody, TF:FVIIa, and FX were each added simultaneously to detect binding competition. FIG. 3 shows that the H36.D2 MAb (in bold) inhibited TF:FVIIa activity toward FX to a significantly greater extent (95%) than other anti-rHTF Mabs tested.

Example 4

FVIIa-Specific Substrate Assay

Monoclonal antibodies were further screened by an FVIIa specific assay. In this assay, 5 nM lipidated rhTF was first incubated with buffer (control) or 50 nM antibody (experimental) in a 96-well microtiter plate for 30 minutes at 37° C., then admixed with 5 nM purified human FVIIa ($V_T$=0.192 ml), followed by 30 minutes incubation at 37° C. Eight microliters of a 20 mM stock solution of the FVIIa specific substrate S-2288 was then added to each well (final concentration, 0.8 mM). Subsequently, the reaction was incubated for one hour at 37° C. Absorbance at 405 nm was then measured after quenching with 0.06 ml of 50% acetic acid. Percent inhibition of TF: FVIIa activity was calculated from OD$_{405nm}$ values from the experimental and control samples.

FIG. 4 shows the H36 antibody did not significantly block TF:FVIIa activity toward the S-2288 substrate when the antibody was either pre-incubated with TF (prior to FVIIa addition) or added to TF pre-incubated with FVIIa (prior to adding the antibody). This indicates that H36 does not interfere with the interaction (binding) between TF and FVIIa, and that H36 also does not inhibit TF:FVIIa activity toward a peptide substrate.

Example 5

Prothrombin Time (PT) Assay

Calcified blood plasma will clot within a few seconds after addition of thromboplastin (TF); a phenomenon called the "prothrombin time" (PT). A prolonged PT is typically a useful indicator of anti-coagulation activity (see e.g., Gilman et al. supra).

The H36.D2 antibody was investigated for capacity to affect PT according to standard methods using commercially available human plasma (Ci-Trol Control, Level I obtained from Baxter Diagnostics Inc.). Clot reactions were initiated by addition of lipidated rhTF in the presence of $Ca^{+2}$. Clot time was monitored by an automated coagulation timer (MLA Electra 800). PT assays were initiated by injecting 0.2 ml of lipidated rhTF (in a buffer of 50 mM Tris-HCl, pH 7.5, containing 0.1% BSA, 14.6 mM $CaCl_2$, 0.07 mg/ml of phosphatidylcholine, and 0.03 mg/ml of phosphatidylserine) into plastic twin-well cuvettes. The cuvettes each contained 0.1 ml of the plasma preincubated with either 0.01 ml of buffer (control sample) or antibody (experimental sample) for 1-2 minutes. The inhibition of TF-mediated coagulation by the H36.D2 antibody was calculated using a TF standard curve in which the log [TF] was plotted against log clot time.

FIG. 5 shows the H36.D2 antibody substantially inhibits TF-initiated coagulation in human plasma. The H36.D2 antibody increased PT times significantly, showing that the antibody is an effective inhibitor of TF-initiated coagulation (up to approximately 99% inhibition).

Example 6

FX and H36.D2 Antibody Compete For Binding to the TF:FVIIa Complex

Competition experiments were conducted between TF:FVIIa, FX and the H36.D2 antibody. FIG. 6A illustrates the results of an experiment in which a preformed TF:FVIIa complex (0.08 nM) was pre-incubated at 37° C. for 30 minutes in buffer including 0.02 nM, 0.04 nM, 0.08 nM and 0.16 nM of the H36.D2 monoclonal antibody, respectively. FX (30 nM) was then added to the TF:FVIIa and H36.D2 antibody mixture and the mixture allowed to incubate for an additional 10 minutes at 37° C. FX activation was quenched with EDTA as described previously. The FXa produced thereby was determined by the FXa-specific assay described in Example 3, above.

Figure 6B:
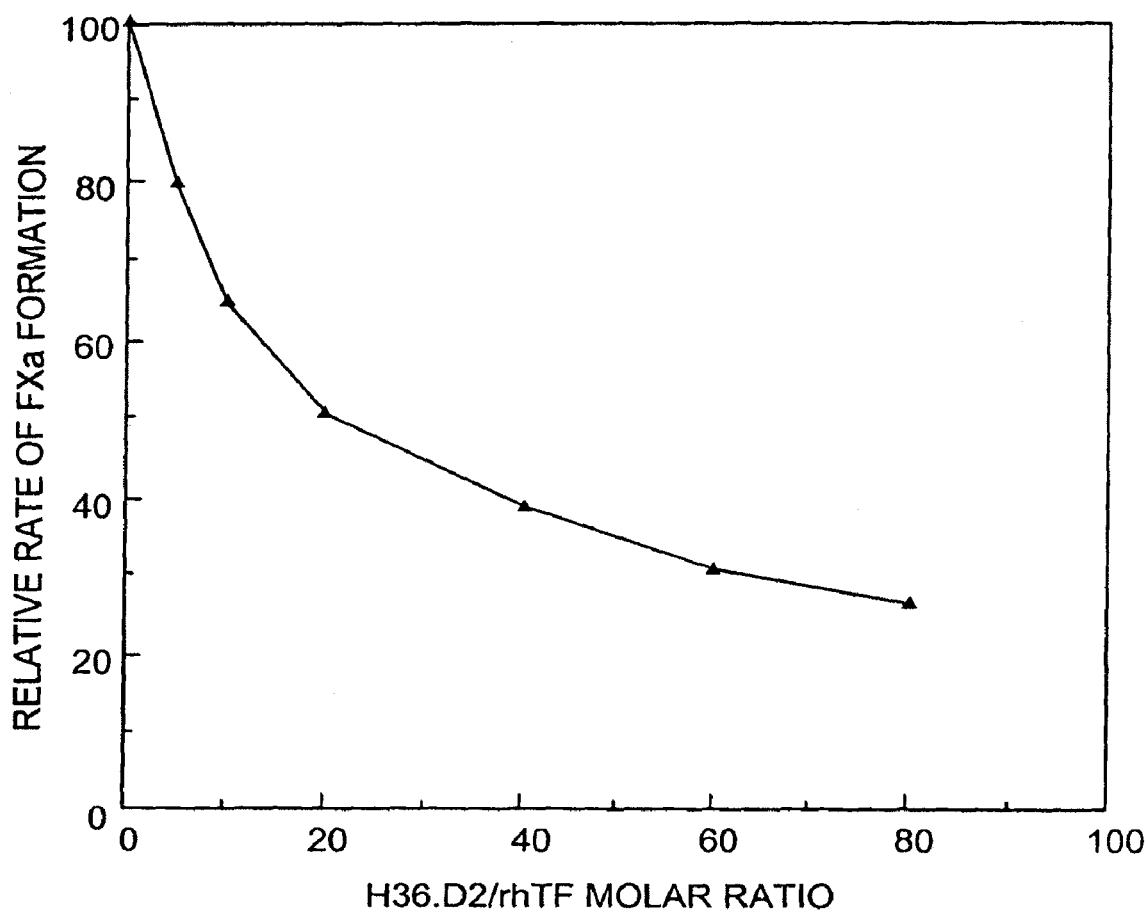

FIG. 6B shows the results of an experiment conducted along the lines just-described, except that the H36.D2 antibody, pre-formed TF:FVIIa, and FX were added simultaneously to start the FX activation assay.

The data set forth in FIGS. 6A and 6B show that the H36.D2 antibody and FX compete for binding to the pre-formed TF:FVIIa complex.

Example 7

Inhibition of TF Activity in Cell Culture

J-82 is a human bladder carcinoma cell line (available from the ATCC) which abundantly expresses native human TF as a cell surface protein. To see if the H36.D2 antibody could prevent FX from binding to native TF displayed on the cell surface, a J-82 FX activation assay was conducted in microtiter plates in the presence of FVII (see D. S. Fair et al., *J. Biol. Chem.*, 262:11692 (1987)). To each well, $2 \times 10^5$ cells was added and incubated with either 50 ng FVII, buffer (control sample) or the anti-TF antibody (experimental sample) for 2 hours at 37° C. Afterwards, each well was gently washed with buffer and 0.3 ml of FX (0.05 mg/ml) was added to each well for 30 minutes at room temperature. In some cases, the antibody was added at the same time as FX to detect binding competition for the native TF. Thereafter, 0.05 ml aliquots were removed and added to new wells in a 96-well microtiter plate containing 0.025 ml of 100 mM EDTA. FXa activity was determined by the FXa-specific assay as described in Example 3, above. Inhibition of TF activity on the surface of the J-82 cells was calculated from the $OD_{405nm}$ in the absence (control sample) and presence of antibody (experimental sample).

FIG. 7 shows that the H36.D2 antibody bound native TF expressed on J-82 cell membranes and inhibited TF-mediated activation of FX. These results indicate that the antibody competes with FX for binding to native TF displayed on the cell surface. Taken with the data of Example 8, below, the results also show that the H36.D2 antibody can bind a conformational epitope on native TF in a cell membrane.

Example 8

Specific Binding of the H36.D2 Antibody to Native rhTF

Evaluation of H36.D2 binding to native and non-native rhTF was performed by a simplified dot blot assay. Specifically, rhTF was diluted to 30 µg/ml in each of the following three buffers: 10 mM Tris-HCl, pH 8.0; 10 mM Tris-HCl, pH 8.0 and 8 M urea; and 10 mM Tris-HCl, pH 8.0, 8 M urea and 5 mM dithiothreitol. Incubation in the Tris buffer maintains rhTF in native form, whereas treatment with 8M urea and 5 nM dithiothreitol produces non-native (denatured) rhTF. Each sample was incubated for 24 hours at room temperature. After the incubation, a Millipore Immobilon (7×7 cm section) membrane was pre-wetted with methanol, followed by 25 mM Tris, pH 10.4, including 20% methanol. After the membranes were air-dried, approximately 0.5 µl, 1 µl, and 2 µl of each sample (30 µg/ml) was applied to the membrane and air-dried. After blocking the membrane by PBS containing 5% (w/v) skim milk and 5% (v/v) NP-40, the membrane was probed with H36.D2 antibody, followed by incubation with a goat anti-mouse IgG peroxidase conjugate (obtained from Jackson ImmunoResearch Laboratories, Inc.). After incubation with ECL Western Blotting reagents in accordance with the manufacturer's instructions (Amersham), the membrane was wrapped with plastic film (Saran Wrap) and exposed to X-ray film for various times.

FIG. 8A shows that the H36.D2 monoclonal antibody binds a conformational epitope on native TF in the presence of Tris buffer or Tris buffer with 8M urea (lanes 1 and 2). The autoradiogram was exposed for 40 seconds. However, when the native TF was denatured with 8M urea and 5 mM DTT, H36.D2 binding was significantly reduced or eliminated (lane 3). FIG. 8B shows an over-exposed autoradiogram showing residual binding of the H36.D2 antibody to non-native (i.e., denatured) rhTF. The over-exposure was for approximately 120 seconds. Treatment with 8M urea alone probably resulted in only partial denaturation of the native rhTF since the two disulfide bonds in TF are not reduced. It is also possible that the partially denatured TF may refold back to native confirmation during later blotting process when urea is removed. These results also clearly distinguish preferred antibodies of the invention which do not bind denatured TF from previously reported antibodies which do not selectively bind to a conformational epitope and bind to denatured TF (see U.S. Pat. No. 5,437,864 where in FIG. 18 Western Blot analysis shows binding to TF denatured by SDS).

Example 9

Humanization of Anti-Tissue Factor Antibody

The previous examples describe how to make and use a particular murine antibody called H36.D2 (sometimes also called H36 as discussed above). The present example shows how to make and use a humanized version of that antibody. A humanized H36 antibody has a variety of uses including helping to minimize potential for human anti-mouse antibody (HAMA) immunological responses. These and other undesired responses pose problems for use of the H36 antibody in human therapeutic applications.

A. Preparation of Chimeric Anti-Tissue Factor Antibody (cH36)

The H36 antibody described previously is an IgG2a murine antibody. H36 was first converted to a mouse-human chimeric antibody for clinical development. To do this, the heavy and light chain genes for H36 were cloned (see U.S. Pat. No. 5,986,065). The heavy chain variable region was fused to a human IgG4 constant (Fc) domain and the light chain variable region was fused to a human kappa light chain constant domain. The resulting IgG4K chimeric antibody was designated Sunol-cH36. For multiple uses of H36 or cH36 in patients with chronic diseases, a fully humanized cH36 is preferred so that it will decease or eliminate any human anti-mouse antibody immunological response. The humanization of cH36 is described below.

B. Humanization of cH36 Antibody

Humanization of the chimeric anti-tissue factor antibody cH36 was achieved by using a "best-fit" method. This method takes full advantage of the fact that a great number of human IgGs with known amino acid sequences are available in the public database. The individual frameworks of the mouse heavy and light variable regions in cH36 are compared with their corresponding human frameworks in the Kabat database (see http://immuno.bme.nwu.edu). The following criteria were used to select the desired human IgG frameworks for humanization: (1) The number of mismatched amino acids was kept as low as possible. (2) Amino acids inside the "vernier" zone (amino acids in this zone may adjust CDR structure and fine-tune the fit to antigen, see Foote, J. and Winter, G., J. of Mol. Bio. 224, (2) 487-499 [1992]) were left unchanged. (3) Conservative amino acid substitutions were favored when evaluating similar candidates. The matching program used for this comparison can be found in Kabat's home page at immuno.bme.nwu.edu (Johnson G, Wu T. "Kabat database and its application: Future directions." Nucleic Acids Res. (2001) 29:205-206). The program finds and aligns regions of homologies between the mouse sequences and human sequences in the Kabat's database. By using this unique best-fit method, it is anticipated that the humanized LC or HC variable region of the target IgG may have all the four FRs derived from as few as one human IgG molecule or to as many as four different human IgG molecules.

(i). Selection of Human IgG Kappa Light Chain Variable Region Frameworks

The amino acid sequence in each of the frameworks of cH36 LC was compared with the amino acid sequence in the corresponding FR in human IgG kappa light chain variable region in Kabat Database. The best-fit FR was selected based on the three criteria described above.

The amino acid sequence of human IgG kappa light chain variable region with a Kabat Database ID No. 005191 was selected for humanization of cH36 LC FR1. The amino acid sequence of human IgG kappa light chain variable region with a Kabat Database ID No. 019308 was selected for humanization of cH36 LC FR2. The following mutations were made in cH36 LC FR1 to match the amino acid sequence of a human IgG kappa light chain variable region with a Kabat Database ID No. 005191: Q11→L, L15→V, E17→D, S18→R. One mutation Q37→L was made cH36 LC FR2 to match the amino acid sequence of a human IgG kappa light chain variable region with a Kabat Database ID No. 019308 (see Table 1A for sequence information).

The amino acid sequence of a human IgG kappa light chain variable region with a Kabat Database ID No. 038233 was selected for humanization of cH36 LC FR3. The amino acid sequence of a human IgG kappa light chain variable region with a Kabat Database ID No. 004733 was selected for humanization of cH36 LC FR4. The following mutations were made in cH36 LC FR3 to match the amino acid sequence of a human IgG kappa light chain variable region with a Kabat Database ID No. 038233: K70→D, K74→T, A80→P, V84→A, N85→T. Two mutations A100→Q and L106→I were made cH36 LC FR4 to match the amino acid sequence of a human IgG kappa light chain variable region with a Kabat Database ID No. 004733 (see Table 1B for sequence information).

(ii). Selection of Human IgG Heavy Chain Variable Region Frameworks

The amino acid sequence in each of the frameworks of cH36 HC was compared with the amino acid sequence in the corresponding FR in human IgG heavy chain variable region in Kabat Database. The best-fit FR was selected based on the three criteria described above.

The amino acid sequence of a human IgG heavy chain variable region with a Kabat Database ID No. 000042 was selected for humanization of cH36 HC FR1. The amino acid sequence of a human IgG heavy chain variable region with a Kabat Database ID No. 023960 was selected for humanization of cH36 HC FR2. The following mutations were made in cH36 HC FR1 to match the amino acid sequence of a human IgG heavy chain variable region with a Kabat Database ID No. 000042: E1→Q, Q5→V, P9→G, L11→V, V12→K, Q19→R, T24→A. Two mutations H41→P and S44→G were made cH36 HC FR2 to match the amino acid sequence of a human IgG heavy chain variable region with a Kabat Database ID No. 023960 (see Table 2A for sequence information).

The amino acid sequence of a human IgG heavy chain variable region with a Kabat Database ID No. 037010 was selected for humanization of cH36 HC FR3. The amino acid sequence of a human IgG heavy chain variable region with a Kabat Database ID No. 000049 was selected for humanization of cH36 HC FR4. The following mutations were made in cH36 HC FR3 to match the amino acid sequence of a human IgG heavy chain variable region with a Kabat Database ID No. 037010: S76→T, T77→S, F80→Y, H82→E, N84→S, T87→R, D89→E, S91→T. One mutations L113→V was made cH36 HC FR2 to match the amino acid sequence of a human IgG heavy chain variable region with a Kabat Database ID No. 000049 (see Table 2B for sequence information).

Table 1A and 1B: Comparison of cH36 and Human Light Chain (LC) FR Sequences

TABLE 1A

| FR1 (23 AA) | FR2 (15 AA) | Names | |
|---|---|---|---|
| 1     10      20<br>DIQMTQSPASQSASLGESVTITC | 35      48<br>WYQQKPGKSPQLLIY | cH36-LC | (SEQ ID NO: 102) |
| DIQMTQSPASLSASVGDRVTITC | WYLQKPGKSPQLLIY | Human LC | (SEQ ID NO: 27) |

TABLE B

| FR3 (32 AA) | FR4 (10 AA) | Names | |
|---|---|---|---|
| 57 60     70     80     86<br>GVPSRFSGSGSGTKFSFKISSLQAEDFVNYYC | 98     107<br>FGAGTKLELK | cH36-LC | (fragment of SEQ ID NO: 72) |
| GVPSRFSGSGSGTDFSFTISSLQPEDFATYYC | FGQGTKLEIK | Human-LC | (SEQ ID NO: 28) |

Table 2A and 2B: Comparison of cH36 and Human Heavy Chain (HC) FR Sequences

TABLE 2A

| FR1 (30 AA) | FR2 (14 AA) | Names | |
|---|---|---|---|
| 1     10      20      29<br>EIQLQQSGPELVKPGASVQVSCKTSGYSFT | 36     44<br>WVRQSHGKSLEWIG | cH36-HC | (fragment of SEQ ID NO: 83) |
| QIQLVQSGGEVKKPGASVRVSCKASGYSFT | WVRQSPGKSLEWIG | Human-HC | (SEQ ID NO: 29) |

TABLE 2B

| FR3 (32 AA) | FR4 (11 AA) | Names | |
|---|---|---|---|
| 67     75     85     95<br>KATLTVDKSSTTAFMHLNSLTSDDSAVYFCAR | 107    117<br>WGQGTTLTVSS | cH36-HC | (fragment of SEQ ID NO: 83) |
| KATLTVDKSTSTAYMELSSLRSEDTAVYFCAR | WGQGTTVTVSS | Human-HC | (SEQ ID NO: 30) |

Once the decisions on the desired human frameworks were made, the following three techniques were used to achieve the desired amino acid substitutions in both the light and heavy chains: (1) Regular PCR was used for cloning, to introduce cloning or diagnostic endonuclease sites, and to change amino acid residues located at the ends of the variable regions. (2) PCR-based mutagenesis was used to change multiple amino acid residues at a time, especially when these residues were in the middle of the variable regions. (3) Site directed mutagenesis was used to introduce one or two amino acid substitutions at a time. Site directed mutagenesis was done following the protocol described in Stratagene's "QuickChange Site-Directed Mutagenesis Kit" (Catalog #200518).

After each step, the partially humanized clones were sequenced and some of these variable regions were later cloned into expression vectors. The plasmid tKMC180 was used to express LC mutants, and pJRS 355 or pLAM 356 vector was used to express HC mutants as IgG1 or IgG4, respectively. Some of these clones were then combined and expressed transiently in COS cells to determine the expression levels by ELISA.

The final fully humanized forms of the anti-TF heavy and light variable regions were cloned into what is sometimes referred to herein as a "mega vector" and transfected into CHO and NSO cells for IgG expression. Stable cell lines were then used to produce amounts of humanized anti-TF sufficient for analysis. The resulting humanized versions are 100% human in origin (when the CDR sequences are not considered). The humanized IgG4 kappa version is designated hFAT (humanized IgG Four Anti-Tissue Factor antibody) and the IgG1 kappa version is designated hOAT (humanized IgG One Anti-Tissue Factor antibody). These fully humanized versions of cH36 are intended for treating chronic indications, such as thrombosis, cancer and inflammatory diseases.

C. Humanization of Anti-TF Antibody Heavy Chain

1. PCR amplification and cloning into pGem T-easy of anti-TF mAb cH36 heavy chain (HC) variable region were performed using plasmid pJAIgG4TF.A8 (an expression vector for chimeric H36) as template and primers TFHC1s2 and TFHC1as2. Primer TFHC1s2 introduced a BsiW1 site upstream of the initiation codon and also an amino acid change E1 to Q in framework (FR) 1. Primer TFHC1as introduced an amino acid change L113 to V in FR4. This step resulted in the construct HC01.

2. PCR-based mutagenesis using the previous construct (HC01) and the following four primers generated construct HC02. Upstream PCR used primers TFHC1s2 and TFHC7 as. Downstream PCR used primers TFHC7s and TFHC1as2. Overlap PCR using upstream and downstream PCR products as templates and with primers TFHC1s2 and TFHC1as2 yielded HC02. The use of primers TFHC7s and TFHC7 as introduced two amino acid changes in FR2: H41 to P and S44 to G.

3. PCR-based mutagenesis using HC02 as template and the following four primers generated construct HC03. Upstream PCR used primers TFHC1s2 and TFHC5 as2. Downstream PCR used primers TFHC5s and TFHC1as2. PCR using upstream and downstream PCR products as templates and with primers TFHC1s2 and TFHC1as2 yielded HC03. The use of primers TFHC5s and TFHC5 as2 introduced three amino acid changes in FR3: T87 to R, D89 to E, and S91 to T. A Bgl II site was also introduced at position. 87.

4. PCR amplification was performed using primers TFHC2s and TFHC3 as and HC03 in pGem as template. TFHC2s sits upstream of the cloning site in pGem. TFHC3 as sits in framework 3 and introduces two amino acid changes in FR3: H82 to E and N84 to S. The resulting PCR band was cloned into pGem and then the proper size insert was digested with BsiWI and Bgl II. Cloning of this fragment into HC03 yields HC04.

5. PCR-based mutagenesis using HC04 as template and the following primers resulted in HC05. Upstream PCR used primers TFHC1s2 and TFHC6 as. Downstream PCR used primers TFHC6s and TFHC1as2. Mutagenic PCR using upstream and downstream PCR products as templates and with primers TFHC1s2 and TFHC1as2 yielded HC05. This step introduced the following amino acid changes in FR3: S76 to T, T77 to S, and F80 to Y.

6. PCR-based mutagenesis using HC05 as template and the following four primers generated HC06. Upstream PCR used primers TFHC2s and TFHC2 as2. Downstream PCR used primers TFHC3s2 and TFHC1as2. Amplification using TFHC2 as2 introduced an amino acid change in FR1: P9 to G. Primer TFHC3s2 changes Q19 to R and T24 to A. PCR using upstream and downstream PCR products as template and with primers TFHC1s2 and TFHC1as2 yielded HC06.

7. A point mutation from I to M in position 2 of FR1 was spontaneously introduced during construction of HC06. PCR amplification using HC06 as template and TFHC1s3 and TFHC1as2 as primers, corrected this erroneous substitution and also introduced an amino acid. change in FR1: Q5 to V. The resulting construct was HC07.

8. Construct HC08 was made by PCR-based mutagenesis using HC07 as template and the following primers. TFHC2s and TFHC2 as3 were used for the upstream product. The downstream product was previously amplified using TFHC1s3 and TFHC1as2 (see step 7). The use of primer TFHC2 as3 introduced two amino acid changes in FR1: L11 to V and V12 to K. A spontaneous point mutation resulted in a F to L change at position 64 in CDR2. Further screening and sequencing yielded construct HC08R1, which has the correct sequence of F at position 64 in CDR2.

9. Two constructs, HC11 and HC12, were generated by site-directed mutagenesis from HC07. Two complementary primers TFHC8sP and TFHC8asP were used along with HC07 as template to produce HC11 which contains three amino acid changes in FR1: G9 P, L11 to V, and V12 to K. Then, HC11 was methylated and column purified for the next round of site directed mutagenesis. PCR using HC11 as a template and the complementary primers TFHC9sL and TFHC0asL generated HC12 which has a mutation from V11 to L in FR1.

10. Construct HC09 was derived from HC12 by performing PCR using HC12 as a template and the complementary primers TFHC10sK and TFHC10asK. HC09 contains an amino acid change: K12 to V in FR1.

11. Construct HC10 was made from HC09. PCR using HC09 as a template and the complementary primers LV-1 and LV-2 resulted in the generation of HC10, which contains a mutation from L11 to V in FR1.

After each mutation step, the partially humanized or fully humanized clones were sequenced and some of these variable regions were later cloned into expression vectors. pJRS 355 or pLAM 356 vector was used to express HC mutants fused to Fc of human IgG1 or IgG4.

FIG. 13A summarizes steps 1-11 and shows incremental amino acid changes introduced into FR1-4. Except HC08, all other heavy chain mutants and cH36 contain F at position 64 in CDR2. HC08 has a mutation from F to L at position 64. FIGS. 13B-D show the heavy chain CDR sequences.

Primers Used for Heavy Chain Humanization

```
TFHC1s2
                                        (SEQ ID NO: 31)
5' TTTCGTACGTCTTGTCCCAGATCCAGCTGCAGCAGTC 3'

TFHC1as2
                                        (SEQ ID NO: 32)
5' AGCGAATTCTGAGGAGACTGTGACAGTGGTGCCTTGGCCCCAG 3'

TFHC7s
                                        (SEQ ID NO: 33)
5' GTGAGGCAGAGCCCTGGAAAGGGCCTTGAGTGGATTGG 3'

TFHC7as
                                        (SEQ ID NO: 34)
5' CCAATCCACTCAAGGCCCTTTCCAGGGCTCTGCCTCAC 3'

TFHC5s
                                        (SEQ ID NO: 35)
5' GCATCTCAACAGCCTGAGATCTGAAGACACTGCAGTTTATTTCTGT
G 3'

TFHC5as2
                                        (SEQ ID NO: 36)
5' CTGCAGTGTCTTCAGATCTCAGGCTGTTGAGATGCATGAAGGC 3'

TFHC3as
                                        (SEQ ID NO: 37)
5' GTCTTCAGATCTCAGGCTGCTGAGCTCCATGAAGGCTGTGGTG 3'

TFHC2s
                                        (SEQ ID NO: 38)
5' TACGACTCACTATAGGGCGAATTGG 3'

TFHC6s
                                        (SEQ ID NO: 39)
5' CTGTTGACAAGTCTACCAGCACAGCCTACATGGAGCTCAGCAG 3'

TFHC6as
                                        (SEQ ID NO: 40)
5' CTGCTGAGCTCCATGTAGGCTGTGCTGGTAGACTTGTCAACAG 3'

TFHC2as2
                                        (SEQ ID NO: 41)
5' GCACTGAAGCCCCAGGCTTCACCAGCTCACCTCCAGACTGCTGCAG
C 3'
```

TFHC3s2

(SEQ ID NO: 42)
5' CTGGGGCTTCAGTGCGGGTATCCTGCAAGGCTTCTGGTTACTCATTC
AC 3'

TFHC1s3

(SEQ ID NO: 43)
5' TCGTACGTCTTGTCCCAGATCCAGCTGGTGCAGTCTGGAGGTGAG
C 3'

TFHC2as3

(SEQ ID NO: 44)
5' GCACTGAAGCCCCAGGCTTCTTCACCTCACCTCCAGACTGCACC 3')

TFHC9sL (SEQ ID NO: 45)
5' GCAGTCTGGACCTGAGCTGAAGAAGCCTGGGG 3'

TFHC9asL (SEQ ID NO: 46)
5' CCCCAGGCTTCTTCAGCTCAGGTCCAGACTGC 3'

TFHC8sP (SEQ ID NO: 47)
5' GCTGGTGCAGTCTGGACCTGAGGTGAAGAAGCC 3'

TFHC8asP (SEQ ID NO: 48)
5' GGCTTCTTCACCTCAGGTCCAGACTGCACCAGC 3'

TFHC10sK (SEQ ID NO: 49)
5' GCAGTCTGGACCTGAGCTGGTGAAGCCTGGGGCTTC 3'

TFHC10asK (SEQ ID NO: 50)
5' GAAGCCCCAGGCTTCACCAGCTCAGGTCCAGACTGC 3'

LV-1

(SEQ ID NO: 51)
5' CAGTCTGGACCTGAGGTGGTGAAGCCTGGG 3'

LV-2

(SEQ ID NO: 52)
5' CCCAGGCTTCACCACCTCAGGTCCAGACTG 3'

D. Humanization of Anti-TF Antibody Light Chain

1. PCR amplification was performed using plasmid pJAIgG4TF.A8 (an expression vector for chimeric H36) as template and primers TFLC1s2.1 and TFLC1as2. This step introduced a cloning site, AgeI, upstream of the coding region. It also introduced the L106I mutation in FR4. This step yielded the construct LC03.

2. Site-directed mutagenesis was performed using complementary primers TFLC5s and TFLC5 as and LC03 as template. This step introduced the mutation Q37L in FR2 and added a PstI site for diagnostic purposes. This new construct is named LC04.

3. PCR amplification was performed using LC04 as template and primers TFHC2s and TFLC2as1. This step generated Fragment A that will be used in step 6. This step introduced Q11L and L15V mutations in FR1.

4. PCR amplification was performed using LC04 as template and primers TFLC1s2.1 and TFLC1asR. This introduced the KpnI site at the end of LC variable region. Cloning of this PCR fragment into pGEM yields pGEM04K that will be used in step 6.

5. PCR amplification was performed using LC04 as template and primers TFLC2s and TFLC4 as. This step generated Fragment C that will be used in step 6. Three mutations E17D, S18R in FR1 and A100Q in FR4 were introduced in this step.

6. PCR-based mutagenesis using Fragment A and Fragment C as templates and primers TFHC2s and TFLC4 as yielded Fragment D. Cloning of Fragment D into pGEM04K yielded the construct LC05.

7. PCR amplification was performed using pGEM04K as template and primers TFLC1s2.1 and TFLC4 as. This step generated Fragment H, which is then cloned into pGEM04K. This introduced the A100Q mutation in FR4 and the construct is named LC06.

8. PCR amplification was performed using LC06 as template and primers TFLC1s2.1 and TFLC3 as. This step generated Fragment I that will be used in step 10. This introduced the K70D and the K74T mutations in FR3.

9. PCR amplification was performed using LC06 as template and primers TFLC3s2 and TFLC4 as. This step generated Fragment F that will be used in step 10. This introduced the A80P mutation in FR3.

10. PCR using Fragment I and Fragment F as templates and primers TFLC1s2.1 and TFLC4 as yielded Fragment J. Cloning of Fragment J into pGEM yielded the construct LC07.

11. Site-directed mutagenesis was conduced using complementary primers TFLC08sds and TFLC08sdsa and LC07 as template. This step introduced the mutations V84A and N85T in FR3. This construct is named LC08.

12. The AgeI to EcoO109I fragment from LC05 containing the mutations Q11L, L15V, E17D, S18R and Q37L is cloned into LC08. This yielded the construct LC09.

13. Site-directed mutagenesis was conduced using LC09 as template and the complementary primers LC105 and LC103. This step introduced the T85N mutation in FR3 and yielded the construct LC10.

14. Site-directed mutagenesis was conducted using LC10 as template and the complementary primers LC115 and LC113. This step introduced the D70K mutation in FR3. This yielded the construct LC11.

15. Site-directed mutagenesis was conducted using LC11 as template and the complementary primers LC125a and LC123a. This step introduced the K42Q mutation in FR2. This yielded the construct LC12.

After each mutation step, the partially humanized or fully humanized LC clones were sequenced and some of these variable regions were later cloned into expression vector tKMC180.

FIG. 12A summarizes steps 1-15 and shows incremental amino acid changes introduced into FR1-4 of the light chain. FIGS. 12B-D show the light chain CDR sequences.

Oligonucleotide Primers Used for Light Chain Humanization

TFLC1as2:

(SEQ ID NO: 53)
5' TTCGAAAAGTGTACTTACGTTTGATCTCCAGCTTGGTCCCAG 3'

TFLC1s2.1:

(SEQ ID NO: 54)
5' ACCGGTGATATCCAGATGACCCAGTCTCC 3'

TFLC5s:

(SEQ ID NO: 55)
5' GGTTAGCATGGTATCTGCAGAAACCAGGG 3'

TFLC5as:

(SEQ ID NO: 56)
5' CCCTGGTTTCTGCAGATACCATGCTAACC 3'

TFHC2s:

(SEQ ID NO: 57)
5' TACGACTCACTATAGGGCGAATTGG 3'

TFLC2as1:

(SEQ ID NO: 58)
5' CCACAGATGCAGACAGGGAGGCAGGAGACTG 3'

-continued

TFLC1asR:
(SEQ ID NO: 59)
5' TTCGAAAAGTGTACTTACGTTTGATCTCCAGCTTGGTACCAGCACCG
AACG 3'

TFLC2s:
(SEQ ID NO: 60)
5' CCTGTCTGCATCTGTGGGAGATAGGGTCACCATCACATGC 3'

TFLC4as:
(SEQ ID NO: 61)
5' GATCTCCAGCTTGGTACCCTGACCGAACGTGAATGG 3'

TFLC3as:
(SEQ ID NO: 62)
5' GTAGGCTGCTGATCGTGAAAGAAAAGTCTGTGCCAGATCC 3'

TFLC3s2:
(SEQ ID NO: 63)
5' CACGATCAGCAGCCTACAGCCTGAAGATTTTGTAAATTATTACTGT
C 3'

TFLC08sds:
(SEQ ID NO: 64)
5' GCAGCCTACAGCCTGAAGATTTTGCAACTTATTACTGTCAACAA
G 3'

TFLC08sdsa:
(SEQ ID NO: 65)
5' CTTGTTGACAGTAATAAGTTGCAAAATCTTCAGGCTGTAGGCTG
C 3'

LC105:
(SEQ ID NO: 66)
5' CAGCAGCCTACAGCCTGAAGATTTTGCAAATTATTACTGTCAAC 3'

LC103:
(SEQ ID NO: 67)
5' GTTGACAGTAATAATTTGCAAAATCTTCAGGCTGTAGGCTGCTG 3'

LC115:
(SEQ ID NO: 68)
5' CAGTGGATCTGGCACAAAGTTTTCTTTCACGATCAGCAGC 3'

LC113:
(SEQ ID NO: 69)
5' GCTGCTGATCGTGAAAGAAAACTTTGTGCCAGATCCACTG 3'

LC125a:
(SEQ ID NO: 70)
5' CTGCAGAAACCAGGGCAATCTCCTCAGCTCCTG 3'

LC123a:
(SEQ ID NO: 71)
5' CAGGAGCTGAGGAGATTGCCCTGGTTTCTGCAG 3'

FIG. 14 shows hOAT (humanized cH36-IgG1) constant region sequences of the light (FIG. 14A) (SEQ ID NO: 97) and heavy chain (FIG. 14B) (SEQ ID NO: 98). FIG. 15 shows hFAT (humanized cH36-IgG4) constant region sequences of the light (FIG. 15A) (SEQ ID NO: 99) and heavy chain (FIG. 15B) (SEQ ID NO: 100). In each figure, the last amino acid residue of the framework 4 (FR4) variable region is connected to the first amino acid residue of the constant region for hOAT and hFAT.

Example 10

Expression and Purification of Humanized Anti-TF Antibodies

Figures 9A, 9B:
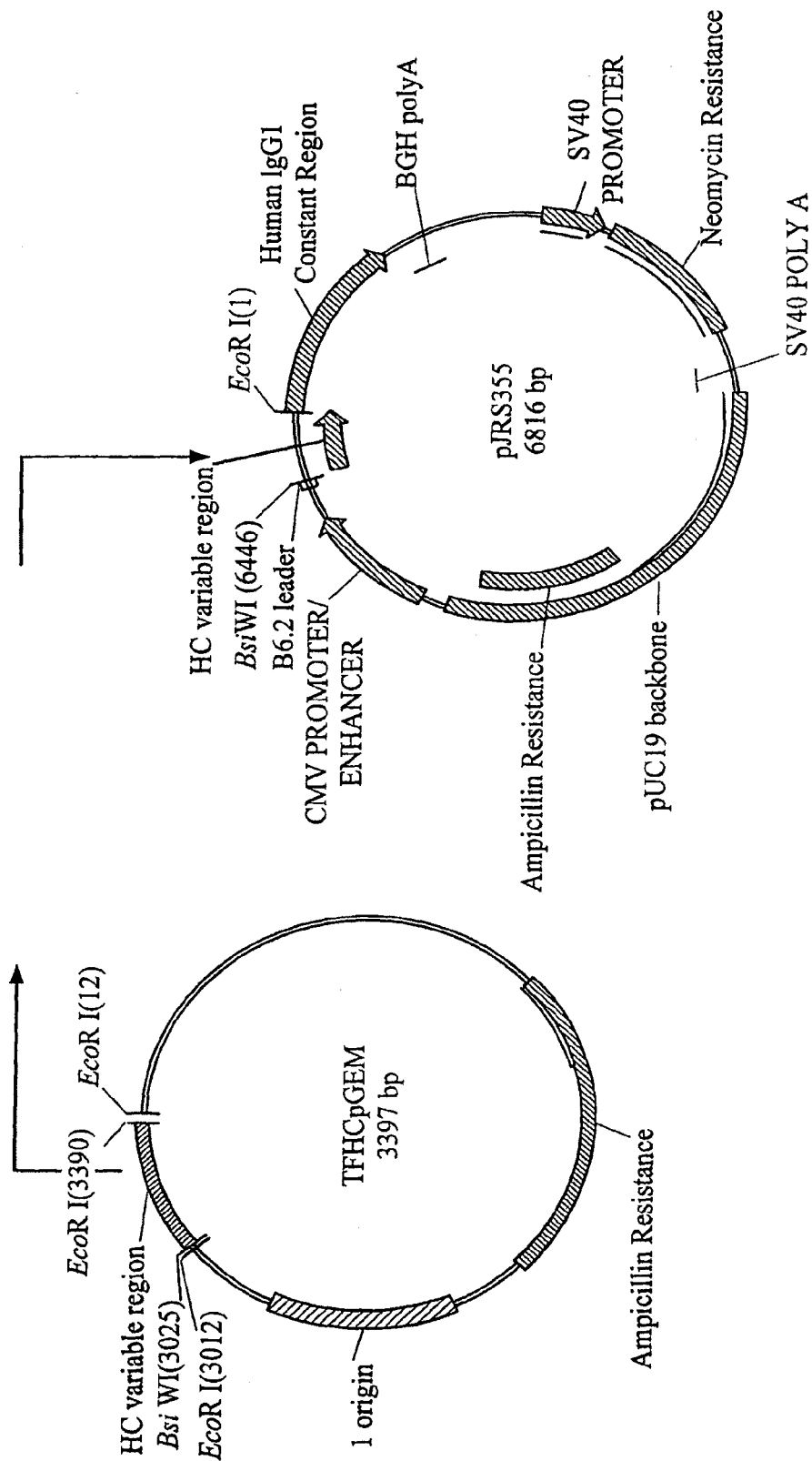
FIGS. 9A-B are drawings showing human IgG1-cH36 HC variable region cloning and expression vectors. HC cloning vector (9A) and HC expression vector (9B).
Figures 9C, 9D:
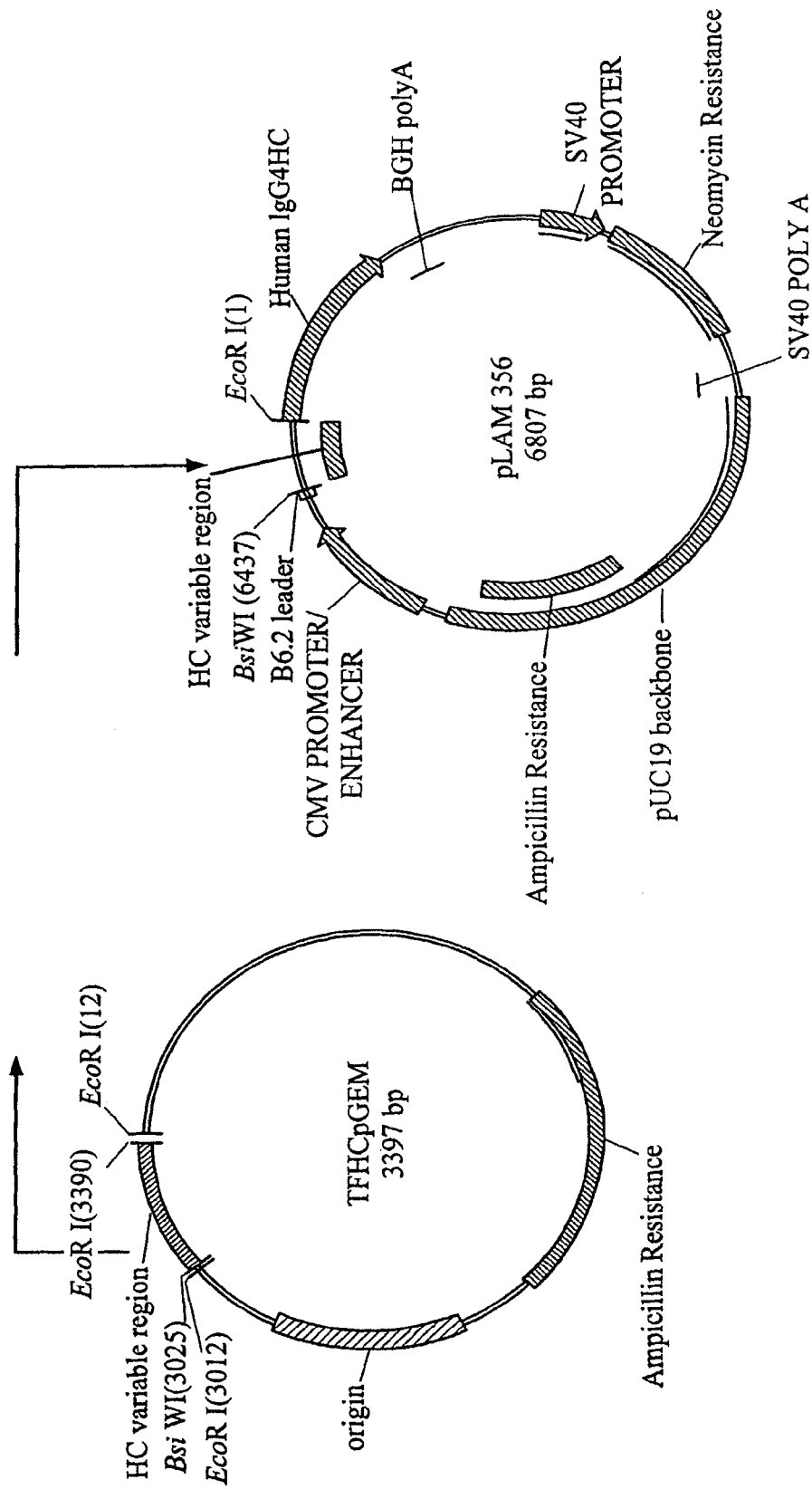
FIGS. 9C-D are drawings showing human IgG4-cH36 HC variable region cloning and expression vectors. HC cloning vector (9C) and HC expression vector (9D).
Figures 10A, 10B:
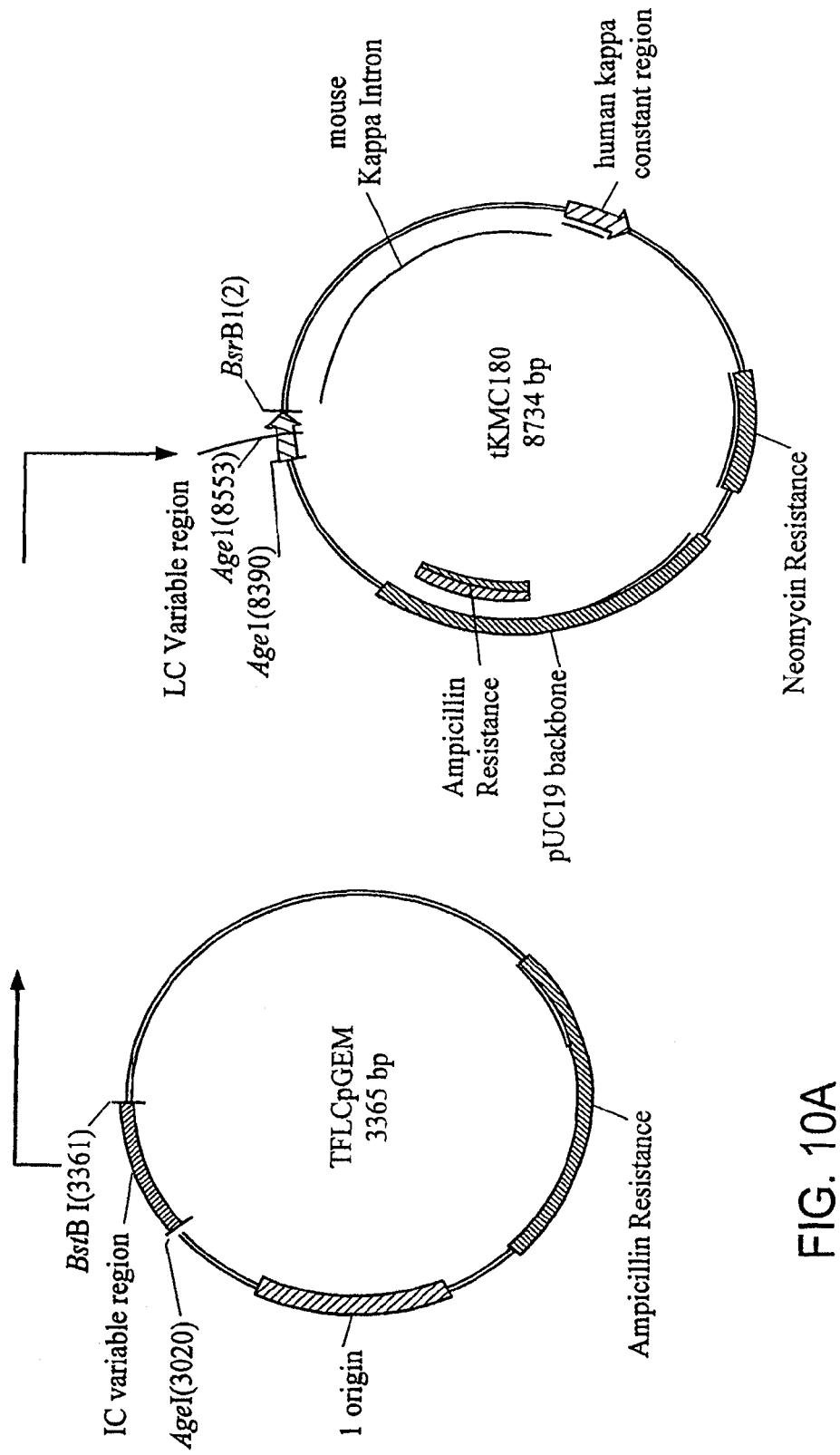
FIGS. 10A-B are drawings showing cH36 LC variable region cloning and expression vectors. LC cloning vector (10A) and LC expression vector (10B).

The partially humanized or fully humanized LC and HC clones were cloned into expression vectors. The plasmid tKMC180 (see FIGS. 10A-B) was used to express LC mutants fused to human kappa chain, and pJRS 355 (see FIGS. 9A-B) or pLAM 356 (see FIGS. 9C-D) vector was used to express HC mutants fused to Fc of human IgG1 or IgG4. Some combinations of the HC and LC clones were then co-transfected into COS cells. The transiently expressed IgGs in COS cells were assayed for the whole IgG production and binding to TF by ELISA.

The final fully-humanized forms of the anti-TF heavy and light variable regions (combination of HC08 and LC09) were cloned into Sunol's Mega expression vector (pSUN34, see FIG. 11) and transfected into CHO and NSO cells for IgG expression. Stably transfected cell lines producing the IgG4κ or IgG1κ humanized anti-TF antibody were cloned. The selected stable cell lines were then used to produce amounts of humanized anti-TF sufficient for analysis. The resulting humanized versions are approximately 95% human in origin (the CDR sequences are not considered). The humanized IgG4 kappa version is designated hFAT (humanized IgG Four Anti-Tissue Factor antibody) and the IgG1 kappa version is designated hOAT (humanized IgG One Anti-Tissue Factor antibody). These fully humanized versions of cH36 are intended for treating chronic indications, such as cancer and inflammatory diseases.

One of the NSO cell lines (OAT-NSO-P10A7) that expresses hOAT (combination of HC08 and LC09) was thawed and extended in 10 mL of IMDM medium supplemented with 10% FBS in a 15 mL tube and centrifuged. The cell pellet was resuspended in 10 mL of fresh media and passed to a T25 flask and incubated at 37° C. in 5% $CO_2$. In order to prepare a sufficient number of cells to inoculate a hollow fiber bioreactor, the cells were expanded to obtain a total of $6 \times 10^8$ cells. A bioreactor was set up as per manufacturer's instruction manual. The harvested cells were pelleted and resuspended in 60 mL of IMDM containing 35% FBS and injected into the extracapillary space of the bioreactor. Concentrations of glucose and lactate were monitored daily and the harvest material was centrifuged and pooled. The harvested material was tested for anti-TF antibody concentrations by ELISA assay. The pooled sample containing anti-TF antibody (hOAT) were then purified and analyzed as described below.

A. rProtein A Sepharose Fast Flow Chromatography

Recombinant humanized anti-TF monoclonal antibody consists of two light and two heavy chains. Heavy chain is a fusion of mouse variable region (unaltered or humanized as described above) and human IgG1 or IgG4 Fc domain, while light chain contains mouse variable region (unaltered or humanized as described above) and human κ domain. It is well established that human IgG Fc region has high affinity for Protein A or recombinant Protein A (rProtein A).

Harvest pools containing humanized anti-TF antibody (hOAT) were adjusted to pH 8.0±0.1 by adding 0.08 ml of 1 M Tris-HCl, pH 8.0 per ml of sample. Then the sample is filtered through low protein-binding 0.22 micron filters (e.g., Nalgene sterile disposable tissue culture filter units with polyethersulfone membrane from Nalge Nunc International, Cat. No. 167-0020). Following sample application, rProtein A column (from Pharmacia) is washed with 5 bed volumes of 20 mM Tris-HCl, pH 8.0 to remove unbound materials such as media proteins. Since the harvest medium contains high content of bovine serum, a stepwise pH gradient wash was used to remove bovine IgG from the column. The stepwise pH gradient was achieved by increasing the relative percentage of Buffer B (100 mM acetic acid) in Buffer A (100 mM sodium acetate). A typical pH stepwise wash employed 20%, 40%, and 60% Buffer B. Elute the column with 100% Buffer B and collect fractions based on $A_{280}$. The pooled fractions were adjusted to pH 8.5 with addition of 1 M Tris base.

B. Q Sepharose Fast Flow Chromatography

Anion ion exchange chromatography is very effective in separating proteins according to their charges. The eluted and pH-adjusted sample from rProtein A column was diluted with two volumes of water, and the pH is checked and adjusted to 8.5. The sample was then loaded to a 5 ml (1.6×2.5 cm) Q Sepharose Fast Flow equilibrated with 20 mM Tris-HCl, pH 8.5 and the column washed with (1) 5 bed volumes of 20 mM Tris-HCl, pH 8.5; and (2) 4 bed volumes of 20 mM Tris-HCl, pH 8.5 containing 100 mM NaCl. The IgG protein was then eluted with bed volumes of 20 mM Tris-HCl, pH 8.5 containing 500 mM NaCl. The protein peaks were pooled and buffer-exchanged into PBS using ultrafiltration device.

Using the same transfection, cell culture, and purification methods, hFAT was also produced and purified.

Example 11

Properties of Humanized Anti-TF Antibodies

A. Inhibition of TF Function by Humanized Anti-TF Antibody

One of the key properties of anti-TF antibodies is its ability to inhibit tissue factor-initiated blood coagulation. The purified hOAT and hFAT were measured for their ability to inhibit TF activity in a standard PT assay. PT assay is widely used to measure tissue factor-dependent blood clotting times. The principal of this assay is that tissue factor (TF) forms complex with factor VIIa in plasma. This complex then activates factor X to FXa; FXa then converts prothrombin to thrombin in the presence of factor Va and phospholipids. Thrombin eventually leads to formation of a blood clot. In standard PT assays, lipidated TF is added to plasma to initiate blood coagulation and the clotting is recorded by an Organon Teknika Coag-A-Mate Coagulation Analyzer or equivalent.

The anti-TF antibody, H36, inhibits human TF activity by a unique mechanism. It binds to TF (free or in complex with factor VIIa) in such a way that factor X and IX binding to TF:VIIa complex is prohibited, thus FX and FIX activation by TF:VIIa is blocked (see U.S. Pat. No. 5,986,065). In PT tests, the prolongation of clotting times anti-TF antibody added into human plasma is a clear indication that this TF-dependent coagulation is inhibited. The clotting time is related to the amount of TF activity. A TF standard curve is generated by measuring PT clotting times of serially diluted TF. From the data of TF standard curve, the inhibition of TF activity by anti-TF antibody is determined.

Reagents: Innovin (Cat No 68100-392) and Ci-Trol Coagulation Control, Level I (Cat No 68100-336) are obtained from VWR. Lipidated recombinant human TF was produced as described in Example 3.

Method: PT test is performed at 37 C using a Coagulation Analyzer. PT reaction is initiated by adding 0.2 ml of lipidated recombinant human tissue factor (e.g., Innovin) into 0.1 ml of human plasma (Ci-Trol Control Level I) containing 0.01 ml buffer (50 mM Tris-HCl, pH 7.5, 0.1% BSA) or anti-TF antibody.

1. Add purified water to a vial of Innovin according to manufacturer's instruction. Warm the reagent to 37° C. The reagent is stable for a few days if stored at 4-8° C.

2. Add 1 ml purified water to each vial of Ci-Trol. Mix to solubilize. If more one vials are used, combine them into one container (e.g., a 10 ml test tube). 1 ml Ci-Trol can run 5 assays (each assay uses 2×0.1 ml=0.2 ml). Ci-Trol can be stored on ice and last for a few hours.

3. From anti-TF antibody stock, make a series of anti-TF antibody solutions (200 nM to 1600 nM) with 50 mM Tris-HCl, pH 7.5, 0.1% BSA 4. Add 10 µl of 50 mM Tris-HCl, pH 7.5, 0.1% BSA or 10 µl of diluted anti-TF to each well of the twin-well cuvette that contains 0.1 ml of Ci-Trol. Use a pipette with 0.1 ml tip to mix each well. Make sure no air bubbles are in the well. Following mixing anti-TF (or buffer) with plasma (Ci-Trol), measure clotting times within 10 min by adding 0.2 ml of Innovin to the plasma.

5. For TF standard curve, first dilute Innovin (100% TF) to 20%, 10%, 5% and 2.5% with 50 mM Tris-HCl, pH 7.5, 0.1% BSA. Then PT assays were performed as in Step 4 but using diluted Innovin samples.

Table 3 is the summary of the effect of cH36, hOAT, and hFAT on PT clotting times. Compared to the data in Table 4, cH36, hFAT, and hOAT showed very potent inhibition of TF function. At a protein concentration of above 12.9 nM, all antibodies achieved about 95% inhibition. The results in Table 3 also indicate that humanization of anti-TF, cH36, by the method described above did not have any significant effect on cH36 inhibitory activity since both hFAT and hOAT showed very similar ability to inhibit TF-dependent blood coagulation as seen for cH36.

TABLE 3

Effect on Prothrombin Times by Chimeric (cH36) and Humanized) Anti-TF Antibodies (hFAT and hOAT)[#]

| Anti-TF Antibody Concentrations (nM) in PT Assays | PT Time (in seconds) | | |
|---|---|---|---|
| | cH36 | hOAT | hFAT |
| 0 | 12.2 | 12.2 | 12.2 |
| 6.45 | 14.9 | nd | nd |
| 9.7 | 17.8 | 16.5 | nd |
| 12.9 | 19.8 | 18.9 | 20.5 |
| 25.8 | 40 | 33.7 | 41.7 |
| 51.6 | 101.3 | 82.1 | 94.8 |

[#]All assays used the same 100% TF activity (concentration) sample as in Table 4.

TABLE 4

Clotting Times and Relative Tissue Factor Activities (Concentrations)

| Relative TF Activities (Concentrations) | PT Clotting Times (Seconds) |
|---|---|
| 100% (neat) | 11.90 |
| 20% | 13.225 |
| 10% | 14.675 |
| 5% | 16.700 |
| 2.5% | 20.000 |

B. Determination of Affinity Constants

The affinity of humanized anti-TF antibody for TF was determined by surface plasmon resonance (BIAcore from Pharmacia Biosensor) with recombinant human tissue factor covalently immobilized on a CM5 sensor chip. The affinity constants were the average data calculated from four anti-TF monoclonal antibody concentrations (0.125 nM, 0.25 nM, 0.5 nM, and 1 nM) by the BIAcore computer software. The results in Table 5 indicate that humanization of anti-TF, cH36, by the method described above did not have any significant effect on cH36 affinity for TF since both cH36 and hFAT have similar affinity for TF.

TABLE 5

Apparent Affinity and Dissociation Constants of Anti-TF Antibodies

| Anti-TF Antibody | Apparent $K_a$ (M$^{-1}$) | Apparent $K_d$ (M) |
|---|---|---|
| H36 | $1.56 \times 10^{10}$ | $6.4 \times 10^{-11}$ |
| cH36 | $7.94 \times 10^{9}$ | $1.26 \times 10^{-10}$ |
| hFAT | $2.99 \times 10^{9}$ | $3.35 \times 10^{-10}$ |

The invention has been described in detail with reference to preferred embodiments thereof. However, it will be appreciated that those skilled in the art, upon consideration of the disclosure, may make modification and improvements within the spirit and scope of the invention.

What is claimed is:

1. An anti-TF antibody comprising a light chain, wherein the light chain comprises:
   (a) CDR1 having the sequence of LASQTIDTWLA (SEQ ID NO: 116),
   (b) CDR2 having the sequence of AATNLAD (SEQ ID NO: 6),
   (c) CDR3 having the sequence of QQVYSSPFT (SEQ ID NO:7),
   (d) a first framework (FR1) comprising a sequence having at least 95% identity to SEQ ID NO:109,
   (e) a second framework (FR2) comprising a sequence having at least 95% identity to SEQ ID NO: 108;
   (f) a third framework (FR3) comprising a sequence having at least 95% identity to SEQ ID NO: 112, and
   (g) a fourth framework (FR4) comprising a sequence having at least 95% identity to a sequence selected from the group consisting of: SEQ ID SEQ ID NO: 110
and further comprising a heavy chain, wherein the heavy chain comprises:
   (h) CDR1 having the sequence of DYNVY (SEQ ID NO: 134),
   (i) CDR2 having the sequence of YIDPYNGITIYDQN-FKG (SEQ ID NO: 9) or CDR2 having the sequence of YIDPYNGITIYDQNLKG (SEQ ID NO: 101),
   (j) CDR3 having the sequence of DVTTALDF (SEQ ID NO:10),
   (k) a first framework (FR1) comprising a sequence having at least 95% identity to SEQ ID NO: 129;
   (l) a second framework (FR2) comprising a sequence having at least 95% identity to SEQ ID NO: 123;
   (m) a third framework (FR3) comprising a sequence having at least 95% identity to SEQ ID NO: 126; and
   (n) a fourth framework (FR4) comprising a sequence having at least 95% identity to SEQ ID NO: 122.

2. The antibody of claim 1 wherein the light chain comprises: FR1 comprising SEQ ID NO: 109, FR2 comprising SEQ ID NO: 108, FR3 comprising SEQ ID NO: 112 and FR4 comprising SEQ ID NO: 110.

3. The antibody of claim 1 wherein the heavy chain comprises: FR1 comprising SEQ ID NO: 129, FR2 comprising SEQ ID NO: 123, FR3 comprising SEQ ID NO: 126, and FR4 comprising SEQ ID NO: 122.

4. An anti-TF antibody comprising:
   (a) light chain CDR1 (LASQTIDTWLA) (SEQ ID NO: 116),
   (b) light chain CDR2 (AATNLAD) (SEQ ID NO: 6),
   (c) light chain CDR3 (QQVYSSPFT) (SEQ ID NO: 7),
   (d) light chain FR1 comprising SEQ ID NO: 109
   (e) light chain FR2 comprising SEQ ID NO: 108,
   (f) light chain FR3 comprising SEQ ID NO: 112,
   (g) light chain FR4 comprising SEQ ID NO: 110
   (h) heavy chain CDR1 (DYNVY) (SEQ ID NO: 134),
   (i) heavy chain CDR2 (YIDPYNGITIYDQNLKG) (SEQ ID NO: 101),
   (j) heavy chain CDR3 (DVTTALDF) (SEQ ID NO:10)
   (k) heavy chain FR1 comprising SEQ ID NO: 129,
   (l) heavy chain FR2 comprising SEQ ID NO: 123,
   (m) heavy chain FR3 comprising SEQ ID NO: 126, and
   (n) heavy chain FR4 comprising SEQ ID NO: 122.

5. The antibody of claim 4 wherein the antibody further comprises a light chain or heavy chain constant region wherein the constant region has an IgG1 or IgG4 isotype.

6. The antibody of claim 5 wherein the antibody further comprises a light chain constant region having a sequence as recited in SEQ ID NO: 97 and a heavy chain constant region having a sequence as recited in SEQ ID NO: 98.

7. The antibody of claim 4 wherein the antibody further comprises a light chain constant region having a sequence as recited in SEQ ID NO: 99 and a heavy chain constant region having a sequence as recited in SEQ ID NO: 100.

8. An anti-TF antibody comprising:
(a) three CDRs for a light chain wherein the CDRs are encoded by:

```
                                    (SEQ ID NO: 11)
(i)    CTGGCAAGTCAGACCATTGAT;
                                    (SEQ ID NO: 12)
(ii)   GCTGCCACCAACTTGGCAGAT; or
                                    (SEQ ID NO: 13)
(iii)  CAACAAGTTTACAGTTCT CCATTCACGT; and
```

(b) three CDRs for a heavy chain wherein the CDRs are encoded by:

```
                                    (SEQ ID NO: 14)
(i)         ACTGACTACAACGTGTAC;

(SEQ ID NO: 15)
(ii)        TATATTGATCCTTACAATGGTATTACTATC
            TACGACCAGAACTTCAAGGGC; or (SEQ ID NO: 16)
(iii)       GATGTGACTACGGCCCTTGACTTC; and
```

(c) a framework region for the light chain comprising:
  (i) a first framework (FR1) comprising a sequence having at least 95% identity to SEQ ID NO:109,
  (ii) a second framework (FR2) comprising a sequence having at least 95% identity to SEQ ID NO: 108;
  (iii) a third framework (FR3) comprising a sequence having at least 95% identity to SEQ ID NO: 112, and
  (iv) a fourth framework (FR4) comprising a sequence having at least 95% identity to SEQ ID NO: 110; and
(d) a framework region for the heavy chain comprising:
  (i) a first framework (FR1) comprising a sequence having at least 95% identity to SEQ ID NO: 129;
  (ii) a second framework (FR2) comprising a sequence having at least 95% identity to SEQ ID NO: 123;
  (iii) a third framework (FR3) comprising a sequence having at least 95% identity to SEQ ID NO: 126; and
  (iv) a fourth framework (FR4) comprising a sequence having at least 95% identity to SEQ ID NO: 122.

9. The antibody of claim 1 wherein the fragment is Fab, Fab', or F(ab)₂.

10. A method of inhibiting blood coagulation in a mammal comprising administering an effective amount of the antibody of claim 1 to the mammal to inhibit blood coagulation in the mammal.

11. A method for producing the humanized antibody of claim 1 or 4 comprising providing a host cell which comprises either:
(a) a first expression vector encoding the light chain of the humanized antibody or fragment thereof and a second expression vector encoding the heavy chain of the humanized antibody or fragment thereof, or
(b) a single expression vector encoding both the light chain and the heavy chain of the humanized antibody or fragment thereof, and
maintaining the host cell under growth conditions in which each chain is expressed.

12. The antibody made by the method of claim 11.

13. An anti-TF antibody comprising a light chain, wherein the light chain comprises:
(a) CDR1 having the sequence of LASQTIDTWLA (SEQ ID NO: 116);
(b) CDR2 having the sequence of AATNLAD (SEQ ID NO: 6);
(c) CDR3 having the sequence of QQVYSSPFT (SEQ ID NO:7);
(d) a first framework (FR1) which comprises a sequence of SEQ ID NO:109;
(e) a second framework (FR2) which comprises a sequence of SEQ ID NO: 108 or SEQ ID NO: 115;
(f) a third framework (FR3) which comprises a sequence selected from the group consisting of: SEQ ID NOs: 111-114; and
(g) a fourth framework (FR4) which comprises a sequence of SEQ ID NO: 107 or SEQ ID NO: 110;
and further comprising a heavy chain, wherein the heavy chain comprises:
(h) CDR1 having the sequence of DYNVY (SEQ ID NO: 134);
(i) CDR2 having the sequence of YIDPYNGITIYDQN-FKG (SEQ ID NO: 9) or CDR2 having the sequence of YIDPYNGITIYDQNLKG (SEQ ID NO: 101);
(j) CDR3 having the sequence of DVTTALDF (SEQ ID NO:10);
(k) a first framework (FR1) which has a sequence selected from the group consisting of: SEQ ID NOs: 121, and 127-133;
(l) a second framework (FR2) which has a sequence of SEQ ID NO: 123;
(m) a third framework (FR3) which has a sequence selected from the group consisting of: SEQ ID NOs: 124-126; and
(n) a fourth framework (FR4) has a sequence of SEQ ID NOs: 122.

14. An anti-TF antibody comprising:
(a) three CDRs for a light chain wherein the CDRs are encoded by:

```
                                    (SEQ ID NO: 11)
(i)    CTGGCAAGTCAGACCATTGAT;

(SEQ ID NO: 12)
(ii)   GCTGCCACCAACTTGGCAGAT; or (SEQ ID NO: 13)
(iii)  CAACAAGTTTACAGTTCT CCATTCACGT; and
```

(b) three CDRs for a heavy chain wherein the CDRs are encoded by:

```
                                    (SEQ ID NO: 14)
(i)         ACTGACTACAACGTGTAC;

(SEQ ID NO: 15)
(ii)        TATATTGATCCTTACAATGGTATTACTATC
            TACGACCAGAACTTCAAGGGC; or (SEQ ID NO: 16)
(iii)       GATGTGACTACGGCCCTTGACTTC; and
```

(c) a framework region for the light chain comprising:
  (i) a first framework (FR1) which comprises a sequence of SEQ ID NO:109;
  (ii) a second framework (FR2) which comprises a sequence of: SEQ ID NO: 108 or SEQ ID NO: 115;
  (iii) a third framework (FR3) which comprises a sequence selected from the group consisting of: SEQ ID NOs: 111-114; and
  (iv) a fourth framework (FR4) which comprises a sequence of SEQ ID NO: 107 or SEQ ID NO: 110; and (d) a framework region for the heavy chain comprising:
  (i) a first framework (FR1) which has a sequence selected from the group consisting of: SEQ ID NOs: 121, and 127-133;
  (ii) a second framework (FR2) which has a sequence of SEQ ID NO: 123;
  (iii) a third framework (FR3) which has a sequence selected from the group consisting of: SEQ ID NOs: 124-126; and
  (iv) a fourth framework (FR4) has a sequence of SEQ ID NOs: 122.

* * * * *

UNITED STATES PATENT AND TRADEMARK OFFICE
CERTIFICATE OF CORRECTION

PATENT NO. : 8,007,795 B2  Page 1 of 1
APPLICATION NO. : 12/404256
DATED : August 30, 2011
INVENTOR(S) : Jin-an Jiao et al.

It is certified that error appears in the above-identified patent and that said Letters Patent is hereby corrected as shown below:

In Claim 1:

Column 107, lines 49-50; replace "(g) a fourth framework (FR4) comprising a sequence having at least 95% identity to a sequence selected from the group consisting of: SEQ ID SEQ ID NO: 110" with -- (g) a fourth framework (FR4) comprising a sequence having at least 95% identity to SEQ ID NO: 110 --.

Signed and Sealed this
Sixth Day of November, 2012

David J. Kappos
*Director of the United States Patent and Trademark Office*

SEQUENCE LISTING

<160> NUMBER OF SEQ ID NOS: 134

<210> SEQ ID NO 1
<211> LENGTH: 321
<212> TYPE: DNA
<213> ORGANISM: Mus musculus
<220> FEATURE:
<221> NAME/KEY: CDS
<222> LOCATION: (1)..(321)

<400> SEQUENCE: 1

```
gac att cag atg acc cag tct cct gcc tcc cag tct gca tct ctg gga      48
Asp Ile Gln Met Thr Gln Ser Pro Ala Ser Gln Ser Ala Ser Leu Gly
  1               5                  10                  15 gaa agt gtc acc atc aca tgc ctg gca agt cag acc att gat aca tgg      96
Glu Ser Val Thr Ile Thr Cys Leu Ala Ser Gln Thr Ile Asp Thr Trp
             20                  25                  30 tta gca tgg tat cag cag aaa cca ggg aaa tct cct cag ctc ctg att     144
Leu Ala Trp Tyr Gln Gln Lys Pro Gly Lys Ser Pro Gln Leu Leu Ile
         35                  40                  45 tat gct gcc acc aac ttg gca gat ggg gtc cca tca agg ttc agt ggc     192
Tyr Ala Ala Thr Asn Leu Ala Asp Gly Val Pro Ser Arg Phe Ser Gly
     50                  55                  60 agt gga tct ggc aca aaa ttt tct ttc aag atc agc agc cta cag gct     240
Ser Gly Ser Gly Thr Lys Phe Ser Phe Lys Ile Ser Ser Leu Gln Ala
 65                  70                  75                  80 gaa gat ttt gta aat tat tac tgt caa caa gtt tac agt tct cca ttc     288
Glu Asp Phe Val Asn Tyr Tyr Cys Gln Gln Val Tyr Ser Ser Pro Phe
                 85                  90                  95 acg ttc ggt gct ggg acc aag ctg gag ctg aaa                          321
Thr Phe Gly Ala Gly Thr Lys Leu Glu Leu Lys
            100                 105
```

<210> SEQ ID NO 2
<211> LENGTH: 107
<212> TYPE: PRT
<213> ORGANISM: Mus musculus

<400> SEQUENCE: 2

Asp Ile Gln Met Thr Gln Ser Pro Ala Ser Gln Ser Ala Ser Leu Gly
  1               5                  10                  15

Glu Ser Val Thr Ile Thr Cys Leu Ala Ser Gln Thr Ile Asp Thr Trp
             20                  25                  30

Leu Ala Trp Tyr Gln Gln Lys Pro Gly Lys Ser Pro Gln Leu Leu Ile
         35                  40                  45

Tyr Ala Ala Thr Asn Leu Ala Asp Gly Val Pro Ser Arg Phe Ser Gly
     50                  55                  60

Ser Gly Ser Gly Thr Lys Phe Ser Phe Lys Ile Ser Ser Leu Gln Ala
 65                  70                  75                  80

Glu Asp Phe Val Asn Tyr Tyr Cys Gln Gln Val Tyr Ser Ser Pro Phe
                 85                  90                  95

Thr Phe Gly Ala Gly Thr Lys Leu Glu Leu Lys
            100                 105

<210> SEQ ID NO 3
<211> LENGTH: 351
<212> TYPE: DNA
<213> ORGANISM: Mus musculus
<220> FEATURE:
<221> NAME/KEY: CDS
<222> LOCATION: (1)..(351)

```
<400> SEQUENCE: 3 gag atc cag ctg cag cag tct gga cct gag ctg gtg aag cct ggg gct      48
Glu Ile Gln Leu Gln Gln Ser Gly Pro Glu Leu Val Lys Pro Gly Ala
  1               5                  10                  15 tca gtg cag gta tcc tgc aag act tct ggt tac tca ttc act gac tac      96
Ser Val Gln Val Ser Cys Lys Thr Ser Gly Tyr Ser Phe Thr Asp Tyr
             20                  25                  30 aac gtg tac tgg gtg agg cag agc cat gga aag agc ctt gag tgg att     144
Asn Val Tyr Trp Val Arg Gln Ser His Gly Lys Ser Leu Glu Trp Ile
         35                  40                  45 gga tat att gat cct tac aat ggt att act atc tac gac cag aac ttc     192
Gly Tyr Ile Asp Pro Tyr Asn Gly Ile Thr Ile Tyr Asp Gln Asn Phe
     50                  55                  60 aag ggc aag gcc aca ttg act gtt gac aag tct tcc acc aca gcc ttc     240
Lys Gly Lys Ala Thr Leu Thr Val Asp Lys Ser Ser Thr Thr Ala Phe
 65                  70                  75                  80 atg cat ctc aac agc ctg aca tct gac gac tct gca gtt tat ttc tgt     288
Met His Leu Asn Ser Leu Thr Ser Asp Asp Ser Ala Val Tyr Phe Cys
                 85                  90                  95 gca aga gat gtg act acg gcc ctt gac ttc tgg ggc caa ggc acc act     336
Ala Arg Asp Val Thr Thr Ala Leu Asp Phe Trp Gly Gln Gly Thr Thr
            100                 105                 110 ctc aca gtc tcc tca                                                  351
Leu Thr Val Ser Ser
        115

<210> SEQ ID NO 4
<211> LENGTH: 117
<212> TYPE: PRT
<213> ORGANISM: Mus musculus

<400> SEQUENCE: 4

Glu Ile Gln Leu Gln Gln Ser Gly Pro Glu Leu Val Lys Pro Gly Ala
  1               5                  10                  15

Ser Val Gln Val Ser Cys Lys Thr Ser Gly Tyr Ser Phe Thr Asp Tyr
             20                  25                  30

Asn Val Tyr Trp Val Arg Gln Ser His Gly Lys Ser Leu Glu Trp Ile
         35                  40                  45

Gly Tyr Ile Asp Pro Tyr Asn Gly Ile Thr Ile Tyr Asp Gln Asn Phe
     50                  55                  60

Lys Gly Lys Ala Thr Leu Thr Val Asp Lys Ser Ser Thr Thr Ala Phe
 65                  70                  75                  80

Met His Leu Asn Ser Leu Thr Ser Asp Asp Ser Ala Val Tyr Phe Cys
                 85                  90                  95

Ala Arg Asp Val Thr Thr Ala Leu Asp Phe Trp Gly Gln Gly Thr Thr
            100                 105                 110

Leu Thr Val Ser Ser
        115

<210> SEQ ID NO 5
<211> LENGTH: 7
<212> TYPE: PRT
<213> ORGANISM: Mus musculus

<400> SEQUENCE: 5

Leu Ala Ser Gln Thr Ile Asp
  1               5

<210> SEQ ID NO 6
```

```
<211> LENGTH: 7
<212> TYPE: PRT
<213> ORGANISM: Mus musculus

<400> SEQUENCE: 6

Ala Ala Thr Asn Leu Ala Asp
1               5

<210> SEQ ID NO 7
<211> LENGTH: 9
<212> TYPE: PRT
<213> ORGANISM: Mus musculus

<400> SEQUENCE: 7

Gln Gln Val Tyr Ser Ser Pro Phe Thr
1               5

<210> SEQ ID NO 8
<211> LENGTH: 6
<212> TYPE: PRT
<213> ORGANISM: Mus musculus

<400> SEQUENCE: 8

Thr Asp Tyr Asn Val Tyr
1               5

<210> SEQ ID NO 9
<211> LENGTH: 17
<212> TYPE: PRT
<213> ORGANISM: Mus musculus

<400> SEQUENCE: 9

Tyr Ile Asp Pro Tyr Asn Gly Ile Thr Ile Tyr Asp Gln Asn Phe Lys
1               5                   10                  15

Gly

<210> SEQ ID NO 10
<211> LENGTH: 8
<212> TYPE: PRT
<213> ORGANISM: Mus musculus

<400> SEQUENCE: 10

Asp Val Thr Thr Ala Leu Asp Phe
1               5

<210> SEQ ID NO 11
<211> LENGTH: 21
<212> TYPE: DNA
<213> ORGANISM: Mus musculus

<400> SEQUENCE: 11
ctggcaagtc agaccattga t                                             21

<210> SEQ ID NO 12
<211> LENGTH: 21
<212> TYPE: DNA
<213> ORGANISM: Mus musculus

<400> SEQUENCE: 12
gctgccacca acttggcaga t                                             21

<210> SEQ ID NO 13
<211> LENGTH: 28
<212> TYPE: DNA
<213> ORGANISM: Mus musculus
```

```
<400> SEQUENCE: 13
caacaagttt acagttctcc attcacgt                                              28

<210> SEQ ID NO 14
<211> LENGTH: 18
<212> TYPE: DNA
<213> ORGANISM: Mus musculus

<400> SEQUENCE: 14
actgactaca acgtgtac                                                         18

<210> SEQ ID NO 15
<211> LENGTH: 51
<212> TYPE: DNA
<213> ORGANISM: Mus musculus

<400> SEQUENCE: 15
tatattgatc cttacaatgg tattactatc tacgaccaga acttcaaggg c                    51

<210> SEQ ID NO 16
<211> LENGTH: 24
<212> TYPE: DNA
<213> ORGANISM: Mus musculus

<400> SEQUENCE: 16
gatgtgacta cggcccttga cttc                                                  24

<210> SEQ ID NO 17
<211> LENGTH: 23
<212> TYPE: DNA
<213> ORGANISM: Artificial Sequence
<220> FEATURE:
<223> OTHER INFORMATION: PCR Primer

<400> SEQUENCE: 17
gcacctccag atgttaactg ctc                                                   23

<210> SEQ ID NO 18
<211> LENGTH: 20
<212> TYPE: DNA
<213> ORGANISM: Artificial Sequence
<220> FEATURE:
<223> OTHER INFORMATION: PCR Primer

<400> SEQUENCE: 18
gaartavccc ttgaccaggc                                                       20

<210> SEQ ID NO 19
<211> LENGTH: 35
<212> TYPE: DNA
<213> ORGANISM: Artificial Sequence
<220> FEATURE:
<223> OTHER INFORMATION: PCR Primer

<400> SEQUENCE: 19
ggaggcggcg gttctgacat tgtgmtgwcm cartc                                      35

<210> SEQ ID NO 20
<211> LENGTH: 45
<212> TYPE: DNA
<213> ORGANISM: Artificial Sequence
<220> FEATURE:
<223> OTHER INFORMATION: PCR Primer

<400> SEQUENCE: 20
```

```
atttcaggcc cagccggcca tggccgargt ycarctkcar caryc                45
```

<210> SEQ ID NO 21
<211> LENGTH: 33
<212> TYPE: DNA
<213> ORGANISM: Artificial Sequence
<220> FEATURE:
<223> OTHER INFORMATION: PCR Primer

<400> SEQUENCE: 21

```
cccgggccac catgkccccw rctcagytyc tkg                             33
```

<210> SEQ ID NO 22
<211> LENGTH: 35
<212> TYPE: DNA
<213> ORGANISM: Artificial Sequence
<220> FEATURE:
<223> OTHER INFORMATION: PCR Primer

<400> SEQUENCE: 22

```
cccgggccac catggratgs agctgkgtma tsctc                           35
```

<210> SEQ ID NO 23
<211> LENGTH: 52
<212> TYPE: DNA
<213> ORGANISM: Artificial Sequence
<220> FEATURE:
<223> OTHER INFORMATION: PCR Primer

<400> SEQUENCE: 23

```
atatactcgc gacagctaca ggtgtccact ccgagatcca gctgcagcag tc        52
```

<210> SEQ ID NO 24
<211> LENGTH: 31
<212> TYPE: DNA
<213> ORGANISM: Artificial Sequence
<220> FEATURE:
<223> OTHER INFORMATION: PCR Primer

<400> SEQUENCE: 24

```
gacctgaatt ctaaggagac tgtgagagtg g                               31
```

<210> SEQ ID NO 25
<211> LENGTH: 29
<212> TYPE: DNA
<213> ORGANISM: Artificial Sequence
<220> FEATURE:
<223> OTHER INFORMATION: PCR Primer

<400> SEQUENCE: 25

```
ttaattgata tccagatgac ccagtctcc                                  29
```

<210> SEQ ID NO 26
<211> LENGTH: 45
<212> TYPE: DNA
<213> ORGANISM: Artificial Sequence
<220> FEATURE:
<223> OTHER INFORMATION: PCR Primer

<400> SEQUENCE: 26

```
taatcgttcg aaaagtgtac ttacgtttca gctccagctt ggtcc                45
```

<210> SEQ ID NO 27
<211> LENGTH: 38
<212> TYPE: PRT
<213> ORGANISM: Homo sapiens -continued

<400> SEQUENCE: 27

Asp Ile Gln Met Thr Gln Ser Pro Ala Ser Leu Ser Ala Ser Val Gly
1               5                   10                  15
Asp Arg Val Thr Ile Thr Cys Trp Tyr Leu Gln Lys Pro Gly Lys Ser
            20                  25                  30
Pro Gln Leu Leu Ile Tyr
        35

<210> SEQ ID NO 28
<211> LENGTH: 42
<212> TYPE: PRT
<213> ORGANISM: Homo sapiens

<400> SEQUENCE: 28

Gly Val Pro Ser Arg Phe Ser Gly Ser Gly Ser Gly Thr Asp Phe Ser
1               5                   10                  15
Phe Thr Ile Ser Ser Leu Gln Pro Glu Asp Phe Ala Thr Tyr Tyr Cys
            20                  25                  30
Phe Gly Gln Gly Thr Lys Leu Glu Ile Lys
        35                  40

<210> SEQ ID NO 29
<211> LENGTH: 44
<212> TYPE: PRT
<213> ORGANISM: Homo sapiens

<400> SEQUENCE: 29

Gln Ile Gln Leu Val Gln Ser Gly Gly Glu Val Lys Lys Pro Gly Ala
1               5                   10                  15
Ser Val Arg Val Ser Cys Lys Ala Ser Gly Tyr Ser Phe Thr Trp Val
            20                  25                  30
Arg Gln Ser Pro Gly Lys Gly Leu Glu Trp Ile Gly
        35                  40

<210> SEQ ID NO 30
<211> LENGTH: 43
<212> TYPE: PRT
<213> ORGANISM: Homo sapiens

<400> SEQUENCE: 30

Lys Ala Thr Leu Thr Val Asp Lys Ser Thr Ser Thr Ala Tyr Met Glu
1               5                   10                  15
Leu Ser Ser Leu Arg Ser Glu Asp Thr Ala Val Tyr Phe Cys Ala Arg
            20                  25                  30
Trp Gly Gln Gly Thr Thr Val Thr Val Ser Ser
        35                  40

<210> SEQ ID NO 31
<211> LENGTH: 37
<212> TYPE: DNA
<213> ORGANISM: Artificial Sequence
<220> FEATURE:
<223> OTHER INFORMATION: PCR Primer

<400> SEQUENCE: 31
tttcgtacgt cttgtcccag atccagctgc agcagtc                              37

<210> SEQ ID NO 32
<211> LENGTH: 43
<212> TYPE: DNA
<213> ORGANISM: Artificial Sequence

```
<220> FEATURE:
<223> OTHER INFORMATION: PCR Primer

<400> SEQUENCE: 32
agcgaattct gaggagactg tgacagtggt gccttggccc cag                        43

<210> SEQ ID NO 33
<211> LENGTH: 38
<212> TYPE: DNA
<213> ORGANISM: Artificial Sequence
<220> FEATURE:
<223> OTHER INFORMATION: PCR Primer

<400> SEQUENCE: 33
gtgaggcaga gccctggaaa gggccttgag tggattgg                              38

<210> SEQ ID NO 34
<211> LENGTH: 38
<212> TYPE: DNA
<213> ORGANISM: Artificial Sequence
<220> FEATURE:
<223> OTHER INFORMATION: PCR Primer

<400> SEQUENCE: 34
ccaatccact caaggccctt tccagggctc tgcctcac                              38

<210> SEQ ID NO 35
<211> LENGTH: 47
<212> TYPE: DNA
<213> ORGANISM: Artificial Sequence
<220> FEATURE:
<223> OTHER INFORMATION: PCR Primer

<400> SEQUENCE: 35
gcatctcaac agcctgagat ctgaagacac tgcagtttat ttctgtg                    47

<210> SEQ ID NO 36
<211> LENGTH: 43
<212> TYPE: DNA
<213> ORGANISM: Artificial Sequence
<220> FEATURE:
<223> OTHER INFORMATION: PCR Primer

<400> SEQUENCE: 36
ctgcagtgtc ttcagatctc aggctgttga gatgcatgaa ggc                        43

<210> SEQ ID NO 37
<211> LENGTH: 43
<212> TYPE: DNA
<213> ORGANISM: Artificial Sequence
<220> FEATURE:
<223> OTHER INFORMATION: PCR Primer

<400> SEQUENCE: 37
gtcttcagat ctcaggctgc tgagctccat gaaggctgtg gtg                        43

<210> SEQ ID NO 38
<211> LENGTH: 25
<212> TYPE: DNA
<213> ORGANISM: Artificial Sequence
<220> FEATURE:
<223> OTHER INFORMATION: PCR Primer

<400> SEQUENCE: 38
tacgactcac tatagggcga attgg                                            25
```

```
<210> SEQ ID NO 39
<211> LENGTH: 43
<212> TYPE: DNA
<213> ORGANISM: Artificial Sequence
<220> FEATURE:
<223> OTHER INFORMATION: PCR Primer

<400> SEQUENCE: 39
ctgttgacaa gtctaccagc acagcctaca tggagctcag cag          43

<210> SEQ ID NO 40
<211> LENGTH: 43
<212> TYPE: DNA
<213> ORGANISM: Artificial Sequence
<220> FEATURE:
<223> OTHER INFORMATION: PCR Primer

<400> SEQUENCE: 40
ctgctgagct ccatgtaggc tgtgctggta gacttgtcaa cag          43

<210> SEQ ID NO 41
<211> LENGTH: 47
<212> TYPE: DNA
<213> ORGANISM: Artificial Sequence
<220> FEATURE:
<223> OTHER INFORMATION: PCR Primer

<400> SEQUENCE: 41
gcactgaagc cccaggcttc accagctcac ctccagactg ctgcagc      47

<210> SEQ ID NO 42
<211> LENGTH: 49
<212> TYPE: DNA
<213> ORGANISM: Artificial Sequence
<220> FEATURE:
<223> OTHER INFORMATION: PCR Primer

<400> SEQUENCE: 42
ctggggcttc agtgcgggta tcctgcaagg cttctggtta ctcattcac    49

<210> SEQ ID NO 43
<211> LENGTH: 46
<212> TYPE: DNA
<213> ORGANISM: Artificial Sequence
<220> FEATURE:
<223> OTHER INFORMATION: PCR Primer

<400> SEQUENCE: 43
tcgtacgtct tgtcccagat ccagctggtg cagtctggag gtgagc       46

<210> SEQ ID NO 44
<211> LENGTH: 44
<212> TYPE: DNA
<213> ORGANISM: Artificial Sequence
<220> FEATURE:
<223> OTHER INFORMATION: PCR Primer

<400> SEQUENCE: 44
gcactgaagc cccaggcttc ttcacctcac ctccagactg cacc         44

<210> SEQ ID NO 45
<211> LENGTH: 32
<212> TYPE: DNA
<213> ORGANISM: Artificial Sequence
<220> FEATURE:
<223> OTHER INFORMATION: PCR Primer

<400> SEQUENCE: 45
```

```
gcagtctgga cctgagctga agaagcctgg gg                                    32

<210> SEQ ID NO 46
<211> LENGTH: 32
<212> TYPE: DNA
<213> ORGANISM: Artificial Sequence
<220> FEATURE:
<223> OTHER INFORMATION: PCR Primer

<400> SEQUENCE: 46
ccccaggctt cttcagctca ggtccagact gc                                    32

<210> SEQ ID NO 47
<211> LENGTH: 33
<212> TYPE: DNA
<213> ORGANISM: Artificial Sequence
<220> FEATURE:
<223> OTHER INFORMATION: PCR Primer

<400> SEQUENCE: 47
gctggtgcag tctggacctg aggtgaagaa gcc                                   33

<210> SEQ ID NO 48
<211> LENGTH: 33
<212> TYPE: DNA
<213> ORGANISM: Artificial Sequence
<220> FEATURE:
<223> OTHER INFORMATION: PCR Primer

<400> SEQUENCE: 48
ggcttcttca cctcaggtcc agactgcacc agc                                   33

<210> SEQ ID NO 49
<211> LENGTH: 36
<212> TYPE: DNA
<213> ORGANISM: Artificial Sequence
<220> FEATURE:
<223> OTHER INFORMATION: PCR Primer

<400> SEQUENCE: 49
gcagtctgga cctgagctgg tgaagcctgg ggcttc                                36

<210> SEQ ID NO 50
<211> LENGTH: 36
<212> TYPE: DNA
<213> ORGANISM: Artificial Sequence
<220> FEATURE:
<223> OTHER INFORMATION: PCR Primer

<400> SEQUENCE: 50
gaagccccag gcttcaccag ctcaggtcca gactgc                                36

<210> SEQ ID NO 51
<211> LENGTH: 30
<212> TYPE: DNA
<213> ORGANISM: Artificial Sequence
<220> FEATURE:
<223> OTHER INFORMATION: PCR Primer

<400> SEQUENCE: 51
cagtctggac ctgaggtggt gaagcctggg                                       30

<210> SEQ ID NO 52
<211> LENGTH: 30
<212> TYPE: DNA
<213> ORGANISM: Artificial Sequence
```

```
<220> FEATURE:
<223> OTHER INFORMATION: PCR Primer

<400> SEQUENCE: 52
cccaggcttc accacctcag gtccagactg                                          30

<210> SEQ ID NO 53
<211> LENGTH: 42
<212> TYPE: DNA
<213> ORGANISM: Artificial Sequence
<220> FEATURE:
<223> OTHER INFORMATION: PCR Primer

<400> SEQUENCE: 53
ttcgaaaagt gtacttacgt ttgatctcca gcttggtccc ag                            42

<210> SEQ ID NO 54
<211> LENGTH: 29
<212> TYPE: DNA
<213> ORGANISM: Artificial Sequence
<220> FEATURE:
<223> OTHER INFORMATION: PCR Primer

<400> SEQUENCE: 54
accggtgata tccagatgac ccagtctcc                                           29

<210> SEQ ID NO 55
<211> LENGTH: 29
<212> TYPE: DNA
<213> ORGANISM: Artificial Sequence
<220> FEATURE:
<223> OTHER INFORMATION: PCR Primer

<400> SEQUENCE: 55
ggttagcatg gtatctgcag aaaccaggg                                           29

<210> SEQ ID NO 56
<211> LENGTH: 29
<212> TYPE: DNA
<213> ORGANISM: Artificial Sequence
<220> FEATURE:
<223> OTHER INFORMATION: PCR Primer

<400> SEQUENCE: 56
ccctggtttc tgcagatacc atgctaacc                                           29

<210> SEQ ID NO 57
<211> LENGTH: 25
<212> TYPE: DNA
<213> ORGANISM: Artificial Sequence
<220> FEATURE:
<223> OTHER INFORMATION: PCR Primer

<400> SEQUENCE: 57
tacgactcac tatagggcga attgg                                               25

<210> SEQ ID NO 58
<211> LENGTH: 31
<212> TYPE: DNA
<213> ORGANISM: Artificial Sequence
<220> FEATURE:
<223> OTHER INFORMATION: PCR Primer

<400> SEQUENCE: 58
ccacagatgc agacagggag gcaggagact g                                        31
```

<210> SEQ ID NO 59
<211> LENGTH: 51
<212> TYPE: DNA
<213> ORGANISM: Artificial Sequence
<220> FEATURE:
<223> OTHER INFORMATION: PCR Primer

<400> SEQUENCE: 59
ttcgaaaagt gtacttacgt ttgatctcca gcttggtacc agcaccgaac g         51

<210> SEQ ID NO 60
<211> LENGTH: 40
<212> TYPE: DNA
<213> ORGANISM: Artificial Sequence
<220> FEATURE:
<223> OTHER INFORMATION: PCR Primer

<400> SEQUENCE: 60
cctgtctgca tctgtgggag atagggtcac catcacatgc                      40

<210> SEQ ID NO 61
<211> LENGTH: 36
<212> TYPE: DNA
<213> ORGANISM: Artificial Sequence
<220> FEATURE:
<223> OTHER INFORMATION: PCR Primer

<400> SEQUENCE: 61
gatctccagc ttggtaccct gaccgaacgt gaatgg                          36

<210> SEQ ID NO 62
<211> LENGTH: 40
<212> TYPE: DNA
<213> ORGANISM: Artificial Sequence
<220> FEATURE:
<223> OTHER INFORMATION: PCR Primer

<400> SEQUENCE: 62
gtaggctgct gatcgtgaaa gaaaagtctg tgccagatcc                      40

<210> SEQ ID NO 63
<211> LENGTH: 47
<212> TYPE: DNA
<213> ORGANISM: Artificial Sequence
<220> FEATURE:
<223> OTHER INFORMATION: PCR Primer

<400> SEQUENCE: 63
cacgatcagc agcctacagc ctgaagattt tgtaaattat tactgtc              47

<210> SEQ ID NO 64
<211> LENGTH: 45
<212> TYPE: DNA
<213> ORGANISM: Artificial Sequence
<220> FEATURE:
<223> OTHER INFORMATION: PCR Primer

<400> SEQUENCE: 64
gcagcctaca gcctgaagat tttgcaactt attactgtca acaag                45

<210> SEQ ID NO 65
<211> LENGTH: 45
<212> TYPE: DNA
<213> ORGANISM: Artificial Sequence
<220> FEATURE:
<223> OTHER INFORMATION: PCR Primer

<400> SEQUENCE: 65

-continued

```
cttgttgaca gtaataagtt gcaaaatctt caggctgtag gctgc                      45

<210> SEQ ID NO 66
<211> LENGTH: 44
<212> TYPE: DNA
<213> ORGANISM: Artificial Sequence
<220> FEATURE:
<223> OTHER INFORMATION: PCR Primer

<400> SEQUENCE: 66
cagcagccta cagcctgaag attttgcaaa ttattactgt caac                       44

<210> SEQ ID NO 67
<211> LENGTH: 44
<212> TYPE: DNA
<213> ORGANISM: Artificial Sequence
<220> FEATURE:
<223> OTHER INFORMATION: PCR Primer

<400> SEQUENCE: 67
gttgacagta ataatttgca aaatcttcag gctgtaggct gctg                       44

<210> SEQ ID NO 68
<211> LENGTH: 40
<212> TYPE: DNA
<213> ORGANISM: Artificial Sequence
<220> FEATURE:
<223> OTHER INFORMATION: PCR Primer

<400> SEQUENCE: 68
cagtggatct ggcacaaagt tttctttcac gatcagcagc                            40

<210> SEQ ID NO 69
<211> LENGTH: 40
<212> TYPE: DNA
<213> ORGANISM: Artificial Sequence
<220> FEATURE:
<223> OTHER INFORMATION: PCR Primer

<400> SEQUENCE: 69
gctgctgatc gtgaaagaaa actttgtgcc agatccactg                            40

<210> SEQ ID NO 70
<211> LENGTH: 33
<212> TYPE: DNA
<213> ORGANISM: Artificial Sequence
<220> FEATURE:
<223> OTHER INFORMATION: PCR Primer

<400> SEQUENCE: 70
ctgcagaaac cagggcaatc tcctcagctc ctg                                   33

<210> SEQ ID NO 71
<211> LENGTH: 33
<212> TYPE: DNA
<213> ORGANISM: Artificial Sequence
<220> FEATURE:
<223> OTHER INFORMATION: PCR Primer

<400> SEQUENCE: 71
caggagctga ggagattgcc ctggtttctg cag                                   33

<210> SEQ ID NO 72
<211> LENGTH: 80
<212> TYPE: PRT
<213> ORGANISM: Artificial Sequence
```

<220> FEATURE:
<223> OTHER INFORMATION: Synthetic FR1, FR2, FR3 and FR4 of CH36-LC

<400> SEQUENCE: 72

Asp Ile Gln Met Thr Gln Ser Pro Ala Ser Gln Ser Ala Ser Leu Gly
1               5                   10                  15

Glu Ser Val Thr Ile Thr Cys Trp Tyr Gln Gln Lys Pro Gly Lys Ser
            20                  25                  30

Pro Gln Leu Leu Ile Tyr Gly Val Pro Ser Arg Phe Ser Gly Ser Gly
        35                  40                  45

Ser Gly Thr Lys Phe Ser Phe Lys Ile Ser Ser Leu Gln Ala Glu Asp
    50                  55                  60

Phe Val Asn Tyr Tyr Cys Phe Gly Ala Gly Thr Lys Leu Glu Leu Lys
65                  70                  75                  80

<210> SEQ ID NO 73
<211> LENGTH: 80
<212> TYPE: PRT
<213> ORGANISM: Artificial Sequence
<220> FEATURE:
<223> OTHER INFORMATION: Synthetic humanized FR1, FR2, FR3 and FR4 of
      LC-03

<400> SEQUENCE: 73

Asp Ile Gln Met Thr Gln Ser Pro Ala Ser Gln Ser Ala Ser Leu Gly
1               5                   10                  15

Glu Ser Val Thr Ile Thr Cys Trp Tyr Gln Gln Lys Pro Gly Lys Ser
            20                  25                  30

Pro Gln Leu Leu Ile Tyr Gly Val Pro Ser Arg Phe Ser Gly Ser Gly
        35                  40                  45

Ser Gly Thr Lys Phe Ser Phe Lys Ile Ser Ser Leu Gln Ala Glu Asp
    50                  55                  60

Phe Val Asn Tyr Tyr Cys Phe Gly Ala Gly Thr Lys Leu Glu Ile Lys
65                  70                  75                  80

<210> SEQ ID NO 74
<211> LENGTH: 80
<212> TYPE: PRT
<213> ORGANISM: Artificial Sequence
<220> FEATURE:
<223> OTHER INFORMATION: Synthetic humanized FR1, FR2, FR3 and FR4 of
      LC-04

<400> SEQUENCE: 74

Asp Ile Gln Met Thr Gln Ser Pro Ala Ser Gln Ser Ala Ser Leu Gly
1               5                   10                  15

Glu Ser Val Thr Ile Thr Cys Trp Tyr Leu Gln Lys Pro Gly Lys Ser
            20                  25                  30

Pro Gln Leu Leu Ile Tyr Gly Val Pro Ser Arg Phe Ser Gly Ser Gly
        35                  40                  45

Ser Gly Thr Lys Phe Ser Phe Lys Ile Ser Ser Leu Gln Ala Glu Asp
    50                  55                  60

Phe Val Asn Tyr Tyr Cys Phe Gly Ala Gly Thr Lys Leu Glu Ile Lys
65                  70                  75                  80

<210> SEQ ID NO 75
<211> LENGTH: 80
<212> TYPE: PRT
<213> ORGANISM: Artificial Sequence
<220> FEATURE:
<223> OTHER INFORMATION: Synthetic humanized FR1, FR2, FR3 and FR4 of
      LC-05

```
<400> SEQUENCE: 75

Asp Ile Gln Met Thr Gln Ser Pro Ala Ser Leu Ser Ala Ser Val Gly
1               5                   10                  15

Asp Arg Val Thr Ile Thr Cys Trp Tyr Leu Gln Lys Pro Gly Lys Ser
            20                  25                  30

Pro Gln Leu Leu Ile Tyr Gly Val Pro Ser Arg Phe Ser Gly Ser Gly
        35                  40                  45

Ser Gly Thr Lys Phe Ser Phe Lys Ile Ser Ser Leu Gln Ala Glu Asp
    50                  55                  60

Phe Val Asn Tyr Tyr Cys Phe Gly Gln Gly Thr Lys Leu Glu Ile Lys
65                  70                  75                  80

<210> SEQ ID NO 76
<211> LENGTH: 80
<212> TYPE: PRT
<213> ORGANISM: Artificial Sequence
<220> FEATURE:
<223> OTHER INFORMATION: Synthetic humanized FR1, FR2, FR3 and FR4 of
      LC-06

<400> SEQUENCE: 76

Asp Ile Gln Met Thr Gln Ser Pro Ala Ser Gln Ser Ala Ser Leu Gly
1               5                   10                  15

Glu Ser Val Thr Ile Thr Cys Trp Tyr Leu Gln Lys Pro Gly Lys Ser
            20                  25                  30

Pro Gln Leu Leu Ile Tyr Gly Val Pro Ser Arg Phe Ser Gly Ser Gly
        35                  40                  45

Ser Gly Thr Lys Phe Ser Phe Lys Ile Ser Ser Leu Gln Ala Glu Asp
    50                  55                  60

Phe Val Asn Tyr Tyr Cys Phe Gly Gln Gly Thr Lys Leu Glu Ile Lys
65                  70                  75                  80

<210> SEQ ID NO 77
<211> LENGTH: 80
<212> TYPE: PRT
<213> ORGANISM: Artificial Sequence
<220> FEATURE:
<223> OTHER INFORMATION: Synthetic humanized FR1, FR2, FR3 and FR4 of
      LC-07

<400> SEQUENCE: 77

Asp Ile Gln Met Thr Gln Ser Pro Ala Ser Gln Ser Ala Ser Leu Gly
1               5                   10                  15

Glu Ser Val Thr Ile Thr Cys Trp Tyr Leu Gln Lys Pro Gly Lys Ser
            20                  25                  30

Pro Gln Leu Leu Ile Tyr Gly Val Pro Ser Arg Phe Ser Gly Ser Gly
        35                  40                  45

Ser Gly Thr Asp Phe Ser Phe Thr Ile Ser Ser Leu Gln Pro Glu Asp
    50                  55                  60

Phe Val Asn Tyr Tyr Cys Phe Gly Gln Gly Thr Lys Leu Glu Ile Lys
65                  70                  75                  80

<210> SEQ ID NO 78
<211> LENGTH: 80
<212> TYPE: PRT
<213> ORGANISM: Artificial Sequence
<220> FEATURE:
<223> OTHER INFORMATION: Synthetic humanized FR1, FR2, FR3 and FR4 of
      LC-08

<400> SEQUENCE: 78
```

```
Asp Ile Gln Met Thr Gln Ser Pro Ala Ser Gln Ser Ala Ser Leu Gly
1               5                   10                  15

Glu Ser Val Thr Ile Thr Cys Trp Tyr Leu Gln Lys Pro Gly Lys Ser
            20                  25                  30

Pro Gln Leu Leu Ile Tyr Gly Val Pro Ser Arg Phe Ser Gly Ser Gly
            35                  40                  45

Ser Gly Thr Asp Phe Ser Phe Thr Ile Ser Ser Leu Gln Pro Glu Asp
50                  55                  60

Phe Ala Thr Tyr Tyr Cys Phe Gly Gln Gly Thr Lys Leu Glu Ile Lys
65                  70                  75                  80

<210> SEQ ID NO 79
<211> LENGTH: 80
<212> TYPE: PRT
<213> ORGANISM: Artificial Sequence
<220> FEATURE:
<223> OTHER INFORMATION: Synthetic humanized FR1, FR2, FR3 and FR4 of
      LC-09

<400> SEQUENCE: 79

Asp Ile Gln Met Thr Gln Ser Pro Ala Ser Leu Ser Ala Ser Val Gly
1               5                   10                  15

Asp Arg Val Thr Ile Thr Cys Trp Tyr Leu Gln Lys Pro Gly Lys Ser
            20                  25                  30

Pro Gln Leu Leu Ile Tyr Gly Val Pro Ser Arg Phe Ser Gly Ser Gly
            35                  40                  45

Ser Gly Thr Asp Phe Ser Phe Thr Ile Ser Ser Leu Gln Pro Glu Asp
50                  55                  60

Phe Ala Thr Tyr Tyr Cys Phe Gly Gln Gly Thr Lys Leu Glu Ile Lys
65                  70                  75                  80

<210> SEQ ID NO 80
<211> LENGTH: 80
<212> TYPE: PRT
<213> ORGANISM: Artificial Sequence
<220> FEATURE:
<223> OTHER INFORMATION: Synthetic humanized FR1, FR2, FR3 and FR4 of
      LC-10

<400> SEQUENCE: 80

Asp Ile Gln Met Thr Gln Ser Pro Ala Ser Leu Ser Ala Ser Val Gly
1               5                   10                  15

Asp Arg Val Thr Ile Thr Cys Trp Tyr Leu Gln Lys Pro Gly Lys Ser
            20                  25                  30

Pro Gln Leu Leu Ile Tyr Gly Val Pro Ser Arg Phe Ser Gly Ser Gly
            35                  40                  45

Ser Gly Thr Asp Phe Ser Phe Thr Ile Ser Ser Leu Gln Pro Glu Asp
50                  55                  60

Phe Ala Asn Tyr Tyr Cys Phe Gly Gln Gly Thr Lys Leu Glu Ile Lys
65                  70                  75                  80

<210> SEQ ID NO 81
<211> LENGTH: 80
<212> TYPE: PRT
<213> ORGANISM: Artificial Sequence
<220> FEATURE:
<223> OTHER INFORMATION: Synthetic humanized FR1, FR2, FR3 and FR4 of
      LC-11

<400> SEQUENCE: 81

Asp Ile Gln Met Thr Gln Ser Pro Ala Ser Leu Ser Ala Ser Val Gly
```

```
                 1               5                  10                 15
Asp Arg Val Thr Ile Thr Cys Trp Tyr Leu Gln Lys Pro Gly Lys Ser
                20                 25                 30

Pro Gln Leu Leu Ile Tyr Gly Val Pro Ser Arg Phe Ser Gly Ser Gly
            35                 40                 45

Ser Gly Thr Lys Phe Ser Phe Thr Ile Ser Ser Leu Gln Pro Glu Asp
        50                 55                 60

Phe Ala Asn Tyr Tyr Cys Phe Gly Gln Gly Thr Lys Leu Glu Ile Lys
65                 70                 75                 80

<210> SEQ ID NO 82
<211> LENGTH: 80
<212> TYPE: PRT
<213> ORGANISM: Artificial Sequence
<220> FEATURE:
<223> OTHER INFORMATION: Synthetic humanized FR1, FR2, FR3 and FR4 of
      LC-12

<400> SEQUENCE: 82

Asp Ile Gln Met Thr Gln Ser Pro Ala Ser Leu Ser Ala Ser Val Gly
1               5                  10                 15

Asp Arg Val Thr Ile Thr Cys Trp Tyr Leu Gln Lys Pro Gly Gln Ser
                20                 25                 30

Pro Gln Leu Leu Ile Tyr Gly Val Pro Ser Arg Phe Ser Gly Ser Gly
            35                 40                 45

Ser Gly Thr Lys Phe Ser Phe Thr Ile Ser Ser Leu Gln Pro Glu Asp
        50                 55                 60

Phe Ala Asn Tyr Tyr Cys Phe Gly Gln Gly Thr Lys Leu Glu Ile Lys
65                 70                 75                 80

<210> SEQ ID NO 83
<211> LENGTH: 87
<212> TYPE: PRT
<213> ORGANISM: Artificial Sequence
<220> FEATURE:
<223> OTHER INFORMATION: Synthetic FR1, FR2, FR3 and FR4 of CH36-HC

<400> SEQUENCE: 83

Glu Ile Gln Leu Gln Gln Ser Gly Pro Glu Leu Val Lys Pro Gly Ala
1               5                  10                 15

Ser Val Gln Val Ser Cys Lys Thr Ser Gly Tyr Ser Phe Thr Trp Val
                20                 25                 30

Arg Gln Ser His Gly Lys Ser Leu Glu Trp Ile Gly Lys Ala Thr Leu
            35                 40                 45

Thr Val Asp Lys Ser Ser Thr Thr Ala Phe Met His Leu Asn Ser Leu
        50                 55                 60

Thr Ser Asp Asp Ser Ala Val Tyr Phe Cys Ala Arg Trp Gly Gln Gly
65                 70                 75                 80

Thr Thr Leu Thr Val Ser Ser
                85

<210> SEQ ID NO 84
<211> LENGTH: 87
<212> TYPE: PRT
<213> ORGANISM: Artificial Sequence
<220> FEATURE:
<223> OTHER INFORMATION: Synthetic humanized FR1, FR2, FR3 and FR4 of
      HC-01

<400> SEQUENCE: 84

Gln Ile Gln Leu Gln Gln Ser Gly Pro Glu Leu Val Lys Pro Gly Ala
```

```
                1               5                  10                 15
Ser Val Gln Val Ser Cys Lys Thr Ser Gly Tyr Ser Phe Thr Trp Val
                20                 25                 30

Arg Gln Ser His Gly Lys Ser Leu Glu Trp Ile Gly Lys Ala Thr Leu
            35                 40                 45

Thr Val Asp Lys Ser Ser Thr Thr Ala Phe Met His Leu Asn Ser Leu
    50                 55                 60

Thr Ser Asp Asp Ser Ala Val Tyr Phe Cys Ala Arg Trp Gly Gln Gly
65                 70                 75                 80

Thr Thr Val Thr Val Ser Ser
                85

<210> SEQ ID NO 85
<211> LENGTH: 87
<212> TYPE: PRT
<213> ORGANISM: Artificial Sequence
<220> FEATURE:
<223> OTHER INFORMATION: Synthetic humanized FR1, FR2, FR3 and FR4 of
      HC-02

<400> SEQUENCE: 85

Gln Ile Gln Leu Gln Gln Ser Gly Pro Glu Leu Val Lys Pro Gly Ala
1               5                  10                 15

Ser Val Gln Val Ser Cys Lys Thr Ser Gly Tyr Ser Phe Thr Trp Val
                20                 25                 30

Arg Gln Ser Pro Gly Lys Gly Leu Glu Trp Ile Gly Lys Ala Thr Leu
            35                 40                 45

Thr Val Asp Lys Ser Ser Thr Thr Ala Phe Met His Leu Asn Ser Leu
    50                 55                 60

Thr Ser Asp Asp Ser Ala Val Tyr Phe Cys Ala Arg Trp Gly Gln Gly
65                 70                 75                 80

Thr Thr Val Thr Val Ser Ser
                85

<210> SEQ ID NO 86
<211> LENGTH: 87
<212> TYPE: PRT
<213> ORGANISM: Artificial Sequence
<220> FEATURE:
<223> OTHER INFORMATION: Synthetic humanized FR1, FR2, FR3 and FR4 of
      HC-03

<400> SEQUENCE: 86

Gln Ile Gln Leu Gln Gln Ser Gly Pro Glu Leu Val Lys Pro Gly Ala
1               5                  10                 15

Ser Val Gln Val Ser Cys Lys Thr Ser Gly Tyr Ser Phe Thr Trp Val
                20                 25                 30

Arg Gln Ser Pro Gly Lys Gly Leu Glu Trp Ile Gly Lys Ala Thr Leu
            35                 40                 45

Thr Val Asp Lys Ser Ser Thr Thr Ala Phe Met His Leu Asn Ser Leu
    50                 55                 60

Arg Ser Glu Asp Thr Ala Val Tyr Phe Cys Ala Arg Trp Gly Gln Gly
65                 70                 75                 80

Thr Thr Val Thr Val Ser Ser
                85

<210> SEQ ID NO 87
<211> LENGTH: 87
<212> TYPE: PRT
<213> ORGANISM: Artificial Sequence
```

```
<220> FEATURE:
<223> OTHER INFORMATION: Synthetic humanized FR1, FR2, FR3 and FR4 of
      HC-04

<400> SEQUENCE: 87

Gln Ile Gln Leu Gln Gln Ser Gly Pro Glu Leu Val Lys Pro Gly Ala
1               5                   10                  15

Ser Val Gln Val Ser Cys Lys Thr Ser Gly Tyr Ser Phe Thr Trp Val
            20                  25                  30

Arg Gln Ser Pro Gly Lys Gly Leu Glu Trp Ile Gly Lys Ala Thr Leu
        35                  40                  45

Thr Val Asp Lys Ser Ser Thr Thr Ala Phe Met Glu Leu Ser Ser Leu
    50                  55                  60

Arg Ser Glu Asp Thr Ala Val Tyr Phe Cys Ala Arg Trp Gly Gln Gly
65                  70                  75                  80

Thr Thr Val Thr Val Ser Ser
                85

<210> SEQ ID NO 88
<211> LENGTH: 87
<212> TYPE: PRT
<213> ORGANISM: Artificial Sequence
<220> FEATURE:
<223> OTHER INFORMATION: Synthetic humanized FR1, FR2, FR3 and FR4 of
      HC-05

<400> SEQUENCE: 88

Gln Ile Gln Leu Gln Gln Ser Gly Pro Glu Leu Val Lys Pro Gly Ala
1               5                   10                  15

Ser Val Gln Val Ser Cys Lys Thr Ser Gly Tyr Ser Phe Thr Trp Val
            20                  25                  30

Arg Gln Ser Pro Gly Lys Gly Leu Glu Trp Ile Gly Lys Ala Thr Leu
        35                  40                  45

Thr Val Asp Lys Ser Thr Ser Thr Ala Tyr Met Glu Leu Ser Ser Leu
    50                  55                  60

Arg Ser Glu Asp Thr Ala Val Tyr Phe Cys Ala Arg Trp Gly Gln Gly
65                  70                  75                  80

Thr Thr Val Thr Val Ser Ser
                85

<210> SEQ ID NO 89
<211> LENGTH: 87
<212> TYPE: PRT
<213> ORGANISM: Artificial Sequence
<220> FEATURE:
<223> OTHER INFORMATION: Synthetic humanized FR1, FR2, FR3 and FR4 of
      HC-06

<400> SEQUENCE: 89

Gln Met Gln Leu Gln Gln Ser Gly Gly Glu Leu Val Lys Pro Gly Ala
1               5                   10                  15

Ser Val Arg Val Ser Cys Lys Ala Ser Gly Tyr Ser Phe Thr Trp Val
            20                  25                  30

Arg Gln Ser Pro Gly Lys Gly Leu Glu Trp Ile Gly Lys Ala Thr Leu
        35                  40                  45

Thr Val Asp Lys Ser Thr Ser Thr Ala Tyr Met Glu Leu Ser Ser Leu
    50                  55                  60

Arg Ser Glu Asp Thr Ala Val Tyr Phe Cys Ala Arg Trp Gly Gln Gly
65                  70                  75                  80

Thr Thr Val Thr Val Ser Ser
```

<210> SEQ ID NO 90
<211> LENGTH: 87
<212> TYPE: PRT
<213> ORGANISM: Artificial Sequence
<220> FEATURE:
<223> OTHER INFORMATION: Synthetic humanized FR1, FR2, FR3 and FR4 of HC-07

<400> SEQUENCE: 90

Gln Ile Gln Leu Val Gln Ser Gly Gly Glu Leu Val Lys Pro Gly Ala
1               5                   10                  15

Ser Val Arg Val Ser Cys Lys Ala Ser Gly Tyr Ser Phe Thr Trp Val
            20                  25                  30

Arg Gln Ser Pro Gly Lys Gly Leu Glu Trp Ile Gly Lys Ala Thr Leu
        35                  40                  45

Thr Val Asp Lys Ser Thr Ser Thr Ala Tyr Met Glu Leu Ser Ser Leu
    50                  55                  60

Arg Ser Glu Asp Thr Ala Val Tyr Phe Cys Ala Arg Trp Gly Gln Gly
65                  70                  75                  80

Thr Thr Val Thr Val Ser Ser
                85

<210> SEQ ID NO 91
<211> LENGTH: 87
<212> TYPE: PRT
<213> ORGANISM: Artificial Sequence
<220> FEATURE:
<223> OTHER INFORMATION: Synthetic humanized FR1, FR2, FR3 and FR4 of HC-08

<400> SEQUENCE: 91

Gln Ile Gln Leu Val Gln Ser Gly Gly Glu Val Lys Lys Pro Gly Ala
1               5                   10                  15

Ser Val Arg Val Ser Cys Lys Ala Ser Gly Tyr Ser Phe Thr Trp Val
            20                  25                  30

Arg Gln Ser Pro Gly Lys Gly Leu Glu Trp Ile Gly Lys Ala Thr Leu
        35                  40                  45

Thr Val Asp Lys Ser Thr Ser Thr Ala Tyr Met Glu Leu Ser Ser Leu
    50                  55                  60

Arg Ser Glu Asp Thr Ala Val Tyr Phe Cys Ala Arg Trp Gly Gln Gly
65                  70                  75                  80

Thr Thr Val Thr Val Ser Ser
                85

<210> SEQ ID NO 92
<211> LENGTH: 87
<212> TYPE: PRT
<213> ORGANISM: Artificial Sequence
<220> FEATURE:
<223> OTHER INFORMATION: Synthetic humanized FR1, FR2, FR3 and FR4 of HC-08R1

<400> SEQUENCE: 92

Gln Ile Gln Leu Val Gln Ser Gly Gly Glu Val Lys Lys Pro Gly Ala
1               5                   10                  15

Ser Val Arg Val Ser Cys Lys Ala Ser Gly Tyr Ser Phe Thr Trp Val
            20                  25                  30

Arg Gln Ser Pro Gly Lys Gly Leu Glu Trp Ile Gly Lys Ala Thr Leu
        35                  40                  45

Thr Val Asp Lys Ser Thr Ser Thr Ala Tyr Met Glu Leu Ser Ser Leu
            50                  55                  60

Arg Ser Glu Asp Thr Ala Val Tyr Phe Cys Ala Arg Trp Gly Gln Gly
65                  70                  75                  80

Thr Thr Val Thr Val Ser Ser
                85

<210> SEQ ID NO 93
<211> LENGTH: 87
<212> TYPE: PRT
<213> ORGANISM: Artificial Sequence
<220> FEATURE:
<223> OTHER INFORMATION: Synthetic humanized FR1, FR2, FR3 and FR4 of
      HC-11

<400> SEQUENCE: 93

Gln Ile Gln Leu Val Gln Ser Gly Pro Glu Val Lys Lys Pro Gly Ala
1               5                   10                  15

Ser Val Arg Val Ser Cys Lys Ala Ser Gly Tyr Ser Phe Thr Trp Val
            20                  25                  30

Arg Gln Ser Pro Gly Lys Gly Leu Glu Trp Ile Gly Lys Ala Thr Leu
        35                  40                  45

Thr Val Asp Lys Ser Thr Ser Thr Ala Tyr Met Glu Leu Ser Ser Leu
            50                  55                  60

Arg Ser Glu Asp Thr Ala Val Tyr Phe Cys Ala Arg Trp Gly Gln Gly
65                  70                  75                  80

Thr Thr Val Thr Val Ser Ser
                85

<210> SEQ ID NO 94
<211> LENGTH: 87
<212> TYPE: PRT
<213> ORGANISM: Artificial Sequence
<220> FEATURE:
<223> OTHER INFORMATION: Synthetic humanized FR1, FR2, FR3 and FR4 of
      HC-12

<400> SEQUENCE: 94

Gln Ile Gln Leu Val Gln Ser Gly Pro Glu Leu Lys Lys Pro Gly Ala
1               5                   10                  15

Ser Val Arg Val Ser Cys Lys Ala Ser Gly Tyr Ser Phe Thr Trp Val
            20                  25                  30

Arg Gln Ser Pro Gly Lys Gly Leu Glu Trp Ile Gly Lys Ala Thr Leu
        35                  40                  45

Thr Val Asp Lys Ser Thr Ser Thr Ala Tyr Met Glu Leu Ser Ser Leu
            50                  55                  60

Arg Ser Glu Asp Thr Ala Val Tyr Phe Cys Ala Arg Trp Gly Gln Gly
65                  70                  75                  80

Thr Thr Val Thr Val Ser Ser
                85

<210> SEQ ID NO 95
<211> LENGTH: 87
<212> TYPE: PRT
<213> ORGANISM: Artificial Sequence
<220> FEATURE:
<223> OTHER INFORMATION: Synthetic humanized FR1, FR2, FR3 and FR4 of
      HC-09

<400> SEQUENCE: 95

Gln Ile Gln Leu Val Gln Ser Gly Pro Glu Leu Val Lys Pro Gly Ala
1               5                   10                  15

Ser Val Arg Val Ser Cys Lys Ala Ser Gly Tyr Ser Phe Thr Trp Val
            20                  25                  30

Arg Gln Ser Pro Gly Lys Gly Leu Glu Trp Ile Gly Lys Ala Thr Leu
        35                  40                  45

Thr Val Asp Lys Ser Thr Ser Thr Ala Tyr Met Glu Leu Ser Ser Leu
    50                  55                  60

Arg Ser Glu Asp Thr Ala Val Tyr Phe Cys Ala Arg Trp Gly Gln Gly
65                  70                  75                  80

Thr Thr Val Thr Val Ser Ser
                85

<210> SEQ ID NO 96
<211> LENGTH: 87
<212> TYPE: PRT
<213> ORGANISM: Artificial Sequence
<220> FEATURE:
<223> OTHER INFORMATION: Synthetic humanized FR1, FR2, FR3 and FR4 of
      HC-10

<400> SEQUENCE: 96

Gln Ile Gln Leu Val Gln Ser Gly Pro Glu Val Val Lys Pro Gly Ala
1               5                   10                  15

Ser Val Arg Val Ser Cys Lys Ala Ser Gly Tyr Ser Phe Thr Trp Val
            20                  25                  30

Arg Gln Ser Pro Gly Lys Gly Leu Glu Trp Ile Gly Lys Ala Thr Leu
        35                  40                  45

Thr Val Asp Lys Ser Thr Ser Thr Ala Tyr Met Glu Leu Ser Ser Leu
    50                  55                  60

Arg Ser Glu Asp Thr Ala Val Tyr Phe Cys Ala Arg Trp Gly Gln Gly
65                  70                  75                  80

Thr Thr Val Thr Val Ser Ser
                85

<210> SEQ ID NO 97
<211> LENGTH: 107
<212> TYPE: PRT
<213> ORGANISM: Homo sapiens

<400> SEQUENCE: 97

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 98
<211> LENGTH: 332
<212> TYPE: PRT
<213> ORGANISM: Homo sapiens

<400> SEQUENCE: 98

```
Glu Phe Ala Ser Thr Lys Gly Pro Ser Val Phe Pro Leu Ala Pro Ser
  1               5                  10                  15
Ser Lys Ser Thr Ser Gly Gly Thr Ala Ala Leu Gly Cys Leu Val Lys
             20                  25                  30
Asp Tyr Phe Pro Glu Pro Val Thr Val Ser Trp Asn Ser Gly Ala Leu
         35                  40                  45
Thr Ser Gly Val His Thr Phe Pro Ala Val Leu Gln Ser Ser Gly Leu
     50                  55                  60
Tyr Ser Leu Ser Ser Val Val Thr Val Pro Ser Ser Ser Leu Gly Thr
 65                  70                  75                  80
Gln Thr Tyr Ile Cys Asn Val Asn His Lys Pro Ser Asn Thr Lys Val
                 85                  90                  95
Asp Lys Lys Val Glu Pro Lys Ser Cys Asp Lys Thr His Thr Cys Pro
            100                 105                 110
Pro Cys Pro Ala Pro Glu Leu Leu Gly Gly Pro Ser Val Phe Leu Phe
        115                 120                 125
Pro Pro Lys Pro Lys Asp Thr Leu Met Ile Ser Arg Thr Pro Glu Val
130                 135                 140
Thr Cys Val Val Val Asp Val Ser His Glu Asp Pro Glu Val Lys Phe
145                 150                 155                 160
Asn Trp Tyr Val Asp Gly Val Glu Val His Asn Ala Lys Thr Lys Pro
                165                 170                 175
Arg Glu Glu Gln Tyr Asn Ser Thr Tyr Arg Val Val Ser Val Leu Thr
            180                 185                 190
Val Leu His Gln Asp Trp Leu Asn Gly Lys Glu Tyr Lys Cys Lys Val
        195                 200                 205
Ser Asn Lys Ala Leu Pro Ala Pro Ile Glu Lys Thr Ile Ser Lys Ala
210                 215                 220
Lys Gly Gln Pro Arg Glu Pro Gln Val Tyr Thr Leu Pro Pro Ser Arg
225                 230                 235                 240
Asp Glu Leu Thr Lys Asn Gln Val Ser Leu Thr Cys Leu Val Lys Gly
                245                 250                 255
Phe Tyr Pro Ser Asp Ile Ala Val Glu Trp Glu Ser Asn Gly Gln Pro
            260                 265                 270
Glu Asn Asn Tyr Lys Thr Thr Pro Pro Val Leu Asp Ser Asp Gly Ser
        275                 280                 285
Phe Phe Leu Tyr Ser Lys Leu Thr Val Asp Lys Ser Arg Trp Gln Gln
290                 295                 300
Gly Asn Val Phe Ser Cys Ser Val Met His Glu Ala Leu His Asn His
305                 310                 315                 320
Tyr Thr Gln Lys Ser Leu Ser Leu Ser Pro Gly Lys
                325                 330
```

<210> SEQ ID NO 99
<211> LENGTH: 107
<212> TYPE: PRT
<213> ORGANISM: Homo sapiens

<400> SEQUENCE: 99

```
Arg Thr Val Ala Ala Pro Ser Val Phe Ile Phe Pro Pro Ser Asp Glu
  1               5                  10                  15
Gln Leu Lys Ser Gly Thr Ala Ser Val Val Cys Leu Leu Asn Asn Phe
             20                  25                  30
Tyr Pro Arg Glu Ala Lys Val Gln Trp Lys Val Asp Asn Ala Leu Gln
```

```
                35                  40                  45
Ser Gly Asn Ser Gln Glu Ser Val Thr Glu Gln Asp Ser Lys Asp Ser
 50                  55                  60
Thr Tyr Ser Leu Ser Ser Thr Leu Thr Leu Ser Lys Ala Asp Tyr Glu
 65                  70                  75                  80
Lys His Lys Val Tyr Ala Cys Glu Val Thr His Gln Gly Leu Ser Ser
                 85                  90                  95
Pro Val Thr Lys Ser Phe Asn Arg Gly Glu Cys
            100                 105

<210> SEQ ID NO 100
<211> LENGTH: 329
<212> TYPE: PRT
<213> ORGANISM: Homo sapiens

<400> SEQUENCE: 100

Glu Phe Ala Ser Thr Lys Gly Pro Ser Val Phe Pro Leu Ala Pro Cys
  1               5                  10                  15
Ser Arg Ser Thr Ser Glu Ser Thr Ala Ala Leu Gly Cys Leu Val Lys
                 20                  25                  30
Asp Tyr Phe Pro Glu Pro Val Thr Val Ser Trp Asn Ser Gly Ala Leu
             35                  40                  45
Thr Ser Gly Val His Thr Phe Pro Ala Val Leu Gln Ser Ser Gly Leu
 50                  55                  60
Tyr Ser Leu Ser Ser Val Val Thr Val Pro Ser Ser Ser Leu Gly Thr
 65                  70                  75                  80
Lys Thr Tyr Thr Cys Asn Val Asp His Lys Pro Ser Asn Thr Lys Val
                 85                  90                  95
Asp Lys Arg Val Glu Ser Lys Tyr Gly Pro Pro Cys Pro Ser Cys Pro
            100                 105                 110
Ala Pro Glu Phe Leu Gly Gly Pro Ser Val Phe Leu Phe Pro Pro Lys
            115                 120                 125
Pro Lys Asp Thr Leu Met Ile Ser Arg Thr Pro Glu Val Thr Cys Val
130                 135                 140
Val Val Asp Val Ser Gln Glu Asp Pro Glu Val Gln Phe Asn Trp Tyr
145                 150                 155                 160
Val Asp Gly Val Glu Val His Asn Ala Lys Thr Lys Pro Arg Glu Glu
                165                 170                 175
Gln Phe Asn Ser Thr Tyr Arg Val Val Ser Val Leu Thr Val Leu His
            180                 185                 190
Gln Asp Trp Leu Asn Gly Lys Glu Tyr Lys Cys Lys Val Ser Asn Lys
        195                 200                 205
Gly Leu Pro Ser Ser Ile Glu Lys Thr Ile Ser Lys Ala Lys Gly Gln
    210                 215                 220
Pro Arg Glu Pro Gln Val Tyr Thr Leu Pro Pro Ser Gln Glu Glu Met
225                 230                 235                 240
Thr Lys Asn Gln Val Ser Leu Thr Cys Leu Val Lys Gly Phe Tyr Pro
                245                 250                 255
Ser Asp Ile Ala Val Glu Trp Glu Ser Asn Gly Gln Pro Glu Asn Asn
            260                 265                 270
Tyr Lys Thr Thr Pro Pro Val Leu Asp Ser Asp Gly Ser Phe Phe Leu
        275                 280                 285
Tyr Ser Arg Leu Thr Val Asp Lys Ser Arg Trp Gln Glu Gly Asn Val
    290                 295                 300
Phe Ser Cys Ser Val Met His Glu Ala Leu His Asn His Tyr Thr Gln
```

Lys Ser Leu Ser Leu Ser Leu Gly Lys
            325

<210> SEQ ID NO 101
<211> LENGTH: 17
<212> TYPE: PRT
<213> ORGANISM: Artificial Sequence
<220> FEATURE:
<223> OTHER INFORMATION: Synthetic CDR2 of HC-08

<400> SEQUENCE: 101

Tyr Ile Asp Pro Tyr Asn Gly Ile Thr Ile Tyr Asp Gln Asn Leu Lys
1               5                   10                  15

Gly

<210> SEQ ID NO 102
<211> LENGTH: 38
<212> TYPE: PRT
<213> ORGANISM: Artificial Sequence
<220> FEATURE:
<223> OTHER INFORMATION: Synthetic FR1 and FR2 of CH36-LC

<400> SEQUENCE: 102

Asp Ile Gln Met Thr Gln Ser Pro Ala Ser Gln Ser Ala Ser Leu Gly
1               5                   10                  15

Glu Ser Val Thr Ile Thr Cys Trp Tyr Gln Gln Lys Pro Gly Lys Ser
            20                  25                  30

Pro Gln Leu Leu Ile Tyr
        35

<210> SEQ ID NO 103
<211> LENGTH: 23
<212> TYPE: PRT
<213> ORGANISM: Artificial Sequence
<220> FEATURE:
<223> OTHER INFORMATION: Synthetic FR1 of CH36-LC

<400> SEQUENCE: 103

Asp Ile Gln Met Thr Gln Ser Pro Ala Ser Gln Ser Ala Ser Leu Gly
1               5                   10                  15

Glu Ser Val Thr Ile Thr Cys
            20

<210> SEQ ID NO 104
<211> LENGTH: 15
<212> TYPE: PRT
<213> ORGANISM: Artificial Sequence
<220> FEATURE:
<223> OTHER INFORMATION: Synthetic FR2 of CH36-LC

<400> SEQUENCE: 104

Trp Tyr Gln Gln Lys Pro Gly Lys Ser Pro Gln Leu Leu Ile Tyr
1               5                   10                  15

<210> SEQ ID NO 105
<211> LENGTH: 32
<212> TYPE: PRT
<213> ORGANISM: Artificial Sequence
<220> FEATURE:
<223> OTHER INFORMATION: Synthetic FR3 of CH36-LC

<400> SEQUENCE: 105

Gly Val Pro Ser Arg Phe Ser Gly Ser Gly Ser Gly Thr Lys Phe Ser
1               5                   10                  15

-continued

Phe Lys Ile Ser Ser Leu Gln Ala Glu Asp Phe Val Asn Tyr Tyr Cys
             20                  25                  30

<210> SEQ ID NO 106
<211> LENGTH: 10
<212> TYPE: PRT
<213> ORGANISM: Artificial Sequence
<220> FEATURE:
<223> OTHER INFORMATION: Synthetic FR4 of CH36-LC

<400> SEQUENCE: 106

Phe Gly Ala Gly Thr Lys Leu Glu Leu Lys
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Synthetic humanized FR4 of LC-03

<400> SEQUENCE: 107

Phe Gly Ala Gly Thr Lys Leu Glu Ile Lys
1               5                   10

<210> SEQ ID NO 108
<211> LENGTH: 15
<212> TYPE: PRT
<213> ORGANISM: Artificial Sequence
<220> FEATURE:
<223> OTHER INFORMATION: Synthetic humanized FR2 of LC-04

<400> SEQUENCE: 108

Trp Tyr Leu Gln Lys Pro Gly Lys Ser Pro Gln Leu Leu Ile Tyr
1               5                   10                  15

<210> SEQ ID NO 109
<211> LENGTH: 23
<212> TYPE: PRT
<213> ORGANISM: Artificial Sequence
<220> FEATURE:
<223> OTHER INFORMATION: Synthetic humanized FR1 of LC-05

<400> SEQUENCE: 109

Asp Ile Gln Met Thr Gln Ser Pro Ala Ser Leu Ser Ala Ser Val Gly
1               5                   10                  15

Asp Arg Val Thr Ile Thr Cys
             20

<210> SEQ ID NO 110
<211> LENGTH: 10
<212> TYPE: PRT
<213> ORGANISM: Artificial Sequence
<220> FEATURE:
<223> OTHER INFORMATION: Synthetic humanized FR4 of LC-05

<400> SEQUENCE: 110

Phe Gly Gln Gly Thr Lys Leu Glu Ile Lys
1               5                   10

<210> SEQ ID NO 111
<211> LENGTH: 32
<212> TYPE: PRT
<213> ORGANISM: Artificial Sequence
<220> FEATURE:
<223> OTHER INFORMATION: Synthetic humanized FR3 of LC-07

```
<400> SEQUENCE: 111

Gly Val Pro Ser Arg Phe Ser Gly Ser Gly Ser Gly Thr Asp Phe Ser
1               5                   10                  15

Phe Thr Ile Ser Ser Leu Gln Pro Glu Asp Phe Val Asn Tyr Tyr Cys
            20                  25                  30

<210> SEQ ID NO 112
<211> LENGTH: 32
<212> TYPE: PRT
<213> ORGANISM: Artificial Sequence
<220> FEATURE:
<223> OTHER INFORMATION: Synthetic humanized FR3 of LC-08

<400> SEQUENCE: 112

Gly Val Pro Ser Arg Phe Ser Gly Ser Gly Ser Gly Thr Asp Phe Ser
1               5                   10                  15

Phe Thr Ile Ser Ser Leu Gln Pro Glu Asp Phe Ala Thr Tyr Tyr Cys
            20                  25                  30

<210> SEQ ID NO 113
<211> LENGTH: 32
<212> TYPE: PRT
<213> ORGANISM: Artificial Sequence
<220> FEATURE:
<223> OTHER INFORMATION: Synthetic humanized FR3 of LC-10

<400> SEQUENCE: 113

Gly Val Pro Ser Arg Phe Ser Gly Ser Gly Ser Gly Thr Asp Phe Ser
1               5                   10                  15

Phe Thr Ile Ser Ser Leu Gln Pro Glu Asp Phe Ala Asn Tyr Tyr Cys
            20                  25                  30

<210> SEQ ID NO 114
<211> LENGTH: 32
<212> TYPE: PRT
<213> ORGANISM: Artificial Sequence
<220> FEATURE:
<223> OTHER INFORMATION: Synthetic humanized FR3 of LC-11

<400> SEQUENCE: 114

Gly Val Pro Ser Arg Phe Ser Gly Ser Gly Ser Gly Thr Lys Phe Ser
1               5                   10                  15

Phe Thr Ile Ser Ser Leu Gln Pro Glu Asp Phe Ala Asn Tyr Tyr Cys
            20                  25                  30

<210> SEQ ID NO 115
<211> LENGTH: 15
<212> TYPE: PRT
<213> ORGANISM: Artificial Sequence
<220> FEATURE:
<223> OTHER INFORMATION: Synthetic humanized FR2 of LC-12

<400> SEQUENCE: 115

Trp Tyr Leu Gln Lys Pro Gly Gln Ser Pro Gln Leu Leu Ile Tyr
1               5                   10                  15

<210> SEQ ID NO 116
<211> LENGTH: 11
<212> TYPE: PRT
<213> ORGANISM: Artificial Sequence
<220> FEATURE:
<223> OTHER INFORMATION: Synthetic CDR1 of CH36-LC

<400> SEQUENCE: 116

Leu Ala Ser Gln Thr Ile Asp Thr Trp Leu Ala
```

<210> SEQ ID NO 117
<211> LENGTH: 30
<212> TYPE: PRT
<213> ORGANISM: Artificial Sequence
<220> FEATURE:
<223> OTHER INFORMATION: Synthetic FR1 of CH36-HC

<400> SEQUENCE: 117

Glu Ile Gln Leu Gln Gln Ser Gly Pro Glu Leu Val Lys Pro Gly Ala
1               5                   10                  15
Ser Val Gln Val Ser Cys Lys Thr Ser Gly Tyr Ser Phe Thr
            20                  25                  30

<210> SEQ ID NO 118
<211> LENGTH: 14
<212> TYPE: PRT
<213> ORGANISM: Artificial Sequence
<220> FEATURE:
<223> OTHER INFORMATION: Synthetic FR2 of CH36-HC

<400> SEQUENCE: 118

Trp Val Arg Gln Ser His Gly Lys Ser Leu Glu Trp Ile Gly
1               5                   10

<210> SEQ ID NO 119
<211> LENGTH: 32
<212> TYPE: PRT
<213> ORGANISM: Artificial Sequence
<220> FEATURE:
<223> OTHER INFORMATION: Synthetic FR3 of CH36-HC

<400> SEQUENCE: 119

Lys Ala Thr Leu Thr Val Asp Lys Ser Ser Thr Thr Ala Phe Met His
1               5                   10                  15
Leu Asn Ser Leu Thr Ser Asp Asp Ser Ala Val Tyr Phe Cys Ala Arg
            20                  25                  30

<210> SEQ ID NO 120
<211> LENGTH: 11
<212> TYPE: PRT
<213> ORGANISM: Artificial Sequence
<220> FEATURE:
<223> OTHER INFORMATION: Synthetic FR4 of CH36-HC

<400> SEQUENCE: 120

Trp Gly Gln Gly Thr Thr Leu Thr Val Ser Ser
1               5                   10

<210> SEQ ID NO 121
<211> LENGTH: 30
<212> TYPE: PRT
<213> ORGANISM: Artificial Sequence
<220> FEATURE:
<223> OTHER INFORMATION: Synthetic humanized FR1 of HC-01

<400> SEQUENCE: 121

Gln Ile Gln Leu Gln Gln Ser Gly Pro Glu Leu Val Lys Pro Gly Ala
1               5                   10                  15
Ser Val Gln Val Ser Cys Lys Thr Ser Gly Tyr Ser Phe Thr
            20                  25                  30

<210> SEQ ID NO 122
<211> LENGTH: 11
<212> TYPE: PRT

```
<213> ORGANISM: Artificial Sequence
<220> FEATURE:
<223> OTHER INFORMATION: Synthetic humanized FR4 of HC-01

<400> SEQUENCE: 122

Trp Gly Gln Gly Thr Thr Val Thr Val Ser Ser
 1               5                  10

<210> SEQ ID NO 123
<211> LENGTH: 14
<212> TYPE: PRT
<213> ORGANISM: Artificial Sequence
<220> FEATURE:
<223> OTHER INFORMATION: Synthetic humanized FR2 of HC-02

<400> SEQUENCE: 123

Trp Val Arg Gln Ser Pro Gly Lys Gly Leu Glu Trp Ile Gly
 1               5                  10

<210> SEQ ID NO 124
<211> LENGTH: 32
<212> TYPE: PRT
<213> ORGANISM: Artificial Sequence
<220> FEATURE:
<223> OTHER INFORMATION: Synthetic humanized FR3 of HC-03

<400> SEQUENCE: 124

Lys Ala Thr Leu Thr Val Asp Lys Ser Ser Thr Ala Phe Met His
 1               5                  10                  15

Leu Asn Ser Leu Arg Ser Glu Asp Thr Ala Val Tyr Phe Cys Ala Arg
            20                  25                  30

<210> SEQ ID NO 125
<211> LENGTH: 32
<212> TYPE: PRT
<213> ORGANISM: Artificial Sequence
<220> FEATURE:
<223> OTHER INFORMATION: Synthetic humanized FR3 of HC-04

<400> SEQUENCE: 125

Lys Ala Thr Leu Thr Val Asp Lys Ser Ser Thr Ala Phe Met Glu
 1               5                  10                  15

Leu Ser Ser Leu Arg Ser Glu Asp Thr Ala Val Tyr Phe Cys Ala Arg
            20                  25                  30

<210> SEQ ID NO 126
<211> LENGTH: 32
<212> TYPE: PRT
<213> ORGANISM: Artificial Sequence
<220> FEATURE:
<223> OTHER INFORMATION: Synthetic humanized FR3 of HC-05

<400> SEQUENCE: 126

Lys Ala Thr Leu Thr Val Asp Lys Ser Thr Ser Thr Ala Tyr Met Glu
 1               5                  10                  15

Leu Ser Ser Leu Arg Ser Glu Asp Thr Ala Val Tyr Phe Cys Ala Arg
            20                  25                  30

<210> SEQ ID NO 127
<211> LENGTH: 30
<212> TYPE: PRT
<213> ORGANISM: Artificial Sequence
<220> FEATURE:
<223> OTHER INFORMATION: Synthetic humanized FR1 of HC-06

<400> SEQUENCE: 127
```

Gln Met Gln Leu Gln Gln Ser Gly Gly Glu Leu Val Lys Pro Gly Ala
1               5                   10                  15

Ser Val Arg Val Ser Cys Lys Ala Ser Gly Tyr Ser Phe Thr
        20                  25                  30

<210> SEQ ID NO 128
<211> LENGTH: 30
<212> TYPE: PRT
<213> ORGANISM: Artificial Sequence
<220> FEATURE:
<223> OTHER INFORMATION: Synthetic humanized FR1 of HC-07

<400> SEQUENCE: 128

Gln Ile Gln Leu Val Gln Ser Gly Gly Glu Leu Val Lys Pro Gly Ala
1               5                   10                  15

Ser Val Arg Val Ser Cys Lys Ala Ser Gly Tyr Ser Phe Thr
        20                  25                  30

<210> SEQ ID NO 129
<211> LENGTH: 30
<212> TYPE: PRT
<213> ORGANISM: Artificial Sequence
<220> FEATURE:
<223> OTHER INFORMATION: Synthetic humanized FR1 of HC-08

<400> SEQUENCE: 129

Gln Ile Gln Leu Val Gln Ser Gly Gly Glu Val Lys Lys Pro Gly Ala
1               5                   10                  15

Ser Val Arg Val Ser Cys Lys Ala Ser Gly Tyr Ser Phe Thr
        20                  25                  30

<210> SEQ ID NO 130
<211> LENGTH: 30
<212> TYPE: PRT
<213> ORGANISM: Artificial Sequence
<220> FEATURE:
<223> OTHER INFORMATION: Synthetic humanized FR1 of HC-11

<400> SEQUENCE: 130

Gln Ile Gln Leu Val Gln Ser Gly Pro Glu Val Lys Lys Pro Gly Ala
1               5                   10                  15

Ser Val Arg Val Ser Cys Lys Ala Ser Gly Tyr Ser Phe Thr
        20                  25                  30

<210> SEQ ID NO 131
<211> LENGTH: 30
<212> TYPE: PRT
<213> ORGANISM: Artificial Sequence
<220> FEATURE:
<223> OTHER INFORMATION: Synthetic humanized FR1 of HC-12

<400> SEQUENCE: 131

Gln Ile Gln Leu Val Gln Ser Gly Pro Glu Leu Lys Lys Pro Gly Ala
1               5                   10                  15

Ser Val Arg Val Ser Cys Lys Ala Ser Gly Tyr Ser Phe Thr
        20                  25                  30

<210> SEQ ID NO 132
<211> LENGTH: 30
<212> TYPE: PRT
<213> ORGANISM: Artificial Sequence
<220> FEATURE:
<223> OTHER INFORMATION: Synthetic humanized FR1 of HC-09

<400> SEQUENCE: 132

```
Gln Ile Gln Leu Val Gln Ser Gly Pro Glu Leu Val Lys Pro Gly Ala
1               5                   10                  15

Ser Val Arg Val Ser Cys Lys Ala Ser Gly Tyr Ser Phe Thr
            20                  25                  30

<210> SEQ ID NO 133
<211> LENGTH: 30
<212> TYPE: PRT
<213> ORGANISM: Artificial Sequence
<220> FEATURE:
<223> OTHER INFORMATION: Synthetic humanized FR1 of HC-10

<400> SEQUENCE: 133

Gln Ile Gln Leu Val Gln Ser Gly Pro Glu Val Val Lys Pro Gly Ala
1               5                   10                  15

Ser Val Arg Val Ser Cys Lys Ala Ser Gly Tyr Ser Phe Thr
            20                  25                  30

<210> SEQ ID NO 134
<211> LENGTH: 5
<212> TYPE: PRT
<213> ORGANISM: Artificial Sequence
<220> FEATURE:
<223> OTHER INFORMATION: Synthetic CDR1 of CH36-HC

<400> SEQUENCE: 134

Asp Tyr Asn Val Tyr
1               5
```